(12) United States Patent
Feld et al.

(10) Patent No.: US 8,007,779 B2
(45) Date of Patent: Aug. 30, 2011

(54) NUCLEIC ACID CONSTRUCTS AND CELLS, AND METHODS UTILIZING SAME FOR MODIFYING THE ELECTROPHYSIOLOGICAL FUNCTION OF EXCITABLE TISSUES

(75) Inventors: Yair Feld, Haifa (IL); Lior Gepstein, Haifa (IL); Shimon Marom, Haifa (IL)

(73) Assignee: GeneGrafts Ltd., Haifa (IL)

( * ) Notice: Subject to any disclaimer, the term of this patent is extended or adjusted under 35 U.S.C. 154(b) by 174 days.

(21) Appl. No.: 12/320,206

(22) Filed: Jan. 21, 2009

(65) Prior Publication Data

US 2009/0257990 A1 Oct. 15, 2009

Related U.S. Application Data

(63) Continuation of application No. 10/919,343, filed on Aug. 17, 2004, now Pat. No. 7,491,385, which is a continuation-in-part of application No. 10/399,715, filed as application No. PCT/IL01/00833 on Sep. 5, 2001, now abandoned, which is a continuation of application No. 09/691,889, filed on Oct. 20, 2000.

(51) Int. Cl.
*A01N 63/00* (2006.01)
(52) U.S. Cl. .................................................... 424/93.1
(58) Field of Classification Search .................. None
See application file for complete search history.

(56) References Cited

U.S. PATENT DOCUMENTS

| | | | |
|---|---|---|---|
| 5,602,301 A | 2/1997 | Field | |
| 5,837,220 A | 11/1998 | Blake et al. | |
| 5,955,259 A | 9/1999 | Holmes et al. | |
| 6,013,766 A | 1/2000 | Elgoyhen et al. | |
| 6,087,488 A | 7/2000 | Ganetzky et al. | |
| 6,099,832 A | 8/2000 | Mickle et al. | |
| 6,100,046 A | 8/2000 | Elgoyhen et al. | |
| 6,110,459 A | 8/2000 | Mickle et al. | |
| 6,864,364 B1 | 3/2005 | Splawski et al. | |
| 7,294,333 B1 | 11/2007 | Feld et al. | |
| 7,491,385 B2 | 2/2009 | Feld et al. | |
| 2004/0029148 A1 | 2/2004 | Feld et al. | |
| 2005/0008628 A1 | 1/2005 | Feld et al. | |
| 2008/0112927 A1 | 5/2008 | Feld et al. | |

FOREIGN PATENT DOCUMENTS

| | | |
|---|---|---|
| CA | 2369812 | 10/2000 |
| EP | 1326879 | 7/2003 |
| WO | WO 00/10604 | 3/2000 |
| WO | WO 00/18903 | 4/2000 |
| WO | WO 00/63434 | 10/2000 |
| WO | WO 02/33111 | 4/2002 |
| WO | WO 02/087419 | 11/2002 |
| WO | WO 2006/018836 | 2/2006 |

OTHER PUBLICATIONS

Loscher et al. Neurosci Res 1998;51:196-209.*
Folkerth et al. Neurol 1996;46:1219-25.*
Lindvall et al. Sci 1990;247:574-7.*
Dinsmore, Exp Opin Invest Drugs 1998;7:527-34.*
Grisolia, Epilepsy Behavior 2001;2:318-23.*
Gaudesius et al. Circ Res 2003;93:421.*
Communication Pursuant to Article 96(2) EPC Dated Nov. 2, 2004 From the European Patetn Office Re.: Application No. 01967651.9.
International Preliminary Report on Patentability Dated Apr. 26, 2007 From the International Bureau of WIPO Re.: Application No. PCT/IL2005/000881.
International Search Report and the Written Opinion Dated Feb. 8, 2007 From the International Searching Authority Re.: Application No. PCT/IL05/00881.
Notice of Allowance Dated Oct. 1, 2008 From the US Patent Office Re.: U.S. Appl. No. 10/919,343.
Official Action Dated May 2, 2007 From the US Patent and Trademark Office Re.: U.S. Appl. No. 10/919,343.
Official Action Dated Apr. 3, 2009 From the US Patent and Trademark Office Re.: U.S. Appl. No. 11/976,166.
Official Action Dated Feb. 3, 2006 From the US Patent and Trademark Office Re.: U.S. Appl. No. 10/399,715.
Official Action Dated Oct. 4, 2006 From the US Patent and Trademark Office Re.: U.S. Appl. No. 10/919,343.
Official Action Dated Feb. 6, 2006 From the US Patent and Trademark Office Re. U.S. Appl. No. 09/691,889.
Official Action Dated Jun. 6, 2008 From the US Patent and Trademark Office Re.: U.S. Appl. No. 10/919,343.
Official Action Dated Nov. 13, 2007 From the US Patent and Trademark Office Re.: U.S. Appl. No. 10/919,343.
Official Action Dated Apr. 21, 2006 From the US Patent and Trademark Office Re.: U.S. Appl. No. 10/399,715.
Official Action Dated Jul. 25, 2006 From the US Patent and Trademark Office Re.: U.S. Appl. No. 10/919,343.
Official Action Dated Aug. 29, 2007 From the US Patent and Trademark Office Re.: U.S. Appl. No. 10/919,343.
Official Action Dated Jul. 29, 2005 From the US Patent and Trademark Office Re.: U.S. Appl. No. 09/691,889.
Official Action Dated Jan. 30, 2007 From the US Patent and Trademark Office Re.: U.S. Appl. No. 09/691,889.
Requisition by the Examiner Dated Apr. 20, 2007 From the Canadian Intellectual Property Office Re.: Application No. 2,426,460.
Requisiton by the Examiner Dated Dec. 6, 2007 From the Canadian Intellectual Property Office Re.: Application No. 2,426,460.
Response Dated Feb. 21, 2005 to Communication Pursuant to Article 96(2) EPC of Nov. 2, 2004 From the European Patent Office Re.: Application No. 01967651.9.
Bader et al. "Repair and Reorganization of Minced Cardiac Muscle in the Adult Newt (*Notophthalmus viridescens*)", Journal of Morphology, 155(3): 349-357, 1978.
Banerjee "Genasense (Genta Inc.)", Current Opinion on Investigative Drugs, 2(4):574-580, 2001. Abstract.
Belluardo et al, "Expression of Connexin36 in the Adult and Developing Rat Brain", Brain Research, 865: 121-138, 2000.
Brukner "INGN-201. Introgen Therapeutics", Current Opinion on Investigative Drugs, 2(12): 1776-1785, 2001. Abstract.
Chiu et al. "Cellular Cardiomyoplasty: Myocardial Regeneration With Satellite Cell Implantation", Annual Meeting of the Thoraxic Surgeons, 60:12-18, 1995.

(Continued)

*Primary Examiner* — Q. Janice Li

(57) ABSTRACT

Polynucleotide expression constructs, populations of cells and methods of treating diseases caused by dysfunction in, or damage to, excitable tissues are provided.

3 Claims, 21 Drawing Sheets

OTHER PUBLICATIONS

Christ "Gap Junctions and Ion Channels: Relevance to Erectile Dysfunction", International Journal of Impotence Research, 12(Suppl.4): S15-S25, 2000.

Cohen et al. "ONYX-015-Onyx Pharmaceuticals", Current Opinion on Investigative Drugs, 2(12): 1770-1775, 2001. Abstract.

Crystal "Transfer of Genese to Humans: Early Lessons and Obstacles to Success", Science, 270: 404-410, 1995.

DeGroot et al. "Clinical Review 131: Gene Therapy for Thyroid Cancer: Where Do We Stand?", The Journal of Clinical Endocrinology & Metabolism, 86(7): 2923-2928, 2001.

Deonarain "Ligand-Targeted Receptor-Mediated Vectors for Gene Delivery", Expert Opinion on Therapeutic Patents, 8(1): 53-69, 1988.

Di Lazzaro et al. "Motor Cortex Hyperexcitability to Transcranial Magnetic Stimulation in Alzheimer's Disease", Journal of Neurology, Neurosurgery, and Psychiatry, 75: 555-559, 2004.

Donahue et al. "Focal Modification of Electrical Conduction in the Heart by Viral Gene Transfer", Nature Medicine, 6(12): 1395-1398, 2000.

Donahue et al. "Gene Therapy for Cardiac Arrhythmias", Trends in Cardiovascular Medicine, TCM, 15(6): 219-224, 2005.

Donahue et al. "Modification of Cellular Communication by Gene Transfer", Annals New York Academ of Sciences, 1047: 157-165, 2005.

Ebihara et al, "Co-Expression of Lens Fiber Connexins Modifies Hemi-Gap-Junctional Channel Behavior", Biophysical Journal, 76: 198-206, 1999.

Fast et al. "Anisotropic Conduction in Monolayers of Neonatal Rat Heart Cells Cultured on Collagen Substrate", Circulation Research, 75(3): 591-595, 1994.

Feld et al. "Electrophysiological Modulation of Cardiomyocytic Tissue by Transfected Fibroblasts Expressing Potassium Channels: A Novel Strategy to Manipulate Excitability", Circulation, 105(4): 522-529, 2002.

Freed et al. "Survival of Implanted Fetal Dopamine Cells and Neurologic Improvement 12 to 46 Months After Transplantation for Parkinson's Disease", New England Journal of Medicine, 327(22): 1549-1555, 1992.

Friedmann "Overcoming the Obstacles to Gene Therapy", Scientific American, 276(6): 96-101, 1997.

Gage "Cell Therapy", Nature, 392(Suppl.): 18-24, 1998.

Gardlik et al. "Vectors and Delivery Systems in Gene Therapy", Medical Science Monitor, 11(4): RA110-RA121, 2005.

Gepstein et al. "Somatic Gene and Cell Therapy Strategies for the Treatment of Cardiac Arrhytmias", American Journal of Physiology—Heart and Circulatory Physiology, 286: H815-H822, 2004.

Grosshans "Gene Therapy—When a Simple Concept Meets a Complex Reality. Review on Gene Therapy", Functional and Integrative Genomics, 1: 142-145, 2000.

Gussoni et al. "Normal Dystrophin Transcripts Detected in Duchenne Muscular Dystrophy Patients After Myoblast Transplantation", Nature, 356(6368): 435-438, 1992.

Hammond et al. "Angiogenic Gene Therapy for Heart Disease: A Review of Animal Studies and Clinical Trials", Cardiovascular Research, 49(3): 561-567, 2001.

Hoppe et al. "Manipulation of Cellular Excitability by Cell Fusion: Effects of Rapid Introducition of Transient Outward K+ Current on the Guinea Pig Action Potential", Circulation Research, 84: 964-972, 1999.

Jackowski "Neural Injury Repair: Hope for the Future as Barriers to Effective CNS Regeneration Become Clearer", British Journal of Neurosurgery, 9(3): 303-317, 1995.

Jockusch et al. "Long-Term Expression of Isomyosins and Myoendocrine Functions in Ectopic Grafts of Atrial Tissue", Proc. Natl. Acad. Sci. USA, 83(19): 7325-7329, 1986.

Johns et al. "Adenovirus-Mediated Expression of a Voltage-Gated Potassium Channel In Vitro (Rat Cardiac Myocytes) and In Vivo (Rat Liver)", Journal of Clinical Investigations, 96(2): 1152-1158, 1995.

Kirn "Oncolytic Virotherapy for Cancer With Adenovirus D11520 (Onyx-015): Results of Phase I and II Trials", Expert Opinion in Biological Therapy, 1(3): 525-538, 2001. Abstract.

Koh et al. "Differentiation and Long-Term Survival of C2C12 Myoblast Grafts in Heart", Journal of Clinical Investigation, 92(3): 1548-1554, 1993.

Koh et al. "Stable Fetal Cardiomyocyte Grafts in the Hearts of Dystrophic Mice and Dogs", The Journal of Clinical Investigation, 96(4): 2034-2042, 1995.

Lawson "Is There a Role for Potassium Channel Openers in Neuronal Ion Channel Disorders?", Expert Opinion on Investigational Drugs, 9(10): 2269-2280, 2000.

Leor et al, "Transplantation of Fetal Myocardial Tissue Into the Infarcted Myocardium of Rat—A Potential Method for Repair of Infarcted Myocardium?", Cell Transplants, 94(9 Suppl.II): 332-336, 1996.

Lerche et al. "Ion Channels and Epilepsy", American Journal of Medical Genetics, 106(2): 146-159, 2001.

Li et al. "Cardiomyocyte Transplantation Improves Heart Function", Annual Meeting of Thoraxic Surgeons, 62: 654-661, 1996.

Li et al. "Human Pediatric and Adult Ventricular Cardiomyocytes in Culture: Assessment of Phenotypic Changes With Passaging", Cardiovascular Research, 32: 362-373, 1996.

Li et al. "In Vivo Survival and Function of Transplanted Rat Cardiomyocytes", Circulation Research, 78(2): 283-288, 1996.

Li et al. "Method of Culturing Cardiomyocytes From Human Pediatric Ventricular Myocardium", Journal of Tissue Culture Methods, 14: 92-100, 1992.

Liss et al. "K-ATP Channels Promote the Differential Degeneration of Dopaminergic Midbrain Neurons", Nature Neuroscience, 8(12): 1742-1751, 2005.

Luo et al. "A Model of the Ventricular Cardiac Action Potential. Depolarization, Repolarization, and Their Interaction", Circulation Research, 68(6): 1501-1526, 1991.

Marelli et al. "Satellite Cell Implantation for Neo-Myocardial Regeneration", First International Congress of the Cell Transplanty Society, 1(2/3), 1992. Abstract.

Marom "Slow Changes in the Availability of Voltage-Gated Ion Channels: Effects on the Dynamics of Excitable Membrane", Journal of Member Biology, 161(2): 105-113, 1998.

Marom et al. "Modeling State-Dependent Inactivation of Membrane Currents", Biophysical Journal, 67(2): 515-520, 1994.

Marom et al. "State-Dependent Inactivation of the Kv3 Potassium Channel", Biophysical Journal, 67: 579-589, 1994.

Marshall "Gene Therapy's Growing Pains", Science, 269: 1050-1055, 1995.

Meir et al. "Ion Channels in Presynaptic Nerve Terminals and Control of Transmitter Release", Physiological Reviews, 79(3): 1019-1088, 1999.

Merritt et al. "Clinical Evaluation of Adenoviral-Mediated P53 Gene Transfer: Review on INGN 201 Studies", Semin. Oncology, 28(Suppl.16): 105-114, 2001. Abstract.

Miller et al. "Targeted Vectors for Gene Therapy", The FASEB Journal, 9(2): 190-199, 1995.

Murry et al. "Skeletal Myoblast Transplantation for Repair of Myocardial Necrosis", Journal of Clinical Investment, 98(11): 2512-2523, 1996.

Nasz et al. "Recombinant Adenovirus Vectors for Gene Therapy and Clinical Trials", Acta Microbiol. Immunol. Hung., 48(3-4): 323-348, 2001. Abstract.

Nuss et al. "Overexpression of a Human Potassium Channel Suppresses Cardiac Hyperexcitability in Rabbit Ventricular Myocytes", Journal of Clinical Investigation, 103(6): 889-896, 1999.

Orkin et al. "Report and Recommendations of the Panel to Assess the NIH Investment in Research on Gene Therapy", http://.nih.gov/news/panelrep.html, p. 1-40, 1995.

Pepin et al, "Motor Cortex Inhibition Is Not Impaired in Patients With Alzheimer's Disease: Evidence From Paired Transcranial Magnetic Stimulation", Journal of the Neurological Sciences, 170: 119-123, 1999.

Pera et al. "Human Embryonic Stem Cells", Journal of Cell Science, 113: 5-10, 2000.

Plotnikov et al. "Biological Pacemaker Implanted in Canine Left Bundle Branch Provides Ventricular Escape Rhythms That Have Physiologically Acceptable Rates", Circulation, 109: 506-512, 2004.

Race et al. "Muscle Regeneration of Injured Myocardium", Journal of Cellular Biochemistry, Suppl.150: 73, 1991. Abstract.

Race et al. "Satellite Cells for Myocardial Regeneration", Physiologost., 32: 220, 1989. Abstract.

Reinlib et al. "Cell Transplantation as Future Therapy for Cardiovascular Disease?: A Workshop of the National Heart, Lung, and Blood Institute", Circulation, 101(18): E182-187, 2000.

Rook et al. "Differences in Gap Junction Channels Between Cardiac Myocytes, Fibroblasts and Heterologous Pairs", American Journal of Physiology, 263(5)[Part 1]: C959-C977, 1992.

Rosen "Successful Gene Therapy for Severe Combined Immunodeficiency", New England Journal of Medicine, 346(16): 1241-1243, 2002.

Roth et al. "Nonviral Transfer of the Gene Encoding Coagulation Factor VIII in Patients With Severe Hemophilia A", New England Journal of Medicine, 344(23): 1735-1742, 2001.

Rubanyi "The Future of Human Gene Therapy", Molecular Aspects of Medicine, 22: 113-142, 2001.

Sangro et al. "Gene Therapy of Neoplastic LiverDiseases", International Journal of Cell Biology, 35(2): 135-148, 2003. Abstract.

Siegel "Biotechnology and Clinical Trials", Journal of Infectious Diseases, 185(Suppl.1): S52-S57, 2002.

Soonpaa et al. "Formation of Nascent Intercalated Disks Between Grafted Fetal Cardiomyocytes and Hot Myocardium", Science, 264(5155): 98-101, 1994.

Thomspon "Fetal Transplant Show Promise", Science, 257: 868-870, 1992.

Tomaselli et al. "Somatic Gene Transfer and Cardiac Arrhythmias: Problems and Prospects", Journal of Cardiovascular Electrophysiology, 14(5): 547-550, 2003.

Verma et al. "Gene Therapy—Promises, Problems and Prospects", Nature, 389(6648): 239-242, 1997.

International Search Report Dated Oct. 11, 2002 From the International Searching Authority Re.: Application No. PCT/IL01/00833.

Notice of References Cited in the Official Action Dated Sep. 1, 2004 From the US Patent and Trademark Office Re.: U.S. Appl. No. 09/691,889.

Notice of References Cited in the Official Action Dated Dec. 4, 2003 From the US Patent and Trademark Office Re.: U.S. Appl. No. 09/691,889.

Notice of References Cited in the Official Action Dated Oct. 4, 2002 From the US Patent and Trademark Office Re.: U.S. Appl. No. 09/691,889.

Response Dated May 26, 2010 to Requisition by the Examiner of Dec. 2, 2009 From the Canadian Intellectual Property Office Re.: Application No. 2,426,460.

Supplementary European Search Report Dated Aug. 10, 2004 From the European Patent Office Re.: Application No. EP 01967651.

Written Opinion Dated Sep. 27, 2004 From the International Searching Authority Re.: Application No. PCT/IL01/00833.

Partial European Search Report and the European Search Opinion Dated Feb. 9, 2010 From the European Patent Office Re.: Application No. 08160306.0.

Requisition by the Examiner Dated Dec. 2, 2009 From the Canadian Intellectual Property Office Re.: Application No. 2,426,460.

Koh et al. "Differentiation and Long-Term Survival of C2C12 Myoblast Grafts in Heart", Journal of Clinical Investigations, 92: 1549-1554, 1993.

Requisition by the Examiner Dated Dec. 6, 2007 From the Canadian Intellectual Property Office Re.: Application No. 2,426,460.

Feld et al. "Electrophysiological Modulation of Cardiomyocytic Tissue by Transfected Fibroblasts Expressing Potassium Channels: A Novel Strategy to Manipulate Excitability", Circulation, XP002287422, 105(4): 522-529, 2002.

Johns et al. "Adenovirus-Mediated Expression of a Voltage-Gated Potassium Channel In Vitro (Rat Cardiac Myocytes) and In Vivo (Rat Liver)", Journal of Clinical Investigations. XP000891385, 96(2): 1152-1158, Aug. 1995. Abstract, p. 1153, col. 1, p. 1157, col. 1, § 2-3.

Nuss et al. "Overexpression of a Human Potassium Channel Suppresses Cardiac Hyperexcitability in Rabbit Ventricular Myocytes", Journal of Clinical Investigation, XP002288643, 103(6): 889-896, Mar. 1999.

Rook et al. "Differences in Gap Junction Channels Between Cardiac Myocytes, Fibroblasts and Heterologous Pairs", American Journal of Physiology, XP009034048, 263(5/P.1): C959-C977, 1992.

Communication Pursuant to Article 94(3) EPC Dated Nov. 23, 2010 From the European Patent Office Re. Application No. 08160306.0.

Finberg et al. "Modulation of Excessive Neuronal Activity by Fibroblasts: Potentioal Use in Treatment of Parkinson's Disease", Restorative Nuerology and Neuroscience, 28: 803-815, 2010.

* cited by examiner

FIG. 1A
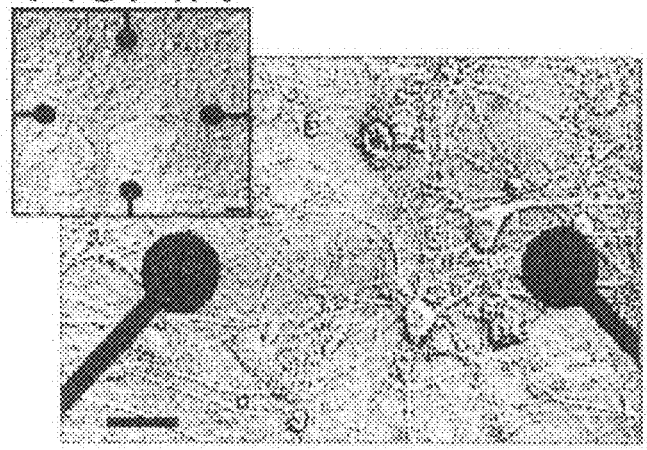
FIG. 1B
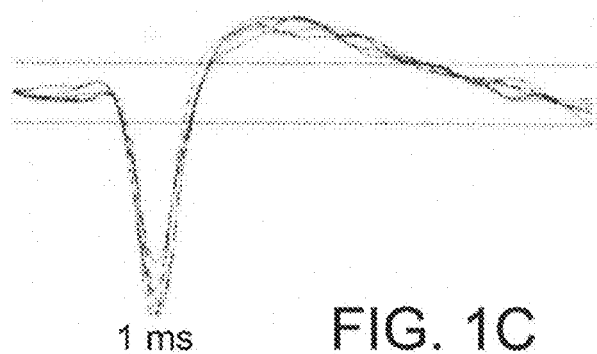
FIG. 1C
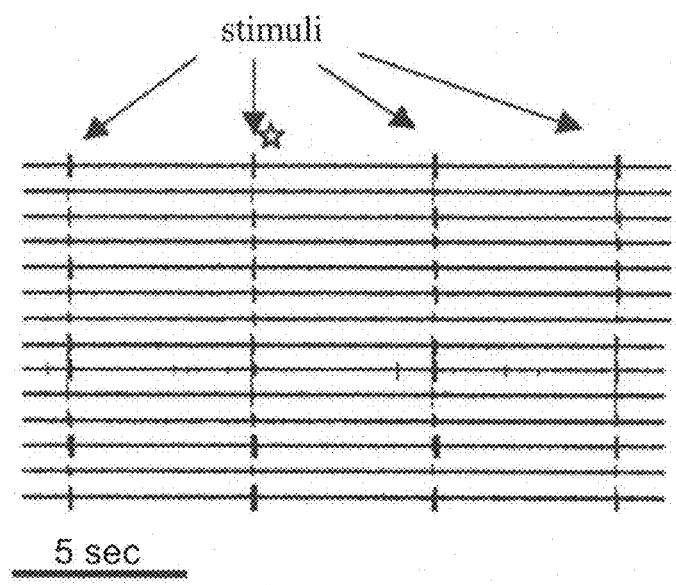
FIG. 1D

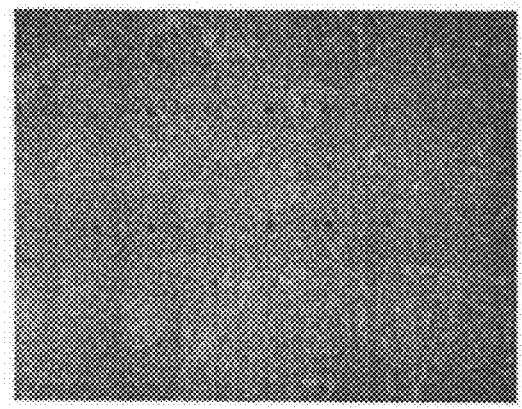
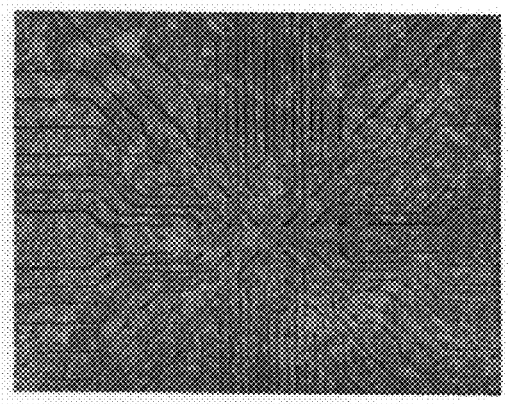
FIG. 4A  FIG. 4B
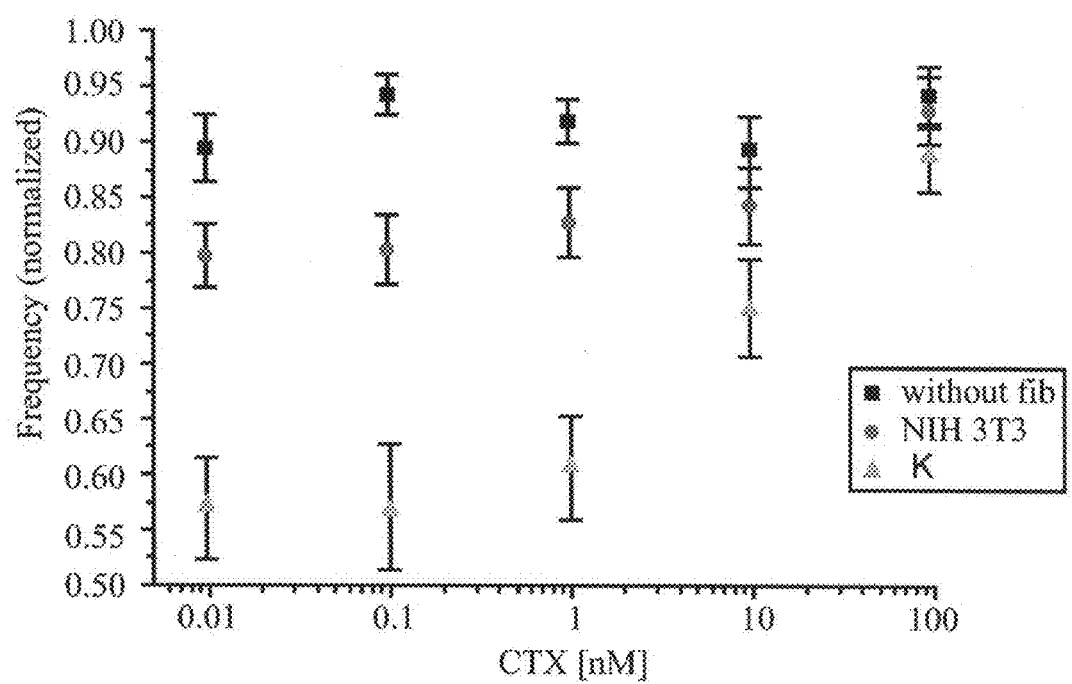
FIG. 5

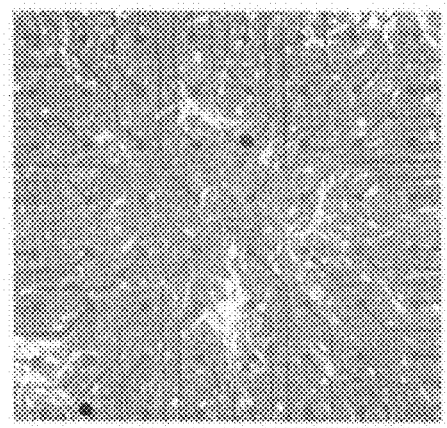
FIG. 6A
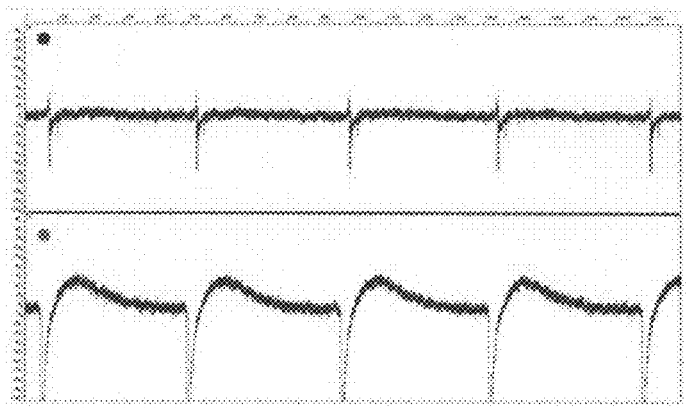
FIG. 6B
FIG. 6C
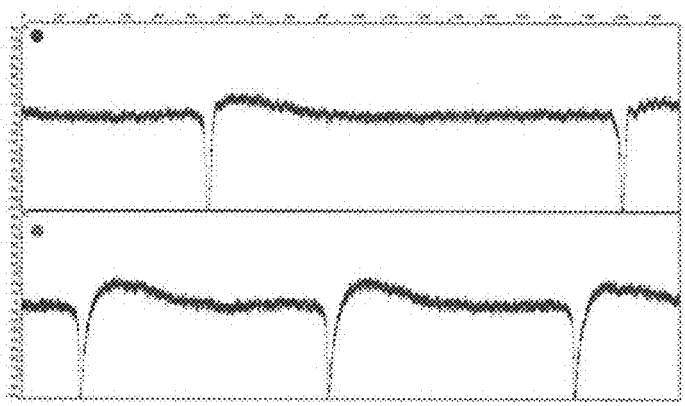
FIG. 6D
FIG. 6E
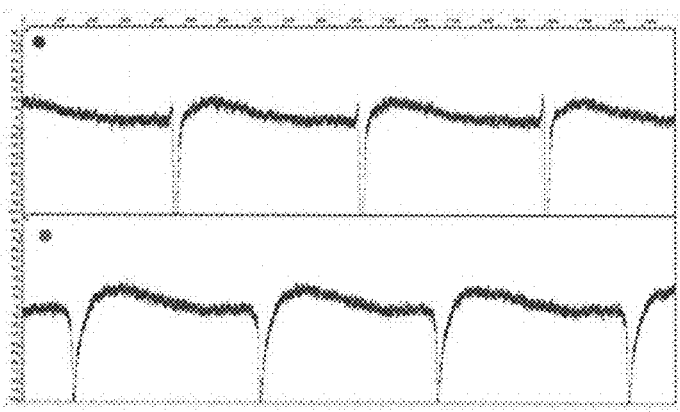
FIG. 6F
FIG. 6G

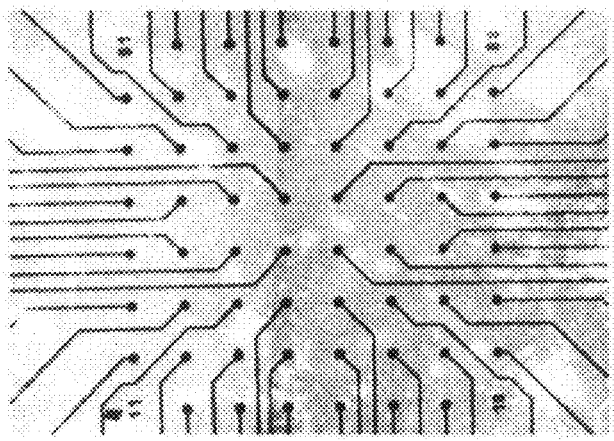
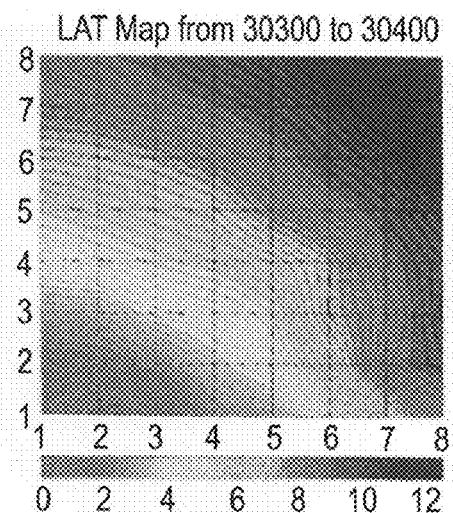
FIG. 12A  FIG. 12B
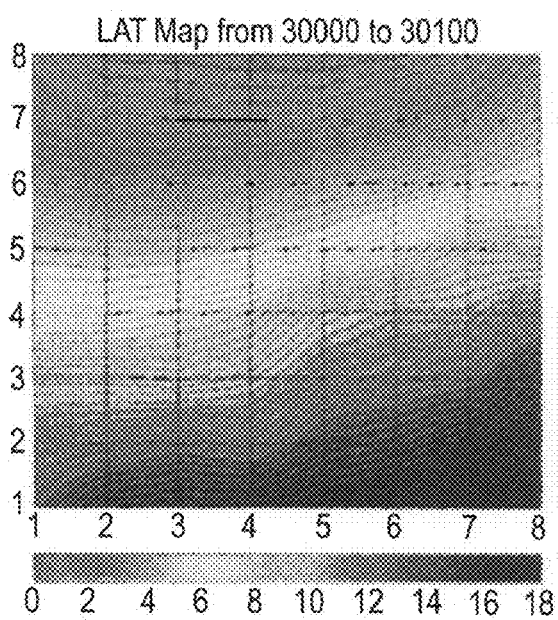
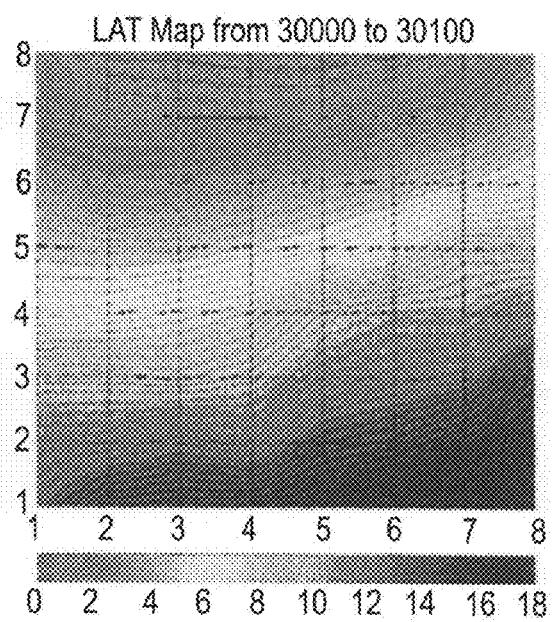
FIG. 12C  FIG. 12D

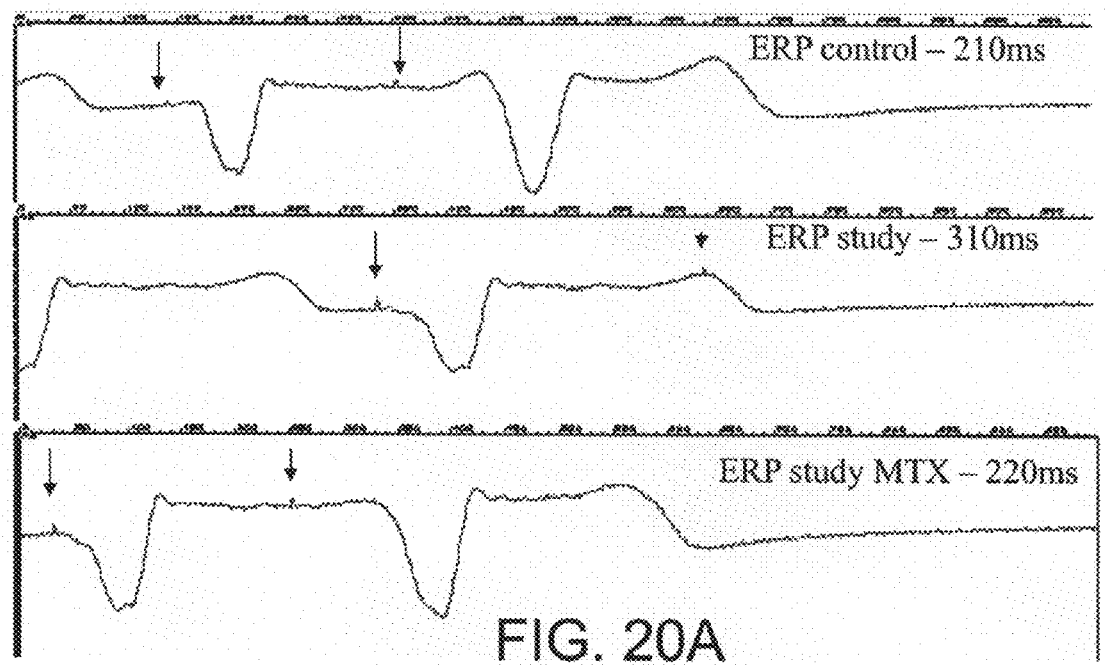
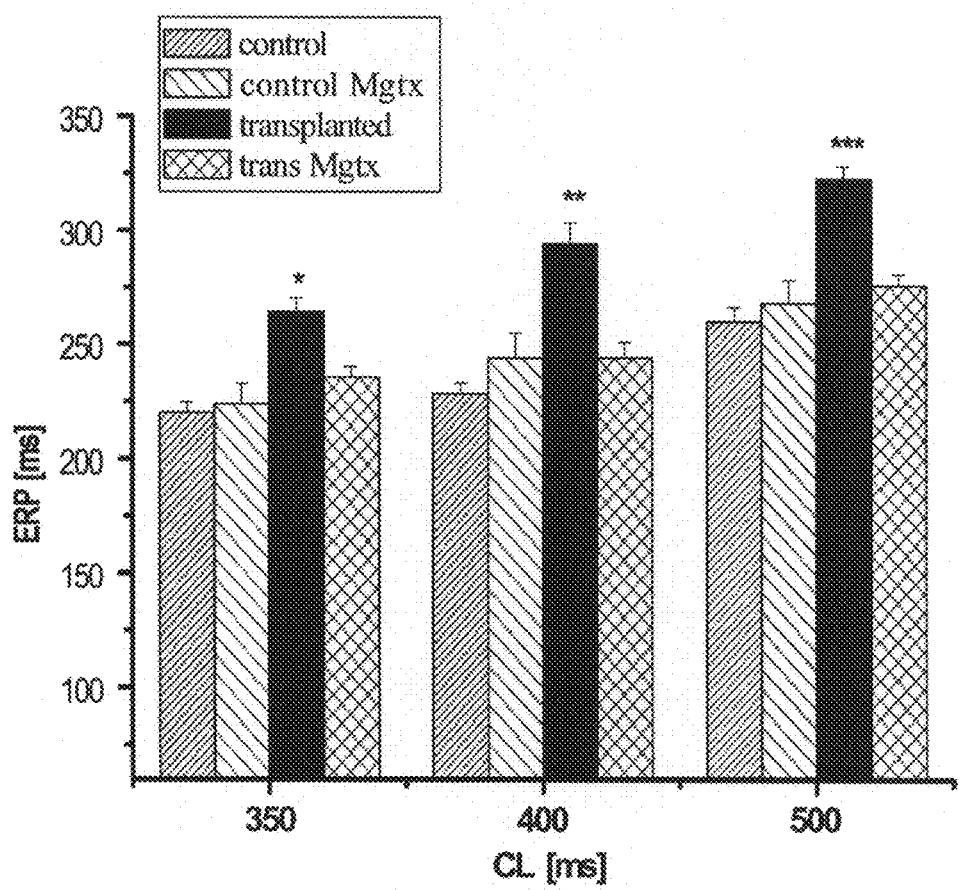
FIG. 20A
FIG. 20B

NUCLEIC ACID CONSTRUCTS AND CELLS, AND METHODS UTILIZING SAME FOR MODIFYING THE ELECTROPHYSIOLOGICAL FUNCTION OF EXCITABLE TISSUES

RELATED APPLICATIONS

This application is a continuation of U.S. patent application Ser. No. 10/919,343 filed on Aug. 17, 2004, which is a continuation-in-part of U.S. patent application Ser. No. 10/399,715, filed on Apr. 21, 2003, which is a national phase of PCT/IL01/00833, filed on Sep. 5, 2001, which is a continuation of U.S. patent application Ser. No. 09/691,889, filed on Oct. 20, 2000, now U.S. Pat. No. 7,294,333 issued on Nov. 13, 2007, the specifications of which are hereby incorporated by reference.

FIELD AND BACKGROUND OF THE INVENTION

The present invention relates to nucleic acid constructs and cells, and further to methods utilizing same for modifying the electrophysiological function of excitable tissues. More particularly, embodiments of the present invention relate to the use of cells having gap junctions and ion channels or transporters for modifying the electrophysiological function of excitable tissues.

The biological cell membrane, the interface between the cell and its environment, is a complex biochemical entity one of whose major involvement is the directed transport of specific substances. A related major involvement of the cell membrane is the maintenance of chemical gradients, particularly electrochemical gradients, across this interface. These gradients are of great functional significance (e.g., in the production of action potentials in nerve and muscle cells).

Ion channels are macromolecular protein pores, which span the cell membrane lipid bilayer. While approximately 30% of the energy expended in cells goes to maintain the ionic gradient across the cell membrane, it is the ion channel that dissipates this stored energy, much as a switch releases the electrical energy of a battery.

Ion channels are efficient compared to enzymes; small conformational changes gate a single channel between "closed" and "open" states, allowing up to $10^7$ ions to flow in one second, amounting to approximately $10^{-12}$ Amperes of highly selected ions flow during the channel opening. Since they are efficient, the number of ion channels per cell is relatively low; a few thousand channels of a given subtype/cell are usually sufficient to perform their task while orders of magnitude higher numbers of receptors or enzymes are required to carry out their tasks.

Ion channels are usually classified by the type of ion they selectively pass (sodium, potassium, calcium, or chloride) although some are indiscriminate. Different ion channels are activated (or gated) by either extracellular ligands, transmembrane voltage, or intracellular second messengers.

Ion Channel Conductance

Conductance quantifies the ease with which ions flow through a material and is expressed in units of charge/sec/volt. Single channel conductance, g, as distinguished from the membrane conductance (G) of the entire population of channels, is defined as the ratio of single channel current amplitude (i) to the electromotive force, or voltage (V):

$$g=i/V$$

The direction of ion movement through channels is governed by electrical and chemical concentration gradients. Entropy dictates that ions will flow passively through ion channels down a chemical gradient. Electrically charged ions will also move in an electrical field, just as ions in solution flow to one of the poles of a battery connected to the solution. The point at which the chemical driving force is just balanced by the electrical driving force is called the Nernst equilibrium (or reversal) potential. Above or below this point, a particular ion species will flow in the direction of the dominant force. The net electrical flow across a cell membrane is predictable given the concentrations of ions, the number, conductances, and selectivities of the channels, and their gating properties.

The modern method of deciphering ion channel function is by using patch clamp technology. In the patch clamp technique, a small polished electrode is pressed against the plasma membrane. For unknown reasons, the affinity between glass and cellular membrane is incredibly high; very few ions leak through this tight seal. In essence, the electrode isolates and captures all ions flowing through the 1-3 square microns of the cell membrane defined by the circular border of the glass pipette. The result is that the ionic current passing through a single ion channel can be collected and measured. The current through the attached patch (cell-attached), a detached patch (inside-out or outside-out), or the whole cell can be measured.

Ion Channel Building Blocks

Since ion channel function is easily measured in real time, most ion channels were cloned using the South African clawed toad (*Xenopus laevis*) oocyte. These oocytes are large enough to inject with exogenous mRNA and are capable of synthesizing the resulting foreign proteins. In expression cloning, in vitro transcripts (mRNA) from a cDNA library derived from a source of tissue/cell known to be rich in a particular current are injected into individual oocytes. The proteins encoded by this library are allowed several days to be translated and processed before the oocyte currents are measured by voltage clamp techniques. The cDNA library (with ~1 million unique clones) is serially subdivided until injected messenger RNA from a single cDNA clone is isolated that confers novel ion channel activity. Moreover, mutant cDNA clones with engineered alterations in the protein's primary structure can be expressed and the ion channel properties studied in order to determine regions of the protein critical for channel activation, inactivation, ion permeation, or drug interaction.

The building blocks for most channel proteins are individual polypeptide subunits or domains of subunits each containing six hydrophobic transmembrane regions labeled S1 through S6. The Na+ and Ca2+ channel pores are single (a) subunits in which 4 repeats of the six transmembrane spanning domain surround the pore. Voltage-gated K+ channels (Kv; nomenclature refers to K channel, voltage-dependent) are encoded by a tetramer of separate six-transmembrane spanning motifs. Coassembly of the linked domains form the central pore and confer the basic gating and permeation properties characteristic of the channel type. The peptide chain (H5 or P loop) juxtaposed between the membrane spanning segments S5 and S6 project into and line the water-filled channel pore. Mutations in this region alter the channel's permeation properties. S4 is probably the major channel voltage sensor since it contains a cluster of positively charged amino acids (lysines and arginines). Voltage-dependent channel inactivation is mediated by a tethered amino terminal blocking particle (called the ball and chain mechanism) which swings in to occlude the permeation pathway (inactivation). Amino acids in the S6 transmembrane segment participate in another inactivation pathway named C-type inactivation.

The most recently discovered family of channel proteins are the inward rectifier K+-selective channels (Kir; K channel, inward rectifier). These channels determine the resting membrane potential in most cells because they are open at rest. Kir channel topography is similar to the Kv channel class but the subunits lack the S1 to S4 segments present in Kv channels. The two transmembrane spanning domain surrounding the conserved H5 pore domain is deceptively simple; heteromultimeric channel formation, direct G protein gating, and interactions with other proteins by some Kir subtypes considerably increases the complex behavior of this channel class.

Ion Transporters:

Yet another class of molecules which participate in ion transport across cellular membranes are the ion transporters. Ion transporters are integral membrane proteins capable of pumping one ion out of the cell while pumping another ion into the cell.

In, for example, Na/K ion transporters, the Na+, K+ pump activity is the result of an integral membrane protein called the Na+, K+-ATPase. The Na+, K+-ATPase consists of a "catalytic" ☐subunit of about 100,000 daltons and a glycoprotein ☐subunit of about 50,000 daltons. When operating near its capacity for ion transport, the Na+, K+-ATPase transport three sodium ions out of the cell and transport two potassium ions into the cell for each ATP hydrolyzed. The cyclic phosphorylation and dephosphorylation of the protein causes it to alternate between two conformations, E1 and E2. In E1 the ion-binding sites of the protein have high affinity for Na+ and face the cytoplasm. In the E2 conformation the ion-binding sites favor the binding of K+ and face the extracellular fluid.

Examples of other ion transporters include the Na/Ca exchange system which participates in regulation of intracellular Ca+; the Na/H exchange system which function in concert with a Cl/HCO3 exchange system to regulate intracellular pH; and the Na—K—Cl exchange system which contributes to smooth muscle function and which is regulated by a number of vasoactive agents.

Excitable Tissues

Myocardium: Myocardial contraction depends on the opening and closing of a complex series of ion channels in myocardial cell membranes.

The most prominent of these channels are the K+ Ca++ and Na+ ion channels.

The number of K+ ions is greater inside a resting myocardial cell than outside. But the number of Na+ ions is greater outside. When a myocardial cell beats, sodium channels open allowing a rapid, transient in-rush of Na+ ions, then close within about two one-thousandth's (2/1000) of a second. This depolarizes the membrane with the positive ions moving in. Then there is then a slower, but prolonged (½ second), release of potassium to the outside of the cell which repolarizes the cell membrane.

Although myocardial contraction is more complex and involves other ions and channels, the end result of this depolarization-repolarization is that the contractile filaments in the cell engage, and the cell contracts.

Nerve cells: Signal propagation through neuronal cells is also governed by ion influx/outflux through nerve cell membranes. In nerve cells, Na+, Ca++ and K+ channels participate in the generation and propagation of a nerve signal.

Glandular tissue: Secretion of glandular factors, such as hormones is in some cases effected by the excitation of secreting cells or tissues. For example, in the pancreas, T-type calcium channels along with cell-to-cell gap junctions participate in secretion of insulin.

Since ion channels participate in numerous physiological processes, damage to cells and/or channels of excitable tissues can be a cause for numerous disorders.

For example, heart conditions, such as reentrant arrhythmia, are brought about by the damage or death of myocardial cells, which can no longer support normal electrophysiological function. Secretion of factors from glandular tissue, such as insulin is also effected by damage to excitable cells forming this tissue, while nerve cell changes, as for instance in disorders such as, epilepsy severely effects nerve signal function.

The present invention provides a novel approach for modifying the electrophysiological property and thus the electrophysiological function of excitable tissues.

This novel approach, which according to one embodiment of the present invention utilizes cellular implants, can be utilized for restoring normal electrophysiological function to damaged tissues such as heart, nerve or glandular tissues.

SUMMARY OF THE INVENTION

According to one aspect of the present invention there is provided a nucleic acid construct comprising: (a) a first polynucleotide region encoding at least one first polypeptide capable of forming a functional ion channel or transporter when expressed within a cell; and (b) a second polynucleotide region encoding at least one second polypeptide capable of forming a functional gap junction when expressed within the cell.

According to further features in preferred embodiments of the invention described below, the nucleic acid construct further comprising at least one promoter being for directing the transcription of the first polynucleotide and the second polynucleotide.

According to still further features in the described preferred embodiments the at least one promoter is functional in mammalian cells.

According to still further features in the described preferred embodiments the at least one promoter is selected from the group consisting of a constitutive promoter, a tissue specific promoter, an inducible promoter and a developmentally regulated promoter.

According to still further features in the described preferred embodiments the first polynucleotide region and the second polynucleotide region are transcriptionally fused via an IRES sequence.

According to still further features in the described preferred embodiments the at least one first polypeptide and the at least one second polypeptide are translationally fused via at least one protease recognition site.

According to still further features in the described preferred embodiments the at least one promoter includes two promoters, a first promoter for directing the transcription of the first polynucleotide and a second promoter for directing the transcription of the second polynucleotide.

According to another aspect of the present invention there is provided a nucleic acid construct system comprising: (a) a first nucleic acid construct including a first polynucleotide region encoding at least one first polypeptide capable of forming a functional ion channel or transporter when expressed within a cell; and (b) a second nucleic acid construct including a second polynucleotide region encoding at least one second polypeptide capable of forming a functional gap junction when expressed within the cell.

According to still further features in the described preferred embodiments the first nucleic acid construct further includes a first promoter being for directing the transcription of the first polynucleotide and further wherein the second nucleic acid construct further includes a second promoter being for directing the transcription of the second polynucleotide.

According to still further features in the described preferred embodiments each of the first and the second promoters is functional in mammalian cells.

According to still further features in the described preferred embodiments each of first and the second promoters is independently selected from the group consisting of a constitutive promoter, a tissue specific promoter, an inducible promoter and a developmentally regulated promoter.

According to still further features in the described preferred embodiments there is provided a cell, cell culture or tissue explant transformed with the nucleic acid constructs described above.

According to still further features in the described preferred embodiments the cell is selected from the group consisting of a fibroblast, a myoblast, an astroglial cell and an endothelial cell.

According to still further features in the described preferred embodiments the tissue explant is an organ tissue explant.

According to still further features in the described preferred embodiments there is provided a pharmaceutical composition comprising, as an active ingredient, the nucleic acid constructs described above.

According to still further features in the described preferred embodiments the ion channel is selected from the group consisting of a sodium ion channel, a potassium ion channel, a calcium ion channel and a chloride ion channel.

According to still further features in the described preferred embodiments the at least one first polypeptide is selected from the group consisting of a K channel polypeptide, a Na channel polypeptide, a Ca channel polypeptide, a Cl channel polypeptide, a Na/K transporter polypeptide, a Na/Ca transporter polypeptide, a Na/H transporter polypeptide and a Cl/HCO3 transporter polypeptide.

According to still further features in the described preferred embodiments the at least one second polypeptide is selected from the group consisting of connexin43, connexin45 and connexin26.

According to still another aspect of the present invention there is provided a method of modifying the electrophysiological function of an excitable tissue region of an individual, the method comprising the step of implanting cells into the excitable tissue region, each implanted cell being: (a) capable of forming gap junctions with at least one cell of the excitable tissue region; and (b) capable of forming a functional ion channel or transporter; the functional ion channel or transporter being capable of modifying the electrophysiological function of the excitable tissue region.

According to still further features in the described preferred embodiments the ion channel is selected from the group consisting of a sodium ion channel, a potassium ion channel, a calcium ion channel and a chloride ion channel.

According to still further features in the described preferred embodiments each implanted cell is transfected, prior to, or following implantation, with an exogenous polynucleotide expressing at least one polypeptide capable of forming the functional ion channel or transporter.

According to still further features in the described preferred embodiments each implanted cell is transformed, prior to, or following implantation, with an exogenous polynucleotide expressing at least one polypeptide capable of forming the gap junctions.

According to still further features in the described preferred embodiments expression of the at least one polypeptide from the exogenous polynucleotide is regulatable by an endogenous or an exogenous factor.

According to still further features in the described preferred embodiments an ion permeability of the functional ion channels is regulatable by an endogenous or an exogenous factor.

According to still further features in the described preferred embodiments the method further comprising the step of regulating the permeability of the functional ion channels, or the activity of the transporter to thereby regulate the electrophysiological function of the excitable tissue region.

According to still further features in the described preferred embodiments the step of regulating the permeability is affected by providing the exogenous factor to the excitable tissue region.

According to still further features in the described preferred embodiments each implanted cell is capable of forming the functional ion channel or transporter following induction.

According to still further features in the described preferred embodiments the excitable tissue region forms a part of an organ selected from the group consisting of a heart, a pancreas, a kidney, a brain and a liver.

According to still further features in the described preferred embodiments the method is utilized for regulating cardiac arrhythmia.

According to still further features in the described preferred embodiments the method is utilized for regulating secretion of endogenous factors from an organ including the excitable tissue region of the individual.

According to still further features in the described preferred embodiments the method is utilized for regulating neuronal discharge.

According to an additional aspect of the present invention there is provided a method of modifying the electrophysiological function of an excitable tissue region of an individual, the method comprising the step of expressing an exogenous polypeptide in at least a portion of cells forming a part of, or being in contact with, the excitable tissue region, the exogenous polypeptide being capable of forming functional ion channels or transporters within the at least a portion of the cells to thereby modify the electrophysiological function of the excitable tissue region.

According to still further features in the described preferred embodiments the method further comprising the step of expressing a second exogenous polypeptide in the at least a portion of the cells, the second exogenous polypeptide being capable of forming functional pap junctions within the at least a portion of the cells.

According to still an additional aspect of the present invention there is provided a population of cells suitable for treating a glucose regulation disorder in a subject, the population of cells comprising cells expressing at least one exogenous polypeptide forming: (i) a connexin channel; (ii) a depolarizing ion channel; and/or (iii) a non selective ion channel.

According to a further aspect of the present invention there is provided a population of cells suitable for treating cardiac arrhythmia in a subject, the population of cells comprising cells expressing at least one exogenous polypeptide forming: (i) a sodium channel; (ii) a calcium channel; (iii) a leak ion channel; and/or (iv) a non-selective ion channel.

According to yet a further aspect of the present invention there is provided a population of cells suitable for prolonging a refractory period of a cardiac tissue in a subject, the population of cells comprising cells expressing at least one exogenous polypeptide forming: (i) a connexin channel; (ii) a sodium channel; (iii) a potassium channel; and/or (iv) a chloride channel.

According to still a further aspect of the present invention there is provided a population of cells suitable for modulating neural excitability in a subject, the population of cells comprising cells expressing at least one exogenous polypeptide forming: (i) a connexin channel; and/or (ii) a depolarizing ion channel.

According to still a further aspect of the present invention there is provided a population of cells suitable for increasing neural excitability in a subject, the population of cells comprising cells expressing at least one exogenous polypeptide forming: (i) a hyperpolarizing ion channel; and/or (ii) connexin36.

According to still a further aspect of the present invention there is provided a population of cells suitable for increasing pyramidal or purkinje cell coupling in a subject, the population of cells comprising cells expressing at least one exogenous polypeptide forming: (i) connexin47; and/or (ii) a depolarizing ion channel.

According to still further features in the described preferred embodiments the subject suffers from cerebrovascular accident.

According to still a further aspect of the present invention there is provided a population of cells suitable for decreasing pyramidal or purkinje cell coupling in a subject, the population of cells comprising cells expressing at least one exogenous polypeptide forming: (i) connexin47; and/or (ii) a hyperpolarizing ion channel.

According to still further features in the described preferred embodiments the subject suffers from epilepsy and/or phantom pain.

According to still further features in the described preferred embodiments the hyperpolarizing ion channel is selected from the group consisting of a potassium channel and a chloride channel.

According to still a further aspect of the present invention there is provided a method of treating glucose regulation disorder in a subject, the method comprising administering to the subject a therapeutically effective amount of cells capable of electrical coupling with pancreatic β-islets, thereby treating the glucose regulation disorder in the subject.

According to still further features in the described preferred embodiments the cells are selected from the group consisting of mesenchymal stem cells, fibroblasts and embryonic stem cells.

According to still further features in the described preferred embodiments the cells express at least one exogenous polypeptide forming: (i) a connexin channel; (ii) a depolarizing ion channel; and/or (iii) a non-selective ion channel, thereby treating insulin-deficiency in a subject.

According to still a further aspect of the present invention there is provided a method of treating insulin-deficiency in a subject, the method comprising expressing at least one exogenous polypeptide in at least a subset of cells forming a part of, or being in contact with pancreatic β-cells, the at least one exogenous polypeptide forming: (i) a connexin channel; and/or (ii) a depolarizing ion channel, thereby treating the insulin-deficiency in the subject.

According to still further features in the described preferred embodiments expressing the at least one exogenous polypeptide in at least the subset of cells forming a part of, or being in contact with pancreatic β-cells is effected by systemic administration of at least one polynucleotide encoding the at least one exogenous polypeptide, the at least one exogenous polynucleotide being operably linked to a pancreatic functional promoter.

According to still further features in the described preferred embodiments expressing the at least one exogenous polypeptide in at least the subset of cells forming a part of, or being in contact with pancreatic β-cells is effected by localized administration of at least one polynucleotide encoding the at least one exogenous polypeptide.

According to still further features in the described preferred embodiments the depolarizing ion channel is selected from the group consisting of a sodium channel and a calcium channel and a non-selective ion channel.

According to still further features in the described preferred embodiments the sodium channel is an SCN channel.

According to still further features in the described preferred embodiments the calcium channel is selected from the group consisting of an L-type calcium channel, a T-type calcium channel and an N-type calcium channel.

According to still further features in the described preferred embodiments the non-selective ion channel is an HCN channel.

According to still further features in the described preferred embodiments connexin channel is selected from the group consisting of connexin36, connexin40, connexin43 and connexin 45.

According to still further features in the described preferred embodiments the subject suffers from type 2 diabetes mellitus.

According to still a further aspect of the present invention there is provided a method of treating cardiac arrhythmia in a subject, the method comprising administering to the subject a therapeutically effective amount of cells capable of electrical coupling a cardiac tissue of the subject, thereby treating the cardiac arrhythmia in the subject.

According to still further features in the described preferred embodiments the cells are selected from the group consisting of mesenchymal stem cells, fibroblasts, myoblasts and embryonic stem cells.

According to still further features in the described preferred embodiments the cells express at least one exogenous polypeptide forming: (i) a sodium channel; (ii) a calcium channel; (iii) a leak ion channel; and/or (iv) a non-selective ion channel.

According to still a further aspect of the present invention there is provided a method of treating cardiac arrhythmia in a subject, the method comprising expressing at least one exogenous polypeptide in at least a subset of cells forming a part of, or being in contact with cardiac tissue, the at least one exogenous polypeptide forming: (i) a sodium channel; (ii) a calcium channel; (iii) a leak ion channel; and/or (iv) a non-selective ion channel, thereby treating cardiac arrhythmia in a subject.

According to still further features in the described preferred embodiments the subject suffers from bradycardia and/or atrial fibrillation.

According to still further features in the described preferred embodiments expressing the at least one exogenous polypeptide in at least the subset of cells forming a part of, or being in contact with the cardiac tissue is effected by systemic administration of at least one polynucleotide encoding the at least one exogenous polypeptide, the at least one exogenous polynucleotide being operably linked to a cardiac functional promoter.

According to still further features in the described preferred embodiments expressing the at least one exogenous polypeptide in at least the subset of cells forming a part of, or being in contact with the cardiac tissue is effected by localized administration of at least one polynucleotide encoding the at least one exogenous polypeptide.

According to still a further aspect of the present invention there is provided a method of treating a disease treatable by increasing the refractory period of a cardiac tissue in a subject, the method comprising administering to the subject a therapeutically effective amount of cells capable of electrical coupling with a cardiac tissue of the subject, thereby treating the disease treatable by increasing the refractory period of a cardiac tissue in the subject.

According to still further features in the described preferred embodiments the cells are selected from the group consisting of myoblasts, fibroblasts, mesenchymal stem cells and embryonic stem cells.

According to still further features in the described preferred embodiments the cells express at least one exogenous polypeptide forming: (i) a connexin channel; (ii) a sodium channel; (iii) a potassium channel; and/or (iv) a chloride channel.

According to still further features in the described preferred embodiments administering to the subject is effected at a location selected from the group consisting of an AV node and an AV node area, AV nodal artery, specific coronary artery feeding an arrhythmogenic area, ventricles, atrias and anterior right atrial branch of right coronary artery.

According to still further features in the described preferred embodiments administration to the subject is effected by epicardial during surgery, trans-catheter injection to coronary artery using balloon catheter, or trans-catheter injection using injecting catheter.

According to still a further aspect of the present invention there is provided a method of treating a disease treatable by increasing the refractory period of a cardiac tissue in a subject, the method comprising expressing at least one exogenous polypeptide in at least a subset of cells forming a part of, or being in contact with a cardiac tissue of the subject, the at least one exogenous polypeptide forming: (i) a connexin channel; (ii) a sodium channel; (iii) a potassium channel; and/or (iv) a chloride channel, thereby treating the disease treatable by increasing the refractory period of the cardiac tissue in a subject.

According to still further features in the described preferred embodiments the disease is selected from the group consisting of atrial fibrillation, atrial flutter, atrial tachycardia and ventricular tachycardia.

According to still further features in the described preferred embodiments connexin channel is selected from the group consisting of connexin40, connexin43 and connexin45.

According to still further features in the described preferred embodiments the sodium channel is a mutated SCN5A channel.

According to still further features in the described preferred embodiments the SCN5A channel has a mutation selected from the group consisting of ΔKPQ, N1325S, R1644H, E1295K, D1790G and ins1795.

According to still further features in the described preferred embodiments the potassium channel is a voltage gated potassium channel or an inward rectifier channel.

According to still further features in the described preferred embodiments the voltage gated potassium channel is a Kv1.3 or a mutant thereof.

According to still further features in the described preferred embodiments the mutant of Kv1.3 is Kv1.3H401W.

According to still further features in the described preferred embodiments the inward rectifier channel is a KCNH channel.

According to still further features in the described preferred embodiments the KCNH channel is selected from the group consisting of Kir4.1, Kir7.1, Kir1.1, Kir2.1, Kir5.1, Kir6.1 and Kir8.1.

According to still further features in the described preferred embodiments expressing the at least one exogenous polypeptide in at least the subset of cells forming a part of, or being in contact with the cardiac tissue is effected by systemic administration of at least one polynucleotide encoding the at least one exogenous polypeptide, the at least one exogenous polynucleotide being operably linked to a cardiac functional promoter.

According to still further features in the described preferred embodiments expressing the at least one exogenous polypeptide in at least the subset of cells forming a part of, or being in contact with the cardiac tissue is effected by localized administration of at least one polynucleotide encoding the at least one exogenous polypeptide.

According to still further features in the described preferred embodiments the administering is effected at a location selected from the group consisting of an AV node and an AV node area, AV nodal artery, specific coronary artery feeding an arrhythmogenic area, ventricles, atrias and anterior right atrial branch of right coronary artery.

According to still a further aspect of the present invention there is provided a method of treating a disease treatable by modulating neural excitability in a subject, the method comprising administering to the subject a therapeutically effective amount of cells capable of electrical coupling with a neural tissue of the subject, thereby treating the disease treatable by modulating neural excitability in the subject.

According to still further features in the described preferred embodiments modulating neural excitability is decreasing neural excitability.

According to still further features in the described preferred embodiments the cells are selected from the group consisting of fibroblasts, microglia, oligodendrocytes, astroglia, mesenchymal stem cells and embryonic stem cells.

According to still further features in the described preferred embodiments the cells express at least one exogenous polypeptide forming: (i) a connexin channel; and/or (ii) a depolarizing ion channel; and/or (iii) a hyperpolarizing ion channel.

According to still further features in the described preferred embodiments the site is selected from the group consisting of an external globus pallidum, striatum, subthalamic nucleus, internal globus pallidus, nigra reticulate and zona increta.

According to still further features in the described preferred embodiments administering is effected using a delivery route selected from the group consisting of direct injection during a neurosurgery procedure and trans-catheter through neural arteries.

According to still a further aspect of the present invention there is provided a method of treating a disease treatable by modulating neural excitability in a subject, the method comprising expressing at least one exogenous polypeptide in at least a subset of cells forming a part of, or being in contact with a neural tissue of the subject, the at least one exogenous polypeptide forming: (i) a connexin channel; and/or (ii) a depolarizing ion channel, and/or (iii) a hyperpolarizing ion channel, thereby treating the disease treatable by decreasing neural excitability in the subject According to still further features in the described preferred embodiments the connexin channel is selected from the group consisting of connexin32, connexin36, connexin43 and connexin47.

According to still further features in the described preferred embodiments the disease is Parkinson's disease and/or epilepsy.

According to still further features in the described preferred embodiments expressing is effected at a site capable of generating an epileptic stimulus.

According to still further features in the described preferred embodiments the site is selected from the group consisting of an external globus pallidum, striatum, subthalamic nucleus, internal globus pallidus, nigra reticulate and zona increta.

According to still further features in the described preferred embodiments expressing the at least one exogenous polypeptide in at least the subset of cells forming a part of, or being in contact with the neural tissue is effected by systemic administration of at least one polynucleotide encoding the at least one exogenous polypeptide, the at least one exogenous polynucleotide being operably linked to a neural functional promoter.

According to still further features in the described preferred embodiments expressing the at least one exogenous polypeptide in at least the subset of cells forming a part of, or being in contact with the neural tissue is effected by localized administration of at least one polynucleotide encoding the at least one exogenous polypeptide.

According to still a further aspect of the present invention there is provided a method of treating a disease treatable by increasing neural excitability in a subject, the method comprising administering to the subject a therapeutically effective amount of cells expressing at least one exogenous polypeptide forming: (i) a hyperpolarizing ion channel; and/or (ii) connexin36, thereby treating the disease treatable by increasing neural excitability in the subject According to still further features in the described preferred embodiments the cells are selected from the group consisting of fibroblasts, microglia, oligodendrocytes, astroglia, mesenchymal stem cells, and embryonic stem cells.

According to still a further aspect of the present invention there is provided a method of treating a disease treatable by increasing neural excitability in a subject, the method comprising expressing at least one exogenous polypeptide in at least a subset of cells forming a part of, or being in contact with a neural tissue of the subject, the at least one exogenous polypeptide forming: (i) a hyperpolarizing ion channel; and/or (ii) connexin36, thereby treating the disease treatable by increasing neural excitability in the subject According to still further features in the described preferred embodiments the disease is a neurodegenerative disorder.

According to still further features in the described preferred embodiments the neurodegenerative disorder is Alzheimer's disease.

According to still further features in the described preferred embodiments the hyperpolarizing ion channel is a potassium channel or a chloride channel.

According to still further features in the described preferred embodiments the potassium channel is a Kv channel, a Kir channel, an acetylcholine receptor channel and a HERG channel.

According to still further features in the described preferred embodiments the chloride channel is a ClC channel.

According to still further features in the described preferred embodiments expressing the at least one exogenous polypeptide in at least the subset of cells forming a part of, or being in contact with the neural tissue is effected by systemic administration of at least one polynucleotide encoding the at least one exogenous polypeptide, the at least one exogenous polynucleotide being operably linked to a neural functional promoter.

According to still further features in the described preferred embodiments expressing the at least one exogenous polypeptide in at least the subset of cells forming a part of, or being in contact with the neural tissue is effected by localized administration of at least one polynucleotide encoding the at least one exogenous polypeptide.

According to still further features in the described preferred embodiments expressing is effected at a site selected from the group consisting of subthalamic nucleous, internal globus pallidum, zona increta, nigra reticulate, external globus pallidum and nuclei.

The present invention successfully addresses the shortcomings of the presently known configurations by providing a novel approach for modifying the electrophysiological function of excitable tissues.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1a-e illustrate results from experiments performed on large random cortical networks cultured on substrate-embedded multi-electrode arrays (MEA). FIG. 1a-b—an image illustrating four out of sixty electrodes and the somata of numerous neurons growing on the surface (1a) and a magnification of a region thereof (1b). In the magnified image (1b) the richness of the connective (axo-dendritic) network is evident. Scale bar: 30 μm. FIG. 1c—exemplifies an action potential recorded from one electrode. The two parallel lines represent ±8RMS units for this particular electrode. Network response to focal stimulation. FIGS. 1d-e illustrate a reverberating response of the network to focal stimuli. A typical stimulus pulse lasts 420 μSec, and its amplitude is 50 μA. The traces were recorded simultaneously from different electrodes. Note the reverberating response to a stimulus (enlarged in FIG. 1e) which lasts 100 milliseconds or more.

FIG. 4a illustrates a diffused fibroblast seeding pattern on multi electrode array (fibroblasts in red).

FIG. 4b illustrates a clustered fibroblast seeding pattern on multi electrode array.

FIG. 5 illustrates the CTX frequency response of cultured cardiomyocytes (square), cardiomyocytes co-cultured with fibroblasts NIH 3T3 (dot) and cardiomyocytes co-cultured with fibroblasts (NIH 3T3) transfected with voltage gated potassium channel Kv1.3 coding sequence (triangle). c-no. of cultures; n-no. of measurements (without fibroblast–c=8; n=16, NIH 3T3—c=6; n=47, Kv1.3—c=6; n=43, error bar—standard error).

FIG. 6a is a fluorescent image of a cardiomyocytes co-cultured with fibroblasts transfected with Kv1.3 channel coding sequences and labeled with Fast DiO (MAE cluster seeding pattern). The blue dot marks electrode 28 and the red dot marks electrode 53.

FIGS. 6b-c represent a two second recording of synchronous extracellular activity prior to seeding of the fibroblasts described in FIG. 6a. FIG. 6b—recording from electrode 28; FIG. 6c—recording from electrode 53;

FIGS. 6d-e represent a two second recording of uncoupled extracellular activity following seeding of the fibroblasts described in FIG. 6a and prior to treatment with CTX. FIG. 6d—recording from electrode 28; FIG. 6e—recording from electrode 53;

FIG. 6f-g represent a two second recording of extracellular activity following seeding of the fibroblasts described in FIG. 6a and treatment with CTX 100 nM which reverses uncoupling effect. FIG. 6f—recording from electrode 28; FIG. 6g—recording from electrode 53;

FIG. 7b illustrates an activation map constructed prior to seeding of the fibroblasts described in FIG. 7a.

FIG. 12a is a fluorescent image of MEA cultured cardiomyocytes and fibroblasts labeled with Fast DiO (cluster seeding pattern).

FIG. 12b illustrates an activation map constructed prior to seeding of the fibroblasts described in FIG. 12a.

FIG. 12c illustrates an activation map constructed five days following seeding of the fibroblasts described in FIG. 12a and prior to treatment with CTX, no conduction block is apparent.

FIG. 12d illustrates an activation map constructed five days following seeding of the fibroblasts described in FIG. 12a and following treatment with CTX (10 nM); no appreciable change from the activation map of FIG. 12c is evident.

FIGS. 20a-b depict changes in LV ERP of pigs grafted with naïve or fibroblasts transfected to express the voltage sensitive potassium channel Kv1.3 channel. FIG. 20a—note the middle trace, where the stimulus fails to activate the ventricle. Following the administration of Margatoxin, the ERP decreased to a near baseline value. FIG. 20b summarizes the changes in the ventricular ERP in the swine model. Black bar—ERP 7 days after transplantation of Kv1.3 expressing cell. Note the significant increase in ERP in comparison to the control area and the decrease to near baseline values after the administration of Margatoxin.

FIG. 21a shows immunostaining of the transplanted area in the rat myocardium. The grafted cells were labeled before transplantation with the fluorescent cell tracker CFDA (green). Note the presence of the grafted cells (green stained cells) along the needle track. Host cardiomyocytes can be identified by the positive staining with anti-cardiac troponin I antibodies (red cells). Cell nuclei were counterstained with ToPro3 (blue). FIG. 21b shows immunostaining of connexin 43 (green punctuate staining) showing the development of gap junctions (arrows) between host cardiomyocytes (red cells, positively stained with anti-cardiac troponin I antibodies) and the grafted fibroblasts (which were labeled with DAPI before transplantation and can be identified by their blue labeled nuclei).

DESCRIPTION OF THE PREFERRED EMBODIMENTS

Figure 1E:
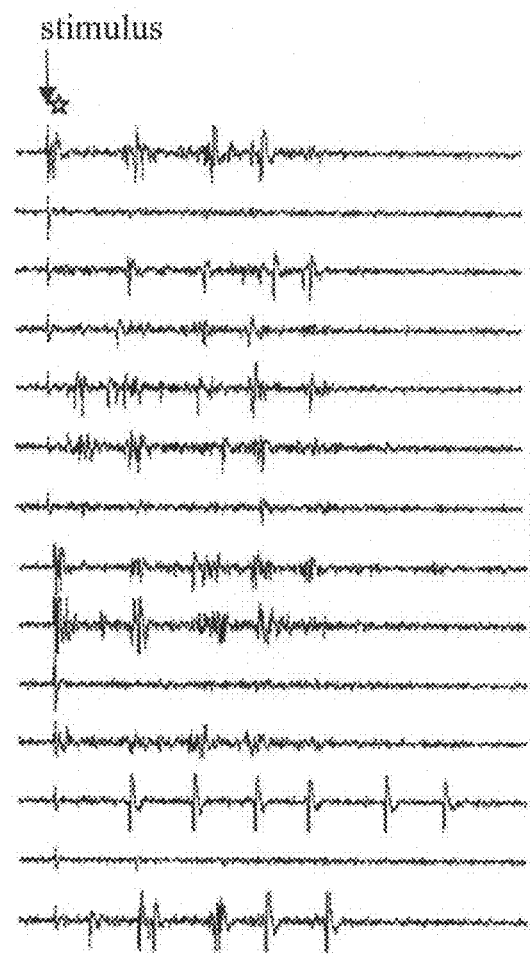
Figure 1F:
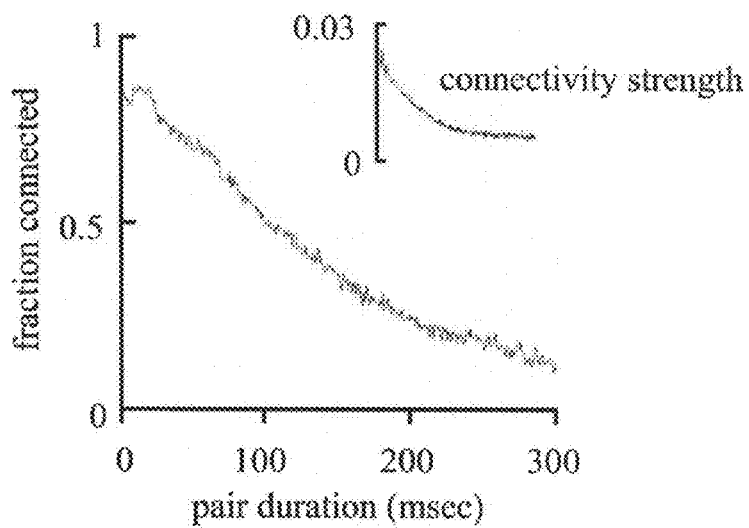
FIG. 1f is a graph illustrating the connectivity in cultured networks. The average number (four networks) of significantly occurring activity pairs formed between ten randomly chosen active (>0.2 Hz of spontaneous activity) electrodes. This number, normalized to the maximal number of possible activity pairs, is depicted as fraction connected, and shown to decrease as a function of within-pair time delay (δ). Inset: Given an A→B activity pair, the forecasting of B by A, which is the strength of the functional connectivity between the two, is given in terms of a correlation coefficient. This correlation is calculated from the number of times that the given pair appears within 1 hour, divided by the number of occurrences of A OR B. The average (n=4) functional connectivity strength as a function of 6 is shown.

The present invention is of nucleic acid constructs and cells, and of methods utilizing same for modifying the electrophysiological function of excitable tissues. Specifically, the present invention can be used to restore normal electrophysiological function to cells or tissues of, for example, damaged myocardium, neurons and secretory glands.

The principles and operation of the present invention may be better understood with reference to the accompanying descriptions.

Before explaining at least one embodiment of the invention in detail, it is to be understood that the invention is not limited in its application to the details of construction and the arrangement of the components set forth in the following description. The invention is capable of other embodiments or of being practiced or carried out in various ways. Also, it is to be understood that the phraseology and terminology employed herein is for the purpose of description and should not be regarded as limiting.

Since electrophysiological function of excitable tissues is governed by the quantity and type of ion channels present in the membrane of cells forming the excitable tissue, as well as the presence of gap junctions networking these cells, the present inventors propose that the electrophysiological function of any excitable tissue region can be modified by either expressing ion channel/transporter polypeptide(s) and/or gap junction polypeptide(s) within cells forming a part of, or being in contact with, the excitable tissue region; and/or by implanting cells (transformed or non-transformed) which are capable of electrical coupling with the excitable tissue.

As used herein, the phrase "excitable tissue" refers to tissue which is composed, at least in part, of cells which respond to, or propagate, an electrochemical change. Examples include muscle tissue, neuronal tissue and glandular tissue.

As used herein the phrase "cells capable of electrical coupling" refers to cells which are capable of causing voltage change in cells of the excitable tissues. Electrical coupling is usually achieved by gap junctions or electrical synapses although other mechanisms are also envisaged (e.g., fusion of grafted cell with host cell, and ion concentration changes). Electrical coupling is typically tested by impaling both cells with microelectrodes, injecting a current into one, and looking for a change in potential in the other.

Examples of cells which are capable of electrical coupling with the excitable tissues include non-transformed cells such as those listed in Examples 7-9 of the Examples section and transformed cells which express ion channels (ligand, voltage or drug-gated ion channels), transporters and/or gap junctions as further described hereinbelow and in the Examples section which follows.

According to the present invention, the introduction of new channels or channel producing cells into an excitable tissue, as well as the regulation of channel formation or permeability via endogenous or exogenous factors, can be utilized to control the electrophysiological function of excitable tissue to thereby treat various disorders associated with such tissues.

Thus, according to one aspect of the present invention, there is provided a nucleic acid construct including a first polynucleotide region encoding at least one first polypeptide which is capable of forming a functional ion channel or transporter when expressed within a cell, and a second polynucleotide region encoding at least one second polypeptide capable of forming a functional gap junction when expressed within the cell.

According to a preferred embodiment of the present invention, the first polynucleotide region encodes an ion channel forming polypeptide or polypeptides, such as, but not limited to, a Ca, K, Na or Cl ion channel forming polypeptide(s). For example, the first polynucleotide region can include the sequence set forth by nucleotides 179-6121 of Genbank Accession number AB027567, which when expressed within the cell produces a Na channel.

Additional examples of sequences which can be utilized by the present invention for forming a functional ion channel, when expressed within the cell, are listed according to their GenBank accession numbers in Tables 1-3 of the Example section which follows and in Examples 7-9 of the Examples section which follows.

The first polynucleotide region can also encode any modified polypeptide (e.g. mutated, chimeric etc') which is capable of forming functional ion channel in cells. Examples of mutated ion channel forming sequences are given in the Examples section which follows.

It will be appreciated that ion transporters such as Na/K, Na/Ca or Cl/HCO3 exchange systems (ATPases) can also be utilized by the present invention. Since such transporters are typically slower than channels in transporting ions across cell membranes, their use is limited to cases where rapid influx or outflux of ions is not required.

According to another preferred embodiment of the present invention, the gap junction forming polypeptide encoded by the second polynucleotide region is Connexin43 or 45, other connexin types which can be utilized by the present invention are described in the Examples section which follows.

The nucleic acid construct according to this aspect of the present invention also includes at least one promoter sequence for driving the transcription of the first and second polynucleotide regions. Preferably, the nucleic acid construct includes two promoters each driving transcription of a specific polynucleotide region. Alternatively, a single promoter sequence can transcribe both polynucleotide regions as a polycistronic message. Such a polycistronic message can include an internal ribosome entry site (IRES) between the first and second polynucleotide regions so as to enable the translation of the downstream polynucleotide region. Alternatively, the first and second polynucleotide regions of the polycistronic message can be translationally fused via a protease recognition site, such that a polypeptide translated from this message is cleaved into the first and second polypeptides described above.

It will be appreciated that although expressing both polynucleotide regions from a single construct is advantageous in some respects, each of the polynucleotide regions can alternatively be provided on a separate construct.

Thus, according to another aspect of the present invention there is provided a nucleic acid construct system which includes a first nucleic acid construct including a first polynucleotide region encoding at least one first polypeptide capable of forming a functional ion channel or transporter when expressed within a cell and a second nucleic acid construct including a second polynucleotide region encoding at least one second polypeptide capable of forming a functional gap junction when expressed within the cell.

The nucleic acid constructs of the present invention are utilized to transform cells, preferably mammalian cells, either in-vivo or ex-vivo.

As such the promoters utilized by these construct are mammalian functional promoters which are either constitutive, tissue specific, inducible or growth regulatable depending on the cell type and application.

The nucleic acid constructs described hereinabove are preferably constructed using commercially available mammalian expression vectors or derivatives thereof. Examples of suitable vectors include, but are not limited to, pcDNA3, pcDNA3.1(+/−), pZeoSV2(+/−), pSecTag2, pDisplay, pEF/myc/cyto, pCMV/myc/cyto, pCR3.1, which are available from Invitrogen, pCI which is available from Promega, pBK-RSV and pBK-CMV which are available from Stratagene, pTRES which is available from Clontech, and their derivatives and modificants.

Any of the promoter and/or regulatory sequences included in the mammalian expression vectors described above can be utilized to direct the transcription of the polynucleotide regions described above. However, since such vectors are readily amenable to sequence modifications via standard recombinant techniques, additional regulatory elements, promoter and/or selection markers can easily be incorporated therein if needed.

The nucleic acid constructs of the present invention can be introduced into a cell, population of cells, or tissue via any standard in-vivo or ex-vivo mammalian transformation method such as, biochemical methods, including but not limited to calcium-phosphate-mediated transformation, diethylaminoethyl (DEAE)-dextran-mediated transformation, cationic lipid-mediated (liposome) transformation, polybrene mediated transformation; physical methods such as, electroporation, direct micro-injection and biolistic particle delivery; and biological methods such as by using viruses (for further detail see, for example, "Methods in Enzymology" Vol. 1-317, Academic Press).

The cells or constructs according to the present invention can be administered to the individual per se, or in a pharmaceutical composition where it is mixed with suitable carriers or excipients.

Thus, according to another preferred embodiment of the present invention, the nucleic acid constructs according to the teachings of the present invention are included in a pharmaceutical composition which also includes a pharmaceutically acceptable carrier which serves for stabilizing and/or enhancing the accessibility or targeting of the constructs to target tissues.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the preparation accountable for the biological effect, i.e. the nucleic acid constructs of the present invention.

Hereinafter, the phrases "physiologically acceptable carrier" and "pharmaceutically acceptable carrier" are interchangeably used to refer to a carrier, such as, for example, a liposome, a virus, a micelle, or a protein, or a dilutent which do not cause significant irritation to an organism and do not abrogate the biological activity and properties of the active ingredient. An adjuvant is included under these phrases.

Herein the term "excipient" refers to an inert substance added to a pharmaceutical composition to further facilitate administration of an active ingredient. Examples, without limitation, of excipients, include calcium carbonate, calcium phosphate, various sugars and types of starch, cellulose derivatives, gelatin, vegetable oils and polyethylene glycols.

Techniques for formulation and administration of compositions may be found in "Remington's Pharmaceutical Sciences," Mack Publishing Co., Easton, Pa., latest edition, which is incorporated herein by reference.

Suitable routes of administration are preferably local rather than systemic, for example, via injection of the preparation directly into the excitable tissue region. Systemic administration is typically limited to the constructs of the present invention and is preferably effected while using tissue specific promoters, as described hereinabove. Specific routes for local and systemic administration as well as transplantation techniques (e.g., CT guided) are listed in Examples 7-9 of the Examples section which follows.

For injection, the active ingredients of the invention may be formulated in aqueous solutions, preferably in physiologically compatible buffers such as Hank's solution, Ringer's solution, or physiological salt buffer.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically.

Pharmaceutical compositions suitable for use in context of the present invention include compositions wherein the active ingredients are contained in an amount effective to achieve the intended purpose.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer of the active ingredient. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed. (See e.g., Fingl, et al., 1975, in "The Pharmacological Basis of Therapeutics", Ch. 1 p. 1).

Direct administration of the nucleic acid constructs described hereinabove or of pharmaceutical compositions including such constructs into cells forming a part of, or being in contact with, the excitable tissue region is preferably used in cases where the cells of the excitable tissue to be transformed are viable and functional.

In cases where cell damage or death defines a disorder of excitable tissue, the preferred mode of treatment is implantation of transformed or non-transformed cells having ion channels/transporters and gap junctions.

Thus, according to another aspect of the present invention there is provided a method of modifying the electrophysiological function of an excitable tissue region of an individual. The method is effected by implanting cells into the excitable tissue region, wherein the implanted cells are each characterized by the ability to form gap junctions with at least one cell of the excitable tissue region and by the ability to form functional ion channels or transporters of one or more channel or transporter types.

Implantation of such cells can be effected by, for example, a syringe and needle adapted or fabricated for cell implantation, by a catheter drug delivery system (see for example, U.S. Pat. No. 6,102,887) or by standard neurosurgical methods.

As mentioned above, the implanted cells can be cells expressing endogenous ion channel and/or gap junction polypeptides, or modified cells transformed with the nucleic acid constructs of the present invention. Preferably, the implanted cells are mammalian cells, such as for example, muscle, or fibers cells (see the Examples section for further detail).

In any case, the cells and ion channel selectivity and gating-regulation types are selected according to the application. For example, in application where rapid channel gating is crucial, an ion channel of regulatable gating is selected. Gating Regulated channels, and factors utilizable for regulating gating are described in the examples section hereinbelow.

In addition, regulation of ion channel/transporter polypeptide expression through, for example, induced promoter activity or the like can also be effected as an alternative or additive regulatory mechanism for controlling ion influx or outflux.

Thus, the present invention provides a novel approach for modifying the electrophysiological function of excitable tissues. As is further detailed in the Examples section which follows, the present invention can be utilized to restore enhance or suppress electrophysiological function across a tissue region thereby treating diseases caused by dysfunction in, or damage to, excitable tissues.

As used herein the term "treating" refers to inhibiting or arresting the development of a disease, disorder or condition and/or causing the reduction, remission, or regression of a disease, disorder or condition in a subject suffering from, being predisposed to, or diagnosed with, the disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

Examples of diseases and conditions which can be treated using the constructs and/or cells of the present invention include, but are not limited to glucose regulation disorders (e.g., diabetes mellitus), cardiac arrythmia (e.g., bradycardia, atrial fibrillation) diseases which are treatable by modulating (i.e., increasing or decreasing) the refractory period of a cardiac tissue (e.g., atrial fibrillation, atrial flutter, atrial tachycardia and ventricular tachycardia), diseases which are treatable by modulating (i.e., increasing or decreasing) neural excitability (e.g., epilepsy, Parkinson's disease and Alzheimer's disease) and diseases and conditions which are treatable by modulating (i.e., increasing or decreasing) pyramidal or purkinje cell coupling (e.g., cerebrovascular accident, epilepsy and pain (e.g., phantom pain).

Cells and/or constructs of the present invention can be included in a diagnostic or therapeutic kit. For example, cells suitable for treating glucose regulation disorder in a subject, can be packaged in a container with appropriate buffers and preservatives and used for therapy.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, cellular and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Cardiac Applications

Cardiac arrhythmias are rhythm disturbances that result from alteration of the electrophysiological substrate of the heart. These arrhythmias include bradyarrhythmias (slow heart rate) which result from abnormalities in impulse formation or conduction and tachyarrhythmias (high heart rate) which result from abnormalities in the electrophysiological substrate and which lead to the formation of tachycardia via abnormal foci firing at high rate or via formation of reentry circuits.

Cardiac arrhythmia often results from damage to the electrophysiological tissue substrate of the heart. By transplanting cells transfected with various ionic channels of specific and predetermined properties, the methods of the present invention enable one to modify the electrophysiological properties of heart tissue and thus repair such arrhythmias. Thus, the present invention can be used to either increase excitability to treat bradyarrhythmias or modify the electrophysiological substrate in order to suppress or prevent tachyarrhythmias.

Numerous cell types can be utilized to accomplish such a task, provided the cells posses functional gap junctions and functional ion channels.

Examples of suitable cell types include, but are not limited to, fibroblasts, skeletal myoblasts (satellite cells), endothelial cells and the like which can be of autogenic, allogenic, or xenogenic origin.

The cells transplanted generate specific structural and function interactions with the cardiomyocytes via the gap junction which can be either inherent to the transplanted cells or the product of overexpressed exogenes (listed in Table 1 below).

TABLE 1

Sequences encoding polypeptide constituents of various ion channels

| Ion | Channel type | GenBank Accession numbers | Potential application |
|---|---|---|---|
| K | Kv1.3 | H18261 | Reentrant arrhythmia, Atrial fibrillation, Ventricular and atrial tachycardia or heart failure |
| K | inward rectifier potassium channel TWIK-1 - human | S65566 | Atrial fibrillation or heart failure |
| K | Delayed rectifier potassium channel - human | L28168 L33815 M26685 | Atrial fibrillation or heart failure |
| K | Cardiac inward rectifier potassium channel - human | I38727 | Atrial fibrillation or heart failure |
| K | VOLTAGE-GATED POTASSIUM CHANNEL PROTEIN KV1.4 | M55514 AI631014 AI701825 AI694934 AI793138 | Atrial fibrillation or heart failure |
| K | 'voltage-gated potassium channel protein - human' | JC5275 | Atrial fibrillation or heart failure |
| K | ÒKCNQ2"; potassium channel | AF033348 | Atrial fibrillation or heart failure |
| K | 'inwardly rectifying potassium channel, hippocampal | I38521 | Reentrant arrhythmia, Atrial fibrillation, Ventricular and atrial tachycardia or heart failure |
| K | VOLTAGE-GATED POTASSIUM CHANNEL PROTEIN KQT- -LIKE 3.KCNQ3. | AF033347 AF071491 AW205596 AW135705 AA019129 AA001392 H86059 H08544 R36327 T78692 AI125802 H08545 R49258 | Atrial fibrillation or heart failure |
| Na | Sodium channel | AB027567 | A-V block, Atrial fibrillation, Sick sinus syndrome |

TABLE 1-continued

Sequences encoding polypeptide constituents of various ion channels

| Ion | Channel type | GenBank Accession numbers | Potential application |
|-----|--------------|---------------------------|----------------------|
| Na | Voltage gated "SCN11A" | AF188679 | A-V block, Atrial fibrillation, Sick sinus syndrome |
| Na | 'AMILORIDE-SENSITIVE BRAIN SODIUM CHANNEL BNAC1' | U57352 U50352 H12215 Z45660 R35720 R15377 AA457638 AI473139 H12216 AI825456 R49357 T16341 F04549 R42118 | A-V block, Atrial fibrillation, Sick sinus syndrome |
| Na | hBNaC2"; product: "sodium channel 2 | U78181 AL035862 AA442069 AI017398 AI620655 AI762424 Z40887 AI700050 | A-V block, Atrial fibrillation, Sick sinus syndrome |
| Ca | T-type | AF134986 | Heart failure |
| Ca | 'VOLTAGE-DEPENDENT N-TYPE CALCIUM CHANNEL' | M94172 U76666 AA776162 T12610 | Heart failure |
| Ca | "L-type calcium channel (HFCC)"; Human' | M92269 AA927640 AA443875 AA173146 | Heart failure |
| Ca | "CACNG4"; product: "calcium channel' | AF142625 | Heart failure |
| Ca | 'VOLTAGE-DEPENDENT L-TYPE CALCIUM CHANNEL,' | AJ224874 AJ006216 | Heart failure |
| Ca | "voltage-dependent calcium channel' | M92301 W07059 T28094 | Heart failure |
| Ca | L-type | M76558 AF055575 H29339 R25307 T27949 AA885750 AW029633 AI955764 AW008794 AA978315 AI914244 AI951788 AW008769 H29256 AI963788 AI537488 AA468565 AA523647 AI361691 R46658 AW139850 AI017959 AA701888 AA703120 AA877582 | Heart failure |
| Cl | 'probable chloride channel ClC-6 - human' | S68428 | |
| Cl | "CLCN3"; product: "chloride channel protein' | AF029346 | |
| Cl | "ClC-2"; product: "chloride channel' | AF026004 | |
| Cl | "clc4"; product: "chloride channel' | AB019432 | |

The coupling between the transplanted and host cells forms a single functional unit. Such functional coupling of the transplanted cells with the myocytic tissue allows modification of the various action potential phases of the myocytes.

Listed below are some of the action potential modifications, which can be effected using the methods of the present invention.

(i) Transplantation of fibroblasts having potassium channels (KV1-3,É) can be utilized to reduce automaticity; the effect may be reversed by specific antagonist (e.g., Charybdotoxin)

(ii) Transplantation of fibroblasts having potassium channels (KV1-3, É) can also be utilized for the creation of block which can be reversed with CTX.

(iii) Transplantation of fibroblasts having sodium channels can be utilized for the creation of rate dependent conduction block. Na channels will be inactivated at fast (abnormal) rates but permit conduction at slower (physiological) rates.

(iv) Transplantation of cells having various channels (for example the human ether-a-go-go-related gene, HERG) can be used to repress abnormal focal activity (due to triggered activity and unstable repolarization).

(v) Transplantation of cells having KV channels can be utilized to regulate A-V node conduction (e.g., prolong refractoriness, or decrease conduction velocity).

(vi) Transplantation of cells having Na-channels or Na and K channels can be utilized to increase A-V node conduction.

(vii) Transplantation of cells having Na-channels can be utilized to increase excitability by increasing spontaneous rate and conduction within the SA node (pacemaker).

Transplantation Patterns

The ability to transplant the cellular grafts of the present invention at predetermined myocardial sites may be of unique advantage since the location of the transplantation site can be selected and optimized according to the specific mechanism of the arrhythmia treated.

For example, a local effect may decrease side effects which result from a more generalized effect, as occurs for example, during pharmacological treatments.

A focal transplantation pattern may be used to treat focal arrhythmia or change excitability at predetermined sites. Linear lesion transplantation may be utilized to generate conduction blocks for the treatment of specific reentrant arrhythmia while diffuse transplantation patterns may be utilized to modify the excitable properties of entire regions.

Methods of Transplantation

Several transplantation approaches can be utilized by the present invention. For example, an epicardial transplantation can be effected via surgical procedures, while an endocardial transplantation can be effected via catheters that are employed percutaneously and may be used to inject the cells endocardially. Alternatively, the cells may be injected into the coronary circulation.

Specific Applications

Atrial fibrillation (AF): In atrial fibrillation, the normal rhythmical contractions of the cardiac atria are replaced by rapid irregular twitchings of the muscular wall; the ventricles respond in an irregular and rapid manner to the dysrhythmic bombardment from the atria. The pathological properties of AF can be modified using the teachings of the present invention via one of several possible approaches:

Cells transfected with specific ionic channel coding sequences, for example the voltage gated potassium channels (Kv1.3), can be transplanted into the A-V node. The modulating effect on the A-V node will slow the ventricular rate. This effect may be further modulated by dose-related changes resulting from the application of a blocking factor such as, for example, charybdotoxin.

The present invention also enables to treat AF by creating multiple line blocks (similar to the surgical maze procedure or the equivalent ablation procedure) in both atria. These blocks can be created by transplanting cells having K channels or rate dependent Na channels in the desired predetermined pattern.

The methods of the present invention cells may also be utilized to suppress pulmonary vein foci which often trigger AF, or to prevent their propagation to the atria by creating conduction blocks. By modifying the electrophysiological substrate of the atria the methods of the present invention can be used to increase cellular coupling and to increase and homogenize repolarization.

Atrial flutter and other Macroreentrant atrial arrhythmia: These arrhythmias result from macroreentrant wavefronts which can be treated by transplanting the cells to create a block at a critical area (for example the tricuspid-IVC isthmus in typical flutter).

Atrial tachycardia: Paroxysmal tachycardia originating in an ectopic focus in the atrium can be treated by cells transplanted at the area of the ectopic foci which suppress the abnormal activity.

Ventricular and reentrant tachycardia: The methods of the present invention can also be utilized to treat paroxysmal tachycardia originating in an ectopic focus in the ventricle by transplanting cells at the area of the ectopic foci. In addition, reentrant tachycardia originating from a scar tissue, following myocardial infarction is also treatable via the methods of the present invention. In this case, cellular grafts can be used to modify (increase or decrease) the conduction properties of slow conduction pathways within the scar which are critical for initiation and sustainment of the reentrant arrhythmia.

A-V block: An impairment of the normal conduction between atria and ventricles can be treated by cellular graft which improve the excitability properties of the A-V node thus reversing the conduction block.

Sick-sinus syndrome: An abnormal function of the SA node (normal pace maker) which results in a slow heart rate or alternating slow-fast rates can be treated by cells transplanted in the SA Node area in order to increase the excitability of the SA Node, or by creating an alternative pacemaker by transplanting cells with pace maker properties (combination of Na and K channels).

Heart failure: despite considerable advances in the diagnosis and treatment, congestive heart failure is the only major cardiovascular disorder which is increasing in incidence. Ventricular arrhythmias account for approximately 50% of the moralities associated with congestive heart failure. Ventricular arrhythmias typically arise from prolongation of the action potential duration (APD) which results in unstable repolarization and thus generation of arrhythmias. Treatment in these cases can be effected by shortening the action potential or by synchronizing repolarization. This can be achieved by transplanting cells having potassium channels (e.g. delayed rectifier or ether-go-go) which would function in shortening the cardiomyocytic APD.

Heart failure can also be treated by transplantation of cells having L-type or T-type calcium channels into the ventricles in a diffuse or a predetermined pattern in order to increase the excitability of the ventricles and to modulate calcium ion kinetics in the host myocardial tissue. Such transplantation would improve the contractility and relaxation pattern of the ventricles and thus change the systolic and diastolic properties of the ventricle.

Long OT syndrome: patients with genetic or acquired abnormalities in repolarization which display prolonged QT intervals may suffer from life-threatening malignant arrhythmias such as polymorphic VT. Such patients may be treated with the cellular grafts of the present invention having ion channels, such as potassium channels, which are selected capable of shortening and homogenizing repolarization.

Example 2

Pancreas

Diabetes Mellitus is a metabolic disease in which carbohydrate utilization is reduced while utilization of lipid and protein enhanced. Diabetes Mellitus is caused by relative deficiency of insulin, and is characterized, in more severe cases, by chronic hyperglycemia, glycosuria, water and electrolyte loss, and various organ damage causing significant morbidity and mortality.

Gap junctions and junction-mediated cell-to-cell communications are obligatory features of gland cells, regardless of their secretory products. Studies on pancreatic islets and acinar cells indicate that cell-to-cell communication via gap junction channels is required for proper biosynthesis, storage and release of both insulin and amylase. However, the endocrine and exocrine portions of the pancreas show opposite connexin (Cx) and coupling changes in relation to the activation and inhibition of their secretory functions. These differences may be accounted for by the expression of connexin43 (Cx43) in pancreatic islets and of Cx26 and Cx32 in pancreatic acini. This alternative expression of connexin isoforms is also found in several other endocrine and exocrine glands. These observations indicate that connexin-made channels play a central role in the control of secretory events (Meda, 1996, Clinical & Experimental Pharmacology & Physiology, December; 23(12):1053-7).

The function of T-type voltage-gated calcium channels in insulin-secreting cells has been previously described (Bhattacharjee et al, 1997 Endocrinology, September 138(9):3735-40). Whole-cell voltage and current recordings, capacitance measurements, and RIA techniques were used to determine the contribution of T-type calcium channels in modulation of electrical activity and in stimulus-secretion coupling in a rat insulin secreting cell line, INS-1. Studies employing double pulse protocols in the current-clamp mode, uncovered that activation of T-type calcium channels provided a low threshold depolarizing potential that decreased the latency of onset of action potentials and increased the frequency of action potentials, both of which are abolished by administration of nickel chloride ($NiCl_2$), a selective T-type calcium channel blocker (Bhattacharjee et al, 1997 Endocrinology, September 138(9):3735-40).

Currently, treatment of non insulin dependent diabetes mellitus (NIDDM) includes, in more severe cases, drug therapy and insulin injections. The sulfonylureas family acts as ATP-sensitive potassium channels blockers, thus causing depolarization of the pancreatic b cells, calcium influx and insulin secretion.

Cellular grafts capable of forming gap junction (e.g. expressing Cx43) with pancreatic beta cells can be used by the present invention to treat NIDDM. These cells which can be of autogeneic, allogeneic or xenogeneic origin can be, for example, transfected ex-vivo with nucleic acid construct encoding a specific ion channel polypeptide(s), such as, for example, CACNA1G (encoded by GenBank Accession number AF134986) which forms a T-type voltage gated calcium channel (see Table 2 below for additional examples). The cells will be transplanted in the pancreas in a diffuse or a predetermined pattern via invasive or minimally invasive techniques. For example, minimally invasive percutaneous procedures using image guiding (CT, US etc.) can be used for transplantation of the cellular grafts.

Upon gap junction establishment, the cellular grafts will form a single compartment with the surrounding tissue and will increase the sensitivity of the pancreatic b cells to glucose levels by increasing the depolarization process and the sensitivity of insulin secretion to depolarization. For example, by using cells transfected with the T-type voltage gated calcium channels one may increase the ca influx following depolarization of the pancreatic cells thereby increasing insulin secretion.

Pharmacological blockage of these channels at a fine tuned dosage will prevent spontaneous action potentials thus preventing hypoglycemic states. This approach is advantageous since it allows to monitor insulin secretion regardless of the time of drug administration.

Several approaches can be utilized for regulating pancreatic beta cells excitability and insulin secretion. For example, transplantation of cells transfected with sodium or calcium channels can be utilized to increase depolarization of the beta cells or transplantation of cells transfected with calcium channels can be utilized to increase calcium influx thereby increasing beta cell sensitivity to depolarization. In addition these and other approaches can be utilized to increase and prolong the firing rate of such pancreatic cells.

Example 3

CNS

Epilepsy

Epilepsy is a chronic disorder usually associated with some alteration of consciousness and characterized by paroxysmal brain dysfunction due to excessive neuronal discharge.

Astroglial cells contribute to neuronal maintenance and function in the normal and diseased brain. Gap junctions, formed predominantly by connexin43 between astroglias, provide important pathways which coordinate astroglial responses (Reuss et al, 2000, Glia May; 30(3):231-41). Neuronal-glial interactions play an important role in information processing in the CNS. Previous studies have indicated that electro-tonic coupling between locus ceruleus (LC) neurons is involved in synchronizing the spontaneous activity. Moreover, Spontaneous oscillations in the membrane potential were observed in a subset of glial cells. These oscillations were synchronous with the firing of neurons, insensitive to transmitter receptor antagonists and disrupted by carbenoxolone, a gap junction blocker. Finally, immunoelectron microscopy studies established that connexins, the proteins that form gap junctions, were present on portions of the plasmalemma, bridging the cytoplasm of neurons and glia in LC (Alvarez et al, 2000, J Neurosci. June 1; 20(11):4091-8).

Treatment of epilepsy can be effected by the present invention by transplantation of astroglial cells, fibroblasts or other cells transfected ex-vivo with a restraining force channel coding sequence exemplified in Table 3 below.

TABLE 2

| Ion | Channel type | GenBank Accession numbers |
|---|---|---|
| Na | Sodium channel | AB027567 |
| Na | Voltage gated "SCN11A" | AF188679 |
| Na | hBNaC2"; product: "sodium channel 2 | U78181 AL035862 AA442069 AI017398 AI620655 AI762424 Z40887 AI700050 |
| Ca | T-type | AF134986 |
| Ca | 'VOLTAGE-DEPENDENT N-TYPE CALCIUM CHANNEL' | M94172 U76666 AA776162 T12610 |
| Ca | "L-type calcium channel (HFCC)"; Human' | M92269 AA927640 AA443875 AA173146 |
| Ca | "CACNG4"; product: "calcium channel' | AF142625 |
| Ca | 'VOLTAGE-DEPENDENT L-TYPE CALCIUM CHANNEL,' | AJ224874 AJ006216 |
| Ca | "voltage-dependent calcium channel' | M92301 W07059 T28094 |
| Ca | L-type | M76558 AF055575 H29339 R25307 T27949 AA885750 AW029633 AI955764 AW008794 AA978315 AI914244 AI951788 AW008769 H29256 AI963788 AI537488 AA468565 AA523647 AI361691 R46658 AW139850 AI017959 AA701888 AA703120 AA877582 |

TABLE 3

| Ion | Channel type | GenBank Accession numbers |
|---|---|---|
| K | Kv1.3 | H18261 |
| K | inward rectifier potassium channel TWIK-1 - human | S65566 |
| K | Delayed rectifier potassium channel - human | L28168 L33815 M26685 |
| K | Cardiac inward rectifier potassium channel - human | I38727 |
| K | VOLTAGE-GATED POTASSIUM CHANNEL PROTEIN KV1.4 | M55514 AI631014 AI701825 AI694934 AI793138 |
| K | 'voltage-gated potassium channel protein - human' | JC5275 |
| K | OKCNQ2"; potassium channel | AF033348 |
| K | 'inwardly rectifying potassium channel, hippocampal | I38521 |
| K | VOLTAGE-GATED POTASSIUM CHANNEL PROTEIN KQT-LIKE 3.KCNQ3. | AF033347 AF071491 AW205596 AW135705 AA019129 AA001392 H86059 H08544 R36327 T78692 AI125802 H08545 R49258 |

The transfected cells will be transplanted to the pathologic foci using standard neuro-surgical methods. Upon establishment of gap junction with the surrounding tissue, the cellular grafts form a single compartment which enables the repression of pathological tissue regions via controlled activation of the channels.

Example 4

Neuronal Networks

Neuronal cells were cultured on multi electrode arrays in efforts to determine electrophysiological function of these cultured cells under various conditions.

Culture Techniques

Cortical neurons were obtained from newborn rats within 24 hours from birth, following standard harvesting procedures (Culturing nerve cells, $2^{nd}$ edition, Gary Ranker and Kimberly Goslin, 1998). The cortex tissue was digested enzymatically and mechanically dissociated and the neurons were plated directly onto substrate-integrated multi-electrode array (MEA) dishes prepared as described below. The cultures were bathed in MEM which was supplemented with heat-inactivated horse serum (5%), Glutamine (0.5 mM), Glucose (20 mM), and Gentamycin (10 µg/ml), and maintained in a tissue culture incubator at 37° C., 5% $CO_2$ and 95% during the recording phases. Half of the medium was exchanged twice a week and the experiments were performed during the third week following plating, thus allowing complete maturation of the neurons (FIGS. 1a-b).

It is a well known fact that electrical activity in a cultured neuronal network is dependent upon synaptic transmission. As shown by various published studies, this electrical activity can be blocked by perfusion with the N-Methyl-D-aspartate (NMDA), receptor antagonist D-2-amino-5-phosphonovalerate (APV), and non-NMDA receptor antagonist 6-cyano-7-nitroquinoxaline-2,3-dion (CNQX).

To determine the sensitivity and accuracy of the multi electrode array and detecting system of the present invention, prior art electrical activity studies in cultured neuronal networks were repeated as part of the present study using intracellular recordings as well as MEA recordings.

Electrophysiological Methods

Arrays of 60 Ti/Au/TiN electrodes, 30 µm in diameter, spaced 200 µm from each other (MultiChannelSystems (MCS), Reutlingen, Germany) were utilized in the present study. The insulation layer (silicon nitride), was pretreated with poly-L-lysine forming a good surface for network development. A commercial 60-channel amplifier (B-MEA-1060, MCS, Reutlingen, Germany) with frequency limit range of 10-3000 Hz and a gain of ×1024 was utilized for signal amplification. The amplifier was connected to MCPPlus filter amplifiers (Alpha Omega, Nazareth, Israel) for further amplification (×10 to ×20). Stimulation through the MEA was performed using a dedicated 8-channel stimulus generator (MCS, Reutlingen, Germany).

In addition, the micro-incubation environment was arranged to support long-term recordings from MEA dishes. This was achieved by streaming a filtered, heated and humidified air/$CO_2$ (95/5%) gas mixture, and by electrically heating the MEA platform to 37° C. Data is digitized using two 5200a/526 A/D boards (Microstar Laboratories, WA, USA).

Experiments were first conducted in efforts to determine the functionality of the multi electrode array and the detecting system described above. The response of the cultured neuronal network to electrical stimuli is illustrated in FIGS. 1c-f.

Following electrical functionality determination, the neuronal network cultures were incubated with various electrical conduction blockers.

The addition of 5 µM bicuculin, 10 µM DNQX or 20 µM APV to the cultured neuronal network completely abolished spiking activity therein.

Epilepsy

Figure 2A:
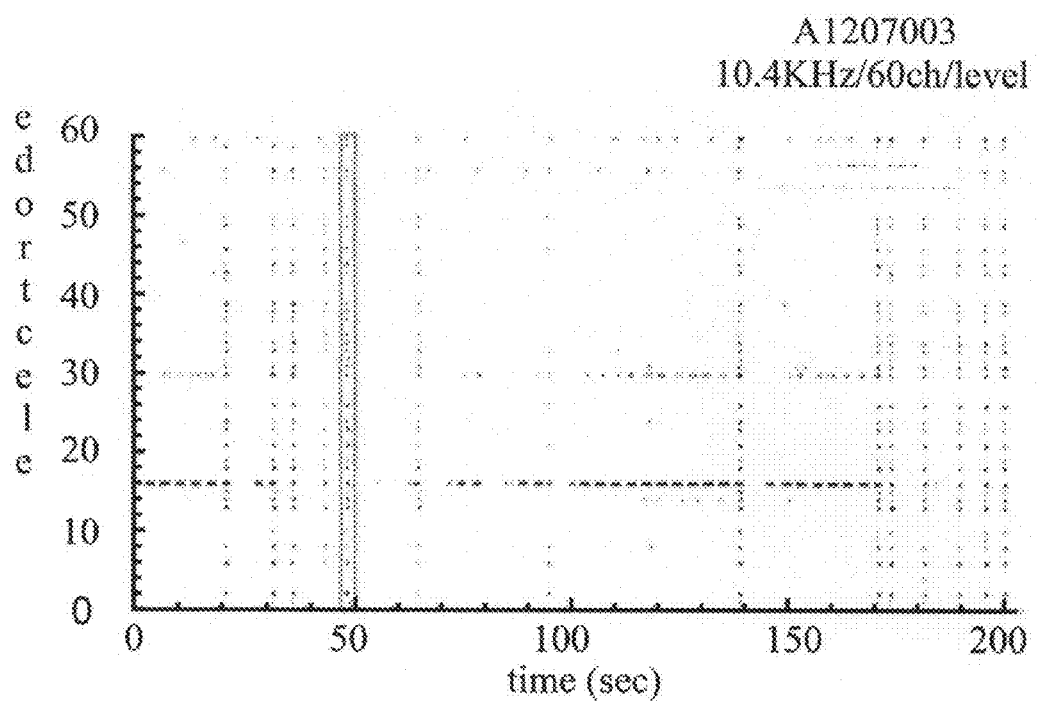
FIG. 2a illustrates epileptic activity recorded from MEA in a mature (3 weeks in vitro) cultured cortical network. The network is prepared and recorded from as explained in FIG. 1. The recorded spontaneously bursting synchronous activity throughout the network is a characteristic feature of epileptic-like activity in networks of neurons.
Figure 2B:
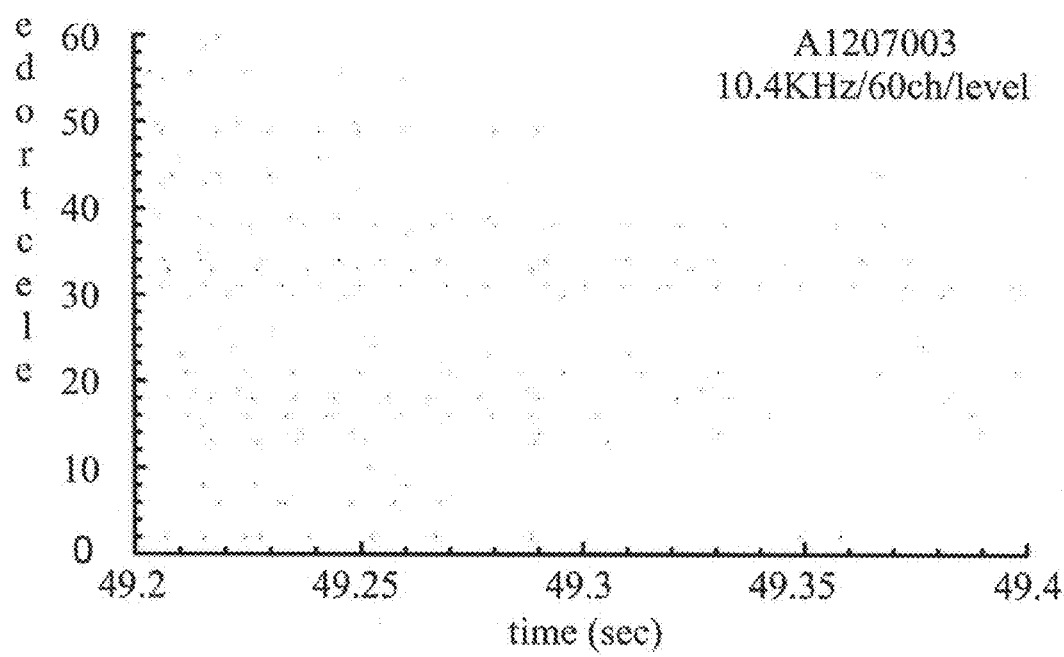
FIG. 2b illustrates an expanded time scale of the activity marked by the red box (left side) revealing a complex structure of a single burst.
Figure 3:
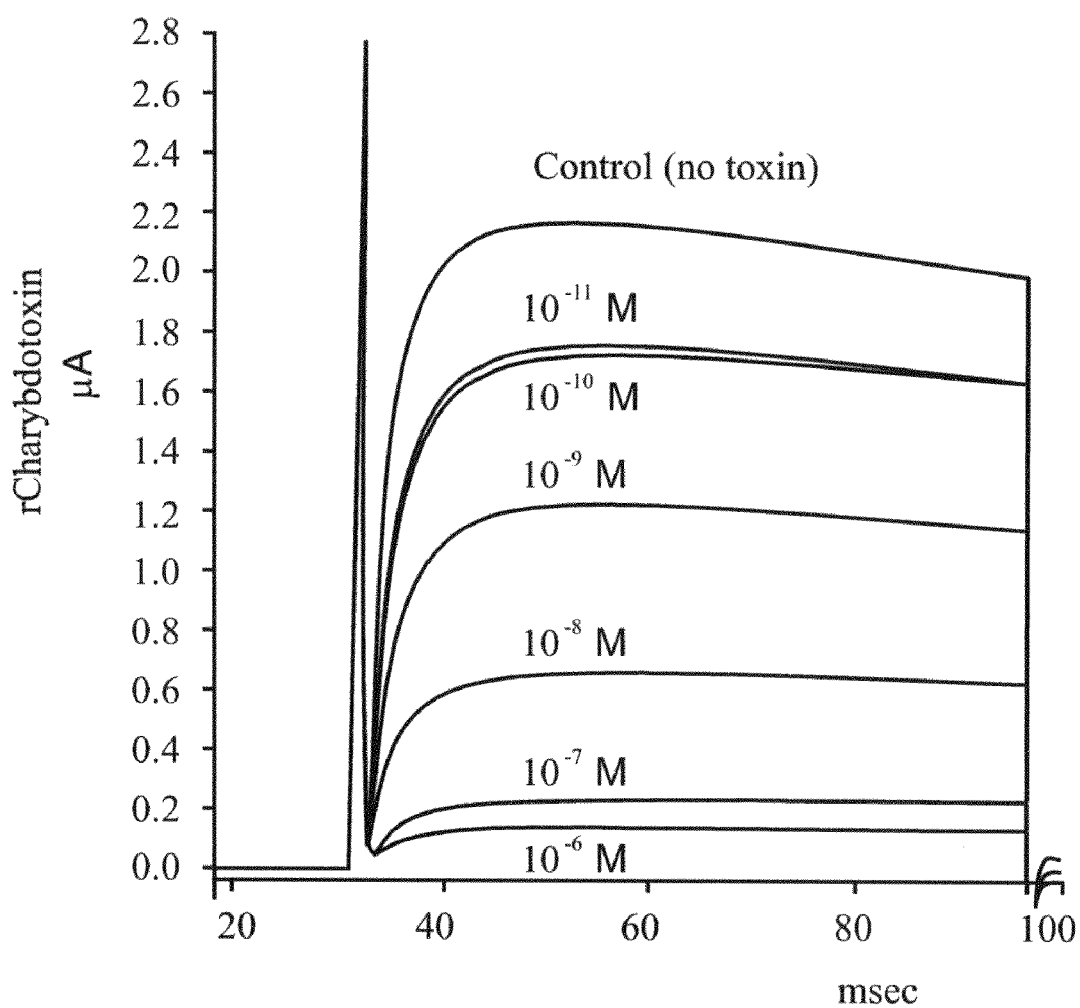
FIG. 3 illustrates the dose response to charybdotoxin of the Kv1.3 potassium channel.

Epileptic activity of the cultured neuronal network described above was measured from the MEA described above. FIGS. 2a-b illustrate epileptic activity recorded from MEA in a mature (3 weeks in vitro) cultured cortical network. This recorded spontaneously bursting synchronous activity throughout the network is a characteristic feature of epileptic-like activity in networks of neurons.

Example 5

Although electrical coupling between fibroblasts and myocytes has been previously reported by Rook et al. (1992), the experiments conducted as a part of that study were designed in efforts to elucidate the validity of modulating excitable tissue by cellular graft. Thus, Rook et al. did not describe nor did they suggest the use of cells transfected with ion channel coding sequences for the purpose of modifying the electrophysiological function of excitable tissues.

While reducing the present invention to practice, the present inventors utilized a cell culture model system which included fibroblasts which were transfected with ion channel coding sequences and co-cultured with cardiomyocytes. These co-cultures enabled to test the effects of the ion channel expressing fibroblast on the electrophysiological function of the myocardial cells and to test the effects of various molecules which regulate channel permeability.

Materials and Methods

Preparation of Cultured Cardiomyocytes

Monolayer cultures of neonatal rat ventricular cardiomyocytes (NRVM) were prepared as previously described (Rubin et al, 1995), with some modifications. The cultures were maintained in a humidified incubator under a controlled environment of 5% $CO_2$+95% air at 37° C.; fresh medium was replaced on alternating days.

Preparation of Fibroblast Cultures Transfected with Kv1.3

Fibroblasts from the NIH 3T3 cell line were transfected with an expression cassette which included a mutant voltage gated potassium channel (Kv1.3) coding sequence (GeneBank Accession number H18261) placed under the transcription control of a constitutive promoter using standard procedures. Fibroblast cultures not transfected with the channel coding sequence were produced from the NIH 3T3 cell-line.

Preparation of Co-Cultures

Once well synchronous spontaneous activity was established in the cardiomyocyte cultures, fibroblasts transfected with the Kv1.3 channel coding sequence or non-transfected fibroblasts were added to the cultures. Two different methods where used to seed the fibroblasts. In the first method, the fibroblast were suspended in trypsin for 5 minutes following which they were seeded in a diffuse pattern in the cardiomyocytic cultures (FIG. 4a). In the second method, the fibroblasts where pipetted up and down through a 5 ml pipette for 2 minutes and seeded in the cardiomyocytic cultures thus were forming clusters of fibroblasts (FIG. 4b).

Immunohistochemistry

The fibroblasts were labeled with Fast DiO [3,3'-dilinoleyloxacarbocyanine perchlorate (FAST DiO™ solid, Cat #-3898; Molecular Probes, USA) in order to track the fibroblasts in the co-cultures.

The Data Acquisition System and Electrical Activity Recording

Extracellular recordings from cultured cardiomyocytes were performed on a PC-based Microelectrode Data Acquisition System (Multi Channel Systems, Reutlingen, Germany), consisting of Multi-Electrode Array (MEA), pre- and filter-amplifiers, data acquisition board, and software. The MEA consists of a 50×50 mm glass substrate, in the center of which is an embedded 0.7×0.7 or 1.4×1.4 mm matrix of 60 Titanium-nitride, gold contacts 10 or 30 μm diameter electrodes insulated with silicone nitride, with inter-electrode distance of 100 or 200 μm (there are no electrodes in the corners of the matrix). Data were recorded at 10-25 KHz with 12-bit precision. During the recording sessions, the MEA (removed from the regular incubator) was constantly perfused with a gas mixture consisting of 5% $CO_2$+95% air. Temperature was kept at 37±0.10° C.

Construction of Activation Maps

Recorded data was filtered using cutoff frequency of 2 KHz (Fast et al, 1993). The filtered signal was then differentiated digitally to determine the Local Activation Time (LAT) at each electrode, corresponding to dF/dtmin (where F is the filtered signal) (Dolber and Spach, 1986). Color-coded activation maps were constructed by interpolating the LAT values for the sites between the electrodes, and by extrapolating the LAT values for the 4 corners of the MEA matrix. Activation maps were plotted by means of Matlab standard 2-d plotting function (pcolor) (Matlab 5.3 Mathworks Incorporated©). Conduction velocity was calculated by standard methods (Bayly et al, 1988).

Conduction Block

Conduction block quantification is central to evaluating conduction block development in the cell cultures, and to evaluating reversibility of the conduction block following CTX application. A conduction block was determined using the following algorithm:

the local activation time (LAT) of each electrode was compared to the LAT of the four nearest electrodes, where LATx is the local activation time at electrode x and LATy is the local activation time at one of the four nearest electrodes to electrode x. Thus, If LATx−LATy>0.25×[LATmax(last local activation time in the array)−LATmin(first local activation time in the array)], then the electrode was assigned a value of 1, else the electrode was assigned a value of 0. Each of the four electrodes was tested and if one or more satisfied this condition, then electrode x was set to a value−1, a sum of all the electrode values represented the block value.

Recording Protocol

Electrical activity of the cultures was recorded on day one immediately prior to seeding of the fibroblasts and then daily until the cultures died or no spontaneous activity was detected. During the daily measurements the cultures where subjected to increasing concentrations (0.1, 1, 10, 100 nM) of CTX.

Results

Spontaneous Activity

Measurement were performed during spontaneous activity from three groups of cardiomyocyte cultures: cultures without fibroblasts, cultures with NIH 3T3 fibroblasts (seeded diffusely) and cultures with transfected NIH 3T3 fibroblasts (expressing the mutant voltage gated potassium channel coding sequence).

The cultures where subjected to an increasing concentration of CTX from 0.1 to 100 nM. CTX caused a significant increase in the spontaneous activity rate in the co-cultures which included the transfected fibroblasts. The activity rate increased by 20 and 55% following administration of CTX concentrations of 10 and 100 nM respectively. In contrast, administration of CTX to cardiomyocyte cultures or to cardiomyocytes co-cultured with untransfected fibroblasts did not increase the activity rate at 10 nM and caused a modest increase of up to 15% at a 100 nM (FIG. 5).

There are three possible explanations for these results:

(i) Kv1.3 channel opening in transfected fibroblasts during action potential propagation causes hyperpolarization and therefore elongation of phase 4 at neighboring cardiomyocytes resulting in a slower activity rate; therefore, blocking of Kv1.3 channels with CTX reverses this effect. (ii) CTX treatment increases electrical activity in areas that are blocked due to the presence of fibroblasts.

(iii) CTX enables propagation through otherwise blocked conduction tracts thus enabling propagation of action potentials. Since the area of the electrode array is a 1×1 $mm^2$ and since the area of the plate in which the array is embedded is about 2 $cm^2$, most of the culture activity is not recorded because propagation of electrical signal from cells positioned outside the array may be blocked prior to entering the array. Application of CTX opens conduction blocks and thus enables activation of the myocytes at the electrode area.

The weak response observed in the control cultures treated with a high concentration of CTX is probably due to a minor blockage of potassium channels in the myocytes.

Synchronous Activity and Conduction Block

Figure 7A:
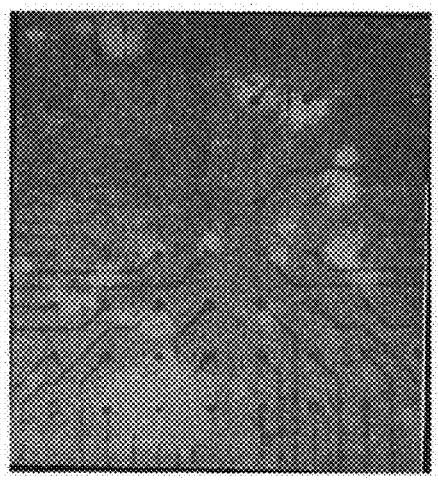
FIG. 7a is a fluorescent image of cardiomyocytes co-cultured with fibroblasts transfected with Kv1.3 channel coding sequences and labeled with Fast DiO on a MEA (cluster seeding pattern).
Figure 7B:
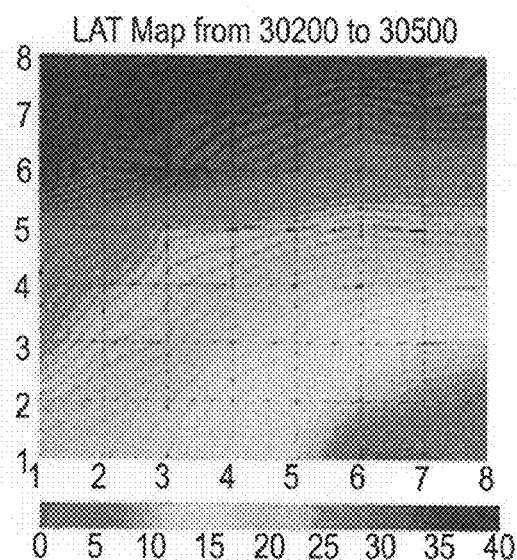
Figure 7C:
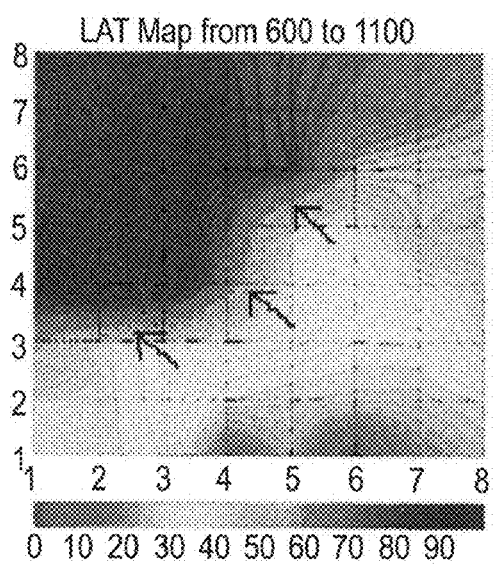
FIG. 7c is an activation map constructed five days following seeding of the fibroblasts described in FIG. 7a and prior to treatment with CTX illustrating the appearance of a conduction block.
Figure 7D:
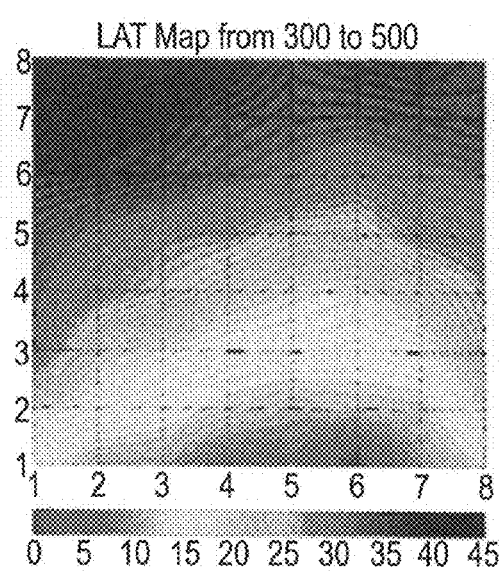
FIG. 7d is an activation map constructed five days following seeding of the fibroblasts described in FIG. 7a and following treatment with CTX 10 nM illustrating the reversal of the conduction block.
Figure 10:
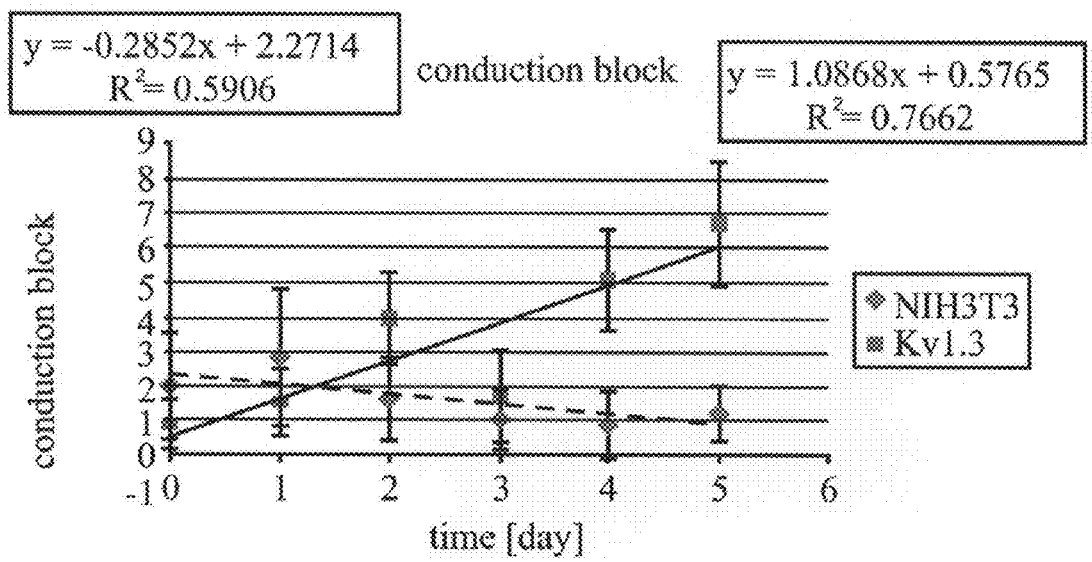
FIG. 10 illustrates the development of a conduction block in MEA seeded fibroblasts following measurement at day 0. A substantial increase in the conduction block factor was recorded from the culture including the fibroblast transfected with potassium channels (Kv1.3) (pink, n=5), while in the non-transfected fibroblast culture a decrease in the conduction block factor was recorded (blue, n=6).
Figure 11:
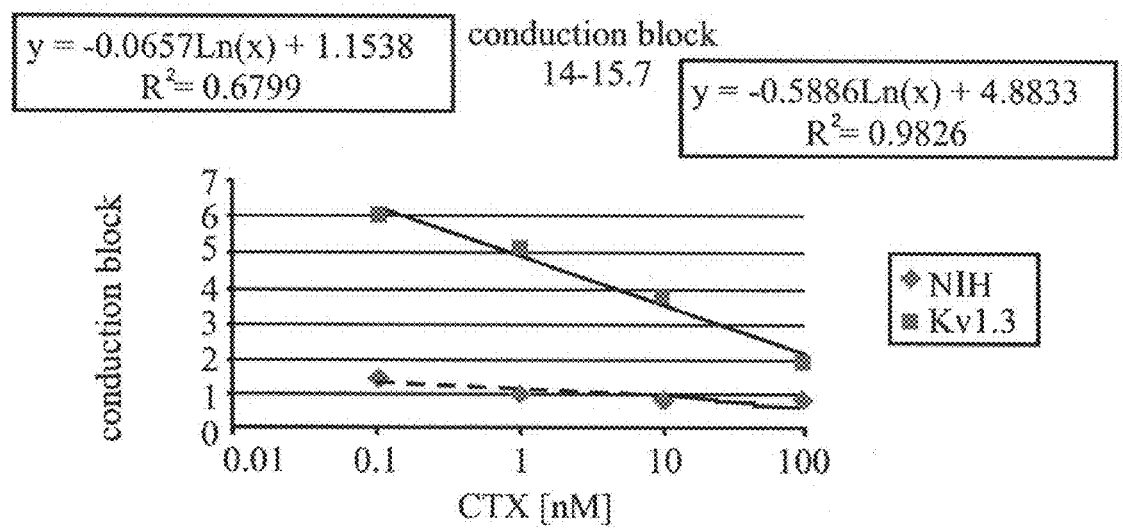
FIG. 11 illustrates the effects of Charybdotoxin (specific blocker of potassium channel Kv1.3) on conduction blocks. In co-cultures including fibroblasts transfected with Kv1.3, application of Charybdotoxin substantially decreased the conduction block factor (pink, n=10), while in co-cultures including non-transfected fibroblasts, a minimal response was recorded (blue, n=9).

The two control culture types (with or without untransfected fibroblasts) exhibited a well-coupled synchronous activity throughout the experiment. Four of the co-cultures with transfected fibroblasts demonstrated an uncoupling effect following the fibroblasts seeding due to a conduction block generated by the Kv1.3 channels formed in the fibroblasts. Uncoupling effect was reversed following treatment with CTX (FIGS. 6f-g). Almost all of the cultures which included transfected fibroblasts demonstrated conduction blocks which developed following fibroblasts seeding (FIG. 10). Such conduction blocks were reversed following treatment with CTX (FIG. 7d and FIG. 11).

Figure 8:
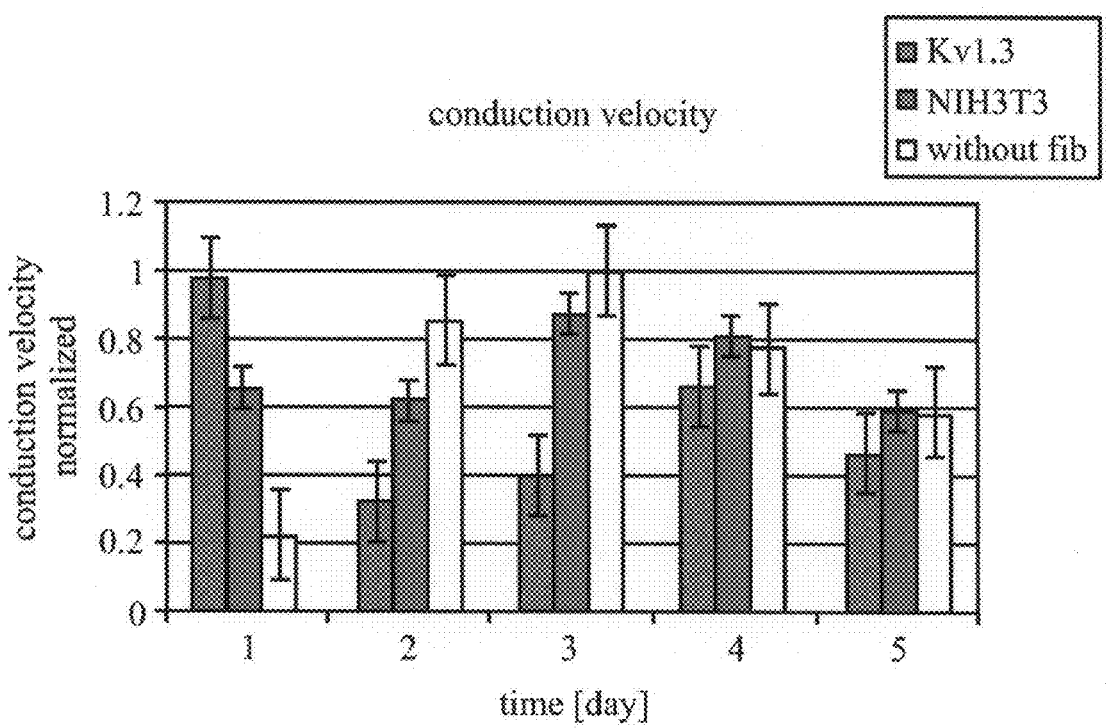
FIG. 8 illustrates the conduction velocity change throughout an experiment with seeded fibroblasts (in blue—myocytes with fibroblast transfected with Kv1.3, in brown—myocytes with fibroblast without Transfection (control 1), in yellow—myocytes without fibroblast (control 2)); fibroblasts where seeded following measurements at day 1; Kv1.3 c=4, NIH 3T3 c=3, without fib c=1 error bar—standard error.

Cultures including non-transfected fibroblasts did not demonstrate conduction blocks or reversibility of blocks following application of CTX (FIGS. 12a-d). An immediate decrease in conduction velocity following transfected fibroblast seeding was also observed. Such an effect was not observed in co-cultures that included non-transfected fibroblasts (FIG. 8).

Amplitude Change

Figure 9:
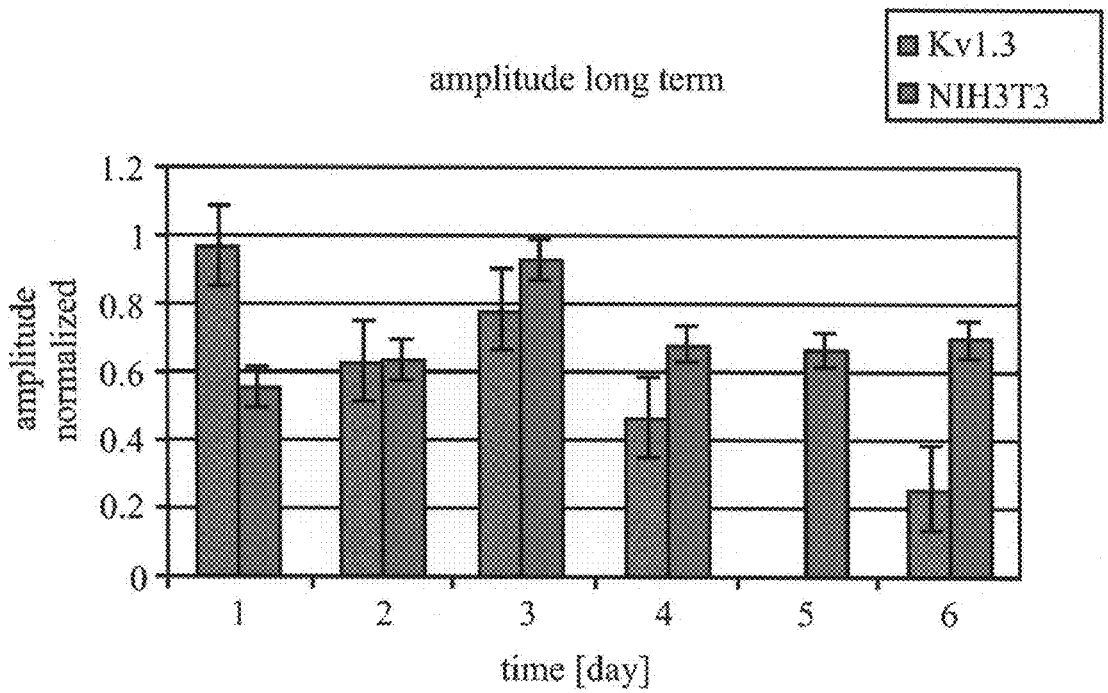
FIG. 9 illustrates the amplitude change throughout the experiment illustrated in FIG. 8; fibroblasts where seeded following measurements at day 1; Kv1.3 c=3, NIH 3T3 c=3 error bar—standard error.

In comparison to cultures seeded with non-transfected fibroblasts, the amplitude of the extracellular signals decreased significantly following seeding with transfected fibroblasts (FIG. 9). This result may indicate a general decrease in culture excitability, implicating a reduced mass of action potential generating cardiomyocytes or the presence of slow conduction.

Summary and Future Directions

The above described results demonstrate for the first time that transplantation of fibroblasts transfected with a Kv1.3 channel coding sequence into cardiomyocytic cultures causes a significant change in the electrophysiological function of this excitable tissue.

Specifically, reduced spontaneous rate of the co-culture's excitability, lower amplitude of extracellular potentials, reduced conduction velocity and generations of local conduction blocks, were generated. These changes where partially or fully reversed following administration of a specific Kv1.3 channel blocker, CTX. These results indicate the presence of tight structural and functional coupling between the fibroblasts and the myocytes, activation of the Kv1.3 channels and significant modulation of the electrical properties of the cultures.

Thus, the present invention provides a novel method which can be utilized to modulate the electrophysiological function of an excitable tissue region, which method can be utilized to treat various cardiac disorders.

The ability to modulate the electrophysiological properties of cardiac tissue may have significant clinical applications. Transplantation of cellular grafts having a predetermined electrical phenotype may be used, in the future, to alter the electrophysiological properties of cardiac tissue and together with pharmacological administration serve as a procedure for treating selected pathologies in the heart.

Furthermore, the method of the present invention is advantageous in that it effects a local tissue region rather then the heart as a whole, thus not affecting non-pathological tissue regions. This mode of treatment may be applied to treat a variety of cardiac arrhythmias.

For examples, transplantation of cellular grafts of the present invention to the AV node may be used for AV nodal modification, where the inherent properties of the cellular graft (the frequency response with or without specific pharmacology) can be used to modify the ventricular response during different atrial arrhythmias thus replacing the need for pharmacological treatment.

Local transplantation of the cellular grafts of the present invention may also be used to repress arrhythmogenic foci arising due to abnormal automaticity or to repress triggered activity by modulating the action potential in selected tissue regions.

In addition, reentrant arrhythmia may also benefit from the teachings of the present invention. Cellular grafts may be used to create a local conduction block in a critical area of the circuit thus treating the arrhythmia. Alternatively, predetermined seeding patterns may be used to create barriers or lines of conduction blocks for the treatment of more complex reentrant arrhythmias such as atrial fibrillation or flutter. In the later two cases, specific cell types can be used to allow normal conduction during slow (normal) rhythms, while creating local conduction blocks during fast (pathological) rhythms.

Example 6

The teachings of the present invention may also be applied to modify the electrophysiologoical functionality of excitable tissues such as, for example, nervous tissue and glandular tissue. For examples, cells transfected with selected ion channel proteins may be used to modulate focal pathological areas in the CNS, thus enabling treatment of disorders such as Parkinson's disease.

Parkinson's disease is a neurological disorder which typically results from deficiency of the neurotransmitter dopamine as the consequence of degenerative, vascular, or inflammatory changes in the basal ganglia. Parkinson's disease is characterized by rhythmical muscular tremors, rigidity of movement, festination, droopy posture, and masklike facies.

Astroglial cells contribute to neuronal maintenance and function in the normal and diseased brain. Gap junctions formed between astroglial cells, predominantly by connexin43, provide the pathways which coordinate astroglial responses (Reuss et al, 2000, Glia May; 30(3):231-41). Neuronal-glial interactions play an important role in information processing in the CNS. Previous studies have indicated that electrotonic coupling between locus ceruleus (LC) neurons lays a role in synchronizing the spontaneous activity. Moreover, spontaneous oscillations in the membrane potential were observed in a subset of glia. These oscillations were synchronous with the firing of neurons, insensitive to transmitter receptor antagonists and disrupted by carbenoxolone, a gap junction blocker. Finally, immunoelectron microscopy studies established that connexins, the proteins that form gap junctions, were present within the plasmalemma, bridging the cytoplasm of neurons and glia in LC (Alvarez et al, 2000, J Neurosci. June 1; 20(11):4091-8).

Methodology

Astroglial cells transfected to express selected ion channel and optionally gap junction proteins will be transplanted within the pathologic foci (e.g., Substantia nigra) using standard neuro-surgical methods.

Gap junction formation between the cellular graft and cells of the pathological region and activation of expressed ion channels (e.g., sodium channels) will substantially increase the excitability of the diseased tissue. In the case of compromised number of dopaminergic cells, the transplanted cells may increase synchronicity, thus effectively increasing timed release of dopamine or any other relevant neuromodulator.

Example 7

Enhancement of Insulin Secretion from β-Cells

Background

Diabetes mellitus is a metabolic disease in which carbohydrate utilization is reduced and that of lipid and protein enhanced; it is caused by an absolute or relative deficiency of insulin. Abnormalities in insulin secretion precede the onset of type-2 diabetes and may be present even when subjects show normal glucose tolerance (UK Prospective Diabetes). By the time of diagnosis, insulin secretion is significantly reduced and it continues to diminish inexorably throughout the course of the disease (UK Prospective Diabetes). The disease is characterized, in more severe cases, by chronic hyperglycemia, glycosuria, water and electrolyte loss, ketoacidosis, and coma; long-term complications include development of neuropathy, retinopathy, nephropathy, generalized degenerative changes in large and small blood vessels, and increased susceptibility to infection [see also Example 2, above; Kahn S E. The relative contributions of insulin resistance and beta-cell dysfunction to the pathophysiology of Type 2 diabetes. Diabetologia. 2003; 46(1):3-19.].

β-Cells within the pancreatic islets are responsible for insulin secretion. Insulin secretion is the product of a chain reaction response to low glucose level. This chain reaction begins with the closure of ATP-dependent potassium channels which leads to depolarization in β Cell's membrane potential, opening of Calcium channel (voltage dependent) and calcium entrance to the cell's cytoplasm. Calcium in the cytoplasm causes fusion of vesicles (containing insulin) with the β Cell membrane and secretion of insulin to the blood stream.

Electrical activity plays a critical role in the regulation of insulin secretion [Ashcroft, F. M. and Rorsman, P. (1989) Electrophysiology of the pancreatic β-cell. Prog. Biophys. Mol. Biol., 54, 87-143]. No insulin is secreted in the absence of β-cell electrical activity, and there is a direct correlation between the extent of β-cell electrical activity, once initiated, and the amount of insulin secretion [Henquin, J. C. and Meissner, H. P. (1984) Significance of ionic fluxes and changes in membrane potential for stimulus-secretion coupling in pancreatic β-cells. Experientia, 40, 1043-1052]. Thus changes in electrical activity are immediately mirrored by changes in insulin secretion.

The stimulatory actions of almost all insulin secretagogues, including glucose, neurotransmitters and hormones, converge at the level of electrical activity, which serves to integrate the effects of all these agents. Although most secretagogues have additional downstream effects on insulin secretion [Henquin, J. C. (2000) Triggering and amplifying pathways of regulation of insulin secretion by glucose. Diabetes, 49, 1751-1760., Rorsman, P. and Renstrom, E. (2003) Insulin granule dynamics in pancreatic p cells. Diabetologia, 46, 1029-1045], none are effective in the absence of electrical activity. Thus, β-cell electrical activity is an essential step in insulin release [Ashcroft, F. M. and Rorsman, P. (2004) Human Molecular Genetics, 1 R21-R31].

The β-cells are electrically coupled to one another, such that the islet functions as an electrical syncytium [Meissner, H. P. (1976) Electrophysiological evidence for coupling between b cells of pancreatic islets. Nature, 262, 502-504., Eddlestone, G. T., Goncalves, A., Bangham, J. A. and Rojas, E. (1984) Electrical coupling between cells in islets of Langerhans from mouse. J. Membr. Biol., 77, 1-14., Santos, R. M., Rosario, L. M., Nadal, A., Garcia-Sancho, J., Soria, B. and Valdeolmillos, M. (1991) Widespread synchronous [Ca2P]i oscillations due to bursting electrical activity in single pancreatic islets. Pflugers Arch., 418, 417-422]. This serves to coordinate electrical activity and insulin secretion across the islet and accounts for the fact that glucose-stimulated insulin secretion from a single islet is pulsatile and mirrors the slow waves of electrical activity [Bergsten, P. (1995) Slow and fast oscillations of cytoplasmic Ca2P in pancreatic islets correspond to pulsatile insulin release. Am. J. Physiol., 268, E282-E287]. β Cells connect through connexin36 (Diabetes 49:727-734, 2000) which does not connect with other connexin type proteins (Nat Rev Neurosci. 2001 June; 2(6):425-33).

Enhancements of insulin secretion—Insulin secretion may be enhanced by two basic mechanisms: first, increasing coupling between p Cells; and second, increasing β Cell excitability (e.g., increasing bursting rate, increasing bursting duration, reducing silent duration, increasing bursting amplitude). Increased coupling may be achieved by transplanting cell (autologous, allogenic or xenogeneic) capable of electrical coupling with pancreatic β cells. Examples of cells capable of forming electrical coupling with foreign tissue are Mesenchymal stem cells [Valiunas V. et al. J Physiol. (2004) 555(Pt 3):617-26], pancreatic cells, embryonic stem cells or fibroblasts [Gaudesius G. et al. Circ Res. $(2003)_{93}(5)$:421-8. Epub 2003 Jul. 31].

Increased coupling may also be achieved by transplantation of cell grafts overexpressing connexin channels (e.g. connexin36, connexin40, connexin43, connexin45), depolarizing ion channels (e.g. sodium channels, calcium channels) and/or non-selective ion channels. Examples for sodium channels: (a) SCN5A, (b) Mutant SCN5A (ΔKPQ, N1325S, R1644H, E1295K, D1790G, ins1795) (these mutations cause LQTS and/or Brugada syndrome, and are characterized by long activation, and/or persistent current), (c) SCN1A, (d) SCN2A, (e) SCN3A, (f) SCN4A, (g) SCN8A, (h) SCN9A, (i) SCN10A, (j) SCN11A, (k) HCN channel family (e.g. hHCN2, hHCN4, mHCN1, mHCN2).

Examples of calcium channels include: (a) L-type, and (b) T-type calcium channels. Other examples of calcium channels are described in Example 2, above Examples of non-selective ion channels include channels of the HCN family.

In vivo gene transfer into pancreatic β-cells can be effected by injection of naked DNA of viral DNA vector including the polynucleotides of interest (i.e., ion channel encoding polynucleotide and/or gap junction encoding polynucleotide) to an artery feeding the pancreas. Injection may be localized such as by CT guided injection, ERCP, laparoscopy or laparotomy. Alternatively, when a β-cell specific promoter is used injection may be systemic such as intravenous injection.

Cells for ex vivo gene transfer are selected capable of forming electrical coupling with cells. To improve efficacy, cells preferably over express either of the above-described polynucleotides. Cell delivery into the pancreas can be effected by direct CT guided injection, injection through ERCP, laparoscopy, or laparotomy, or injection of cells to an artery feeding the pancreas.

The following describes treatment of type 2 Diabetes mellitus by modifying the electrical activity of β-cells using cellular grafts. To this end genetically modified fibroblasts overexpressing a specific ion channel were used and transplanted into rat's pancreas.

Materials and Experimental Procedures

DNA constructs—Two different constructs were used including pcDNA3/Nav 1.5 [hH1A, GenBank Accession No. XM_427864, Zhang Y, Hartmann H A, Satin J. J Membr Biol. October 1; 171(3):195-207] and pRC/CMV/KV1.3 [GenBank Accession No. H18261, Feld et al. Circulation. 2002; 105:522-529.

Generation of Cell Grafts

Transfections—NIH/3T3 fibroblasts (ATCC: CRL 1658) were transfected using Lipofectin Reagent (Invitrogen) according to manufacturer instructions. 72 hours following transfection 500 □g/ml of G-418 (GIBCO, LANGLEY, OK, USA) was added to the growth medium (DMEM—GIBCO, LANGLEY, OK, USA) supplemented with 10% FCS (Biological industries, Beit Haemek, Israel), gentamycin sulphate 50 μg/ml (Biological industries, Beit Haemek, Israel), penicillin 100 U/ml (Biological industries, Beit Haemek, Israel), and streptomycin 100 □g/ml (Biological industries, Beit Haemek, Israel) for selection of cells expressing the neomycin resistance gene. Clones were isolated using cloning rings.

Molecular and electrophysiological screening—PCR analysis was effected to all NAV1.5 clones in order to confirm presence of the desirable gene. PCR was done using a PCR ReddyMix™ (ABgene). Reaction mixture included Thermoprime Plus DNA Polymerase, Tris-HCL (pH=8.8 at 25° C., $(NH_4)_2SO_4$, $MgCl_2$, Tween™20 and dNTPs. Genomic DNA for PCR screening was generated by High pure PCR template preparation kit (Roche Diagnostic). Two pairs of primers were used to detect the Nav1.5 gene: Primers for C terminus of the genes (amplifying 547 bp)-hH1A-ATG sense: atggcaaacttcctattacct (SEQ ID NO: 1); hH1A-547 anti sense: ggcagaagcctcgagccagaat (SEQ ID NO: 2). Primers for N terminus of the genes (amplifying 659 bp)-hH1A-5369 sense: tcgatatgttctatgagatctg (SEQ ID NO: 3); hH1A-6052 anti sense: ctcacacgatggactcacg (SEQ ID NO: 4).

Whole-cell recordings were conducted on a KV1.3 clone. The recordings were conducted at room temperature using Axopatch 200 (Axon Instruments). Data was collected using a Quadra 800 (Apple computers) with PULSE software (HEKA Electronic), low-pass filtered at 5 to 10 kHz and sampled at 20 kHz. Electrodes for voltage-clamp experiments were made from borosilicate glass, with a resistance of 2 to 4 MΩ. The pipette solution contained KCl 140 [mmol/L], $Na_2ATP$ 10 [mmol/L], EGTA 10 [mmol/L], HEPES 5 [mmol/L], $CaCl_2$ 1 [mmol/L], and $MgCl_2$ 1 [mmol/L] (pH 7.3). The bath solution contained NaCl 140 [mmol/L], KCl 3 [mmol/L], HEPES 10 [mmol/L], glucose 10 [mmol/L], $MgCl_2$ 2 [mmol/L], and $CaCl_2$ 2 [mmol/L].

One week prior to transplantation the selected clone was expanded in order to obtain suitable amount of cells for transplantation ($4 \times 10^6$ cells for each animal). On the day of transplantation, cells were trypsinated for 5 minutes, counted, centrifuged and re-suspended in 200 μl serum-free DMEM (GIBCO, Langley, Okla., USA). The cells were loaded into a syringe, and transported to the transplantation theater on ice.

Cell transplantation—Seven Sprague-Dawely rats were divided randomly to three different experimental conditions as detailed in Table 4, below.

TABLE 4

| Number of animals | Experimental condition |
|---|---|
| 3 | Control: Pancreas was injected with 200 μl of saline. |
| 3 | Nav1.5: Pancreas was injected with $4 \times 10^6$ fibroblasts over expressing the $Na^+$ ion channel Nav1.5. |
| 1 | Kv1.3: Pancreas was injected $4 \times 10^6$ fibroblasts over expressing the $K^+$ ion channel Kv1.3. |

Rats were anaesthetized with an intraperitoneal injection of Xylasine (0.5 mg/kg) and Ketamine (0.5 mg/kg). Animals were kept warm on a heat mat heated to 38° C. throughout the anesthesia to prevent hypothermia. The rats were operated ventrally by a median cut (4 cm long) exposing the pancreas. Genetically modified fibroblasts were injected to the head of the pancreas on 10 different sites. The animals were sutured, and got single dose of antibiotics. Animals were treated with CyclosporinA (CsA) 5 mg/Kg/Day in order to prevent graft rejection. Antibiotic treatment was initiated one day prior to the first surgical procedure, and continued during the whole experiment.

Intravenous glucose tolerance test—One week following graft transplantation, an Intravenous Glucose Tolerance Test (IVGTT) was conducted. Rats were anaesthetized as previously described. Rats were shaved at the front nape of the neck. The trachea was isolated and a plastic tube was inserted to assist with breathing during the experiment. The right jugular vein was isolated and tied off in its upper part. Then an incision was made in order to insert the cannula. The cannula was washed with heparinized saline (35 U/ml) to maintain patency. 30 minutes following the induction of anaesthesia, two sequential fasting blood samples were retrieved. The IVGTT was commenced with a glucose load of 0.7 g/kg 50% glucose (w/v) as a single pulse over 30 seconds. Blood samples (200 μL) for glucose and insulin analyses were collected to eppendorf tubes (without any heparine/EDTA) at 0, 2, 4, 6, 10, 20, 30, and 45 minutes following the glucose load. Plasma glucose levels were analyzed using Glucometer (Glucometer EliteXL, Bayer Ltd). Plasma insulin concentration was analyzed using radioimmunoassay kit (Linco, St Louis, Mo., USA).

Fibroblast labeling—In order to track the transplanted cells, fibroblasts were labeled with fluorescent cell tracker CM-Dil (molecular probes).

Results

Figure 13:
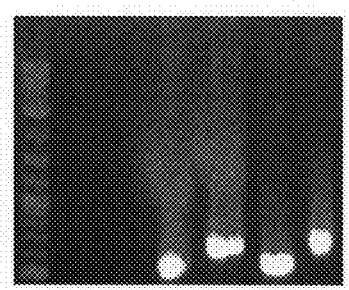
FIG. 13 is a photomicrograph depicting PCR screening of Nav1.5-expressing fibroblasts. Lane 1: DNA ladder. Lane 2: Negative control wherein the PCR reaction mixture includes N-terminus primer with no DNA template. Lane 3: Negative control the PCR reaction mixture includes only C-terminus primers with no DNA template. Lane 4: positive control N-terminus primers with pcDNA3/Nav1.5 plasmid. Lane 5: positive control C-terminus primers with pcDNA3/Nav1.5 plasmid. Lane 6:NIH/3T3 fibroblasts transfected with pcDNA3/Nav1.5 with N-terminus Nav1.5. Lane 7: NIH/3T3 fibroblasts transfected with pcDNA3/Nav1.5 with C-terminus Nav1.5.

PCR analysis of the clones—PCR analysis was effected to select the best expressing clone for cell transplantation. FIG. 13 shows PCR screening of the transplanted Nav1.5 clone.

Figure 14A:
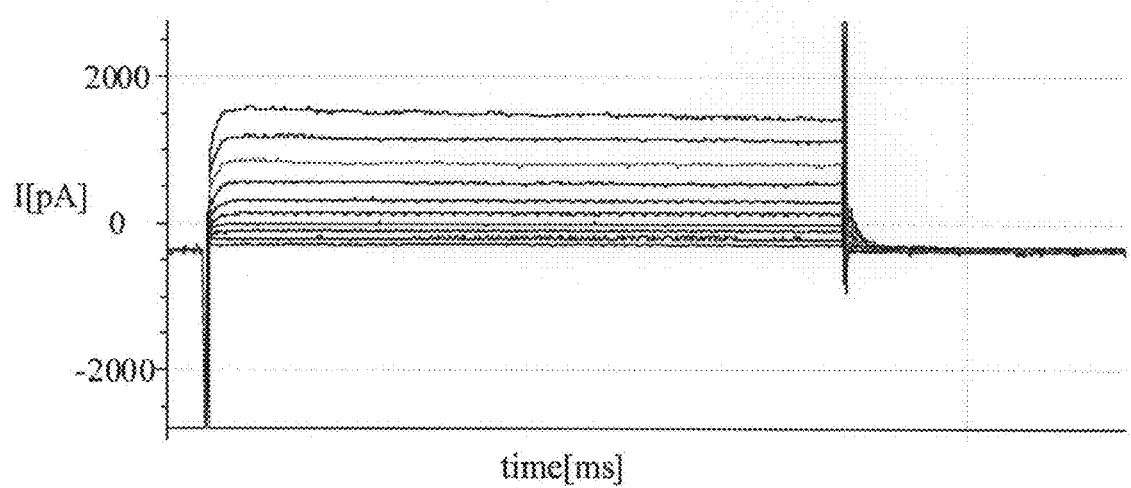
FIGS. 14a-b are graphs depicting voltage clamp recordings from transfected fibroblasts preformed in holding potential of −100 mV (FIG. 14a) and a corresponding I-V curve (FIG. 14b).
Figure 14B:
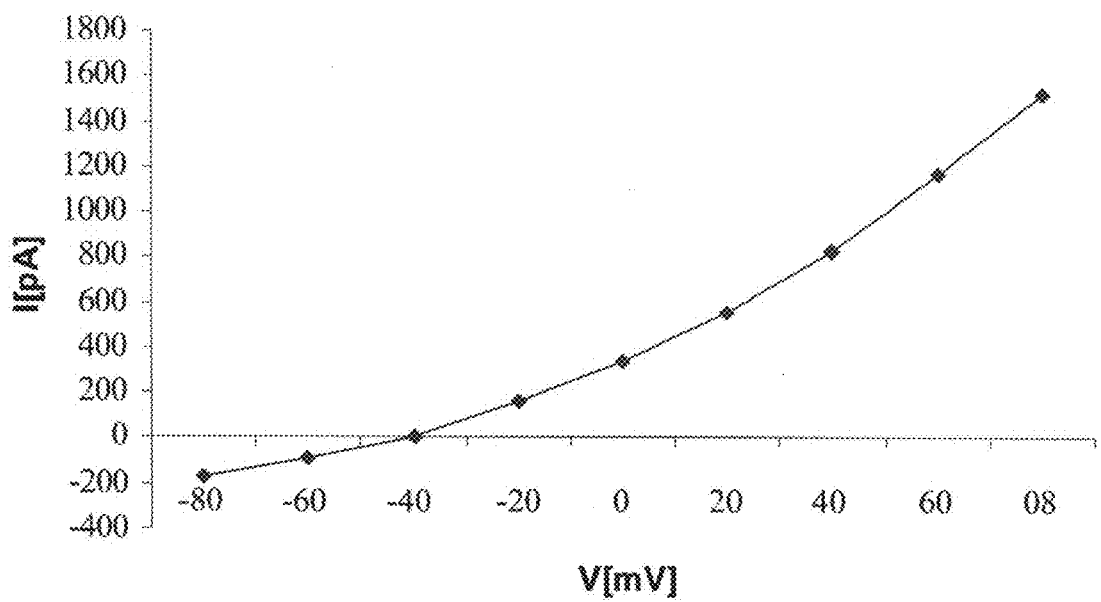

Voltage clamp analysis of transfected fibroblasts—Voltage clamp analysis (FIG. 14a) and the corresponding current-voltage (I-V) curve (FIG. 14b) demonstrated the presence of high magnitude outward potassium current with rapid activation kinetics in the transfected fibroblasts. Previous studies have already demonstrated that no significant transmembrane currents are present in naive NIH/3T3 (Feld et al. 2002). A similar voltage clamp study is presently conducted on fibroblasts expressing the ion channel Nav1.5.

Figure 15:
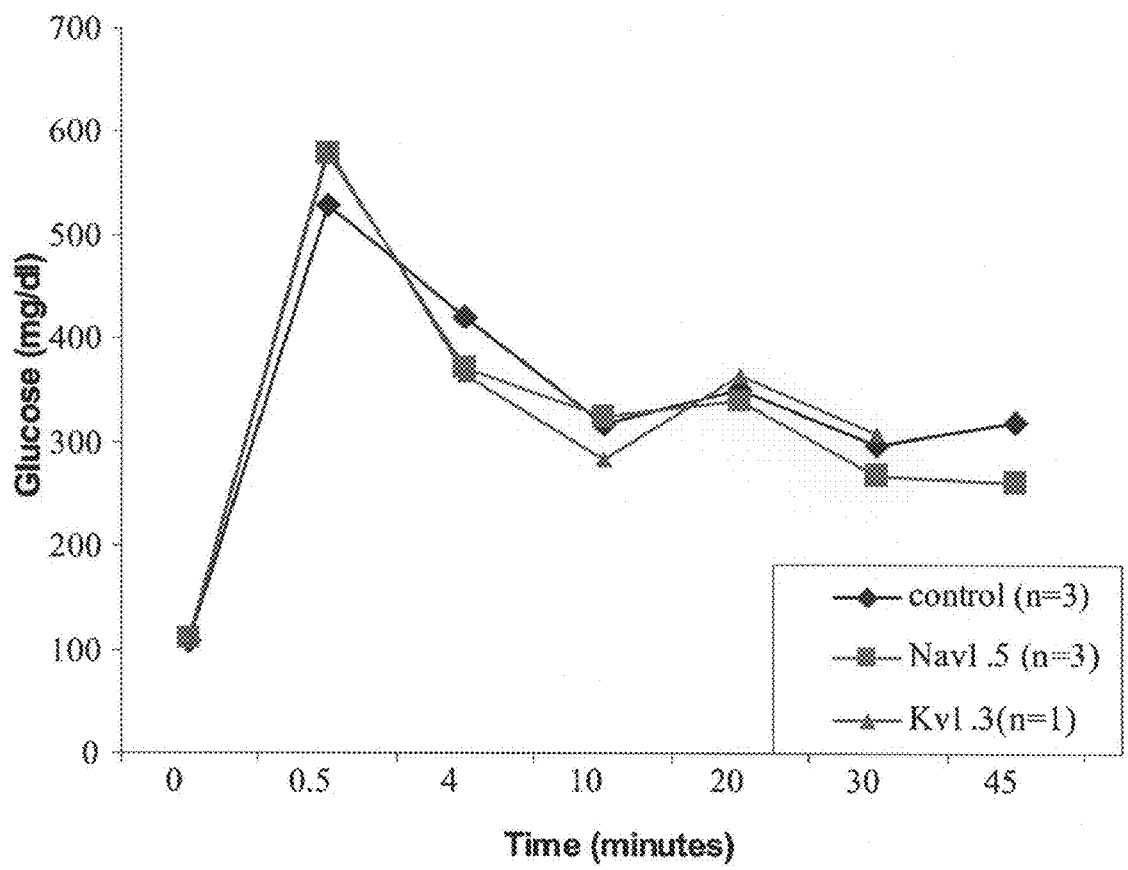
FIG. 15 is a graph depicting plasma glucose concentration during IVGTT in genetically manipulated rats (squares and triangles) and in control treated rats (circles).
Figure 16:
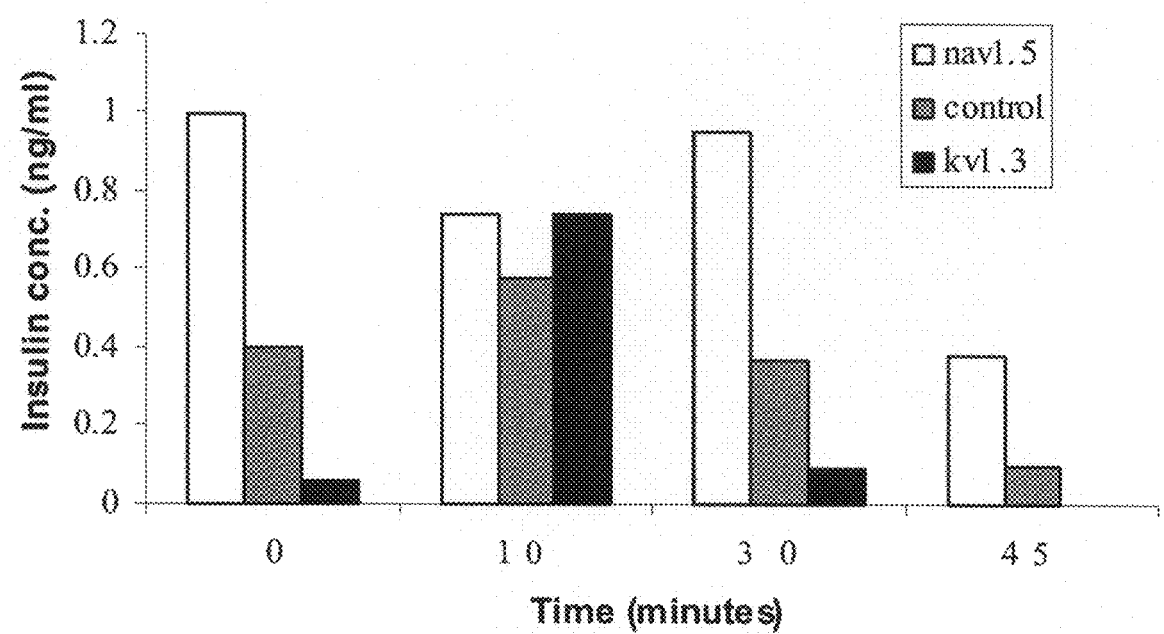
FIG. 16 is a bar graph depicting plasma insulin levels in 3 different time points during the IVGTT in genetically manipulated rats (gray) and in control treated rats (black).

Intravenous glucose tolerance test—Changes over time in plasma glucose concentrations after intravenous glucose load are shown in FIG. 15. Changes over time in plasma insulin concentrations after intravenous glucose load are shown in FIG. 16. Unexpectedly in the Nav1.5 group, insulin levels were reduced after the glucose load. The control group presents more typical response to IVGTT with maximum plasma insulin level concentrations reaching 10 minutes following the glucose load.

Figure 17:
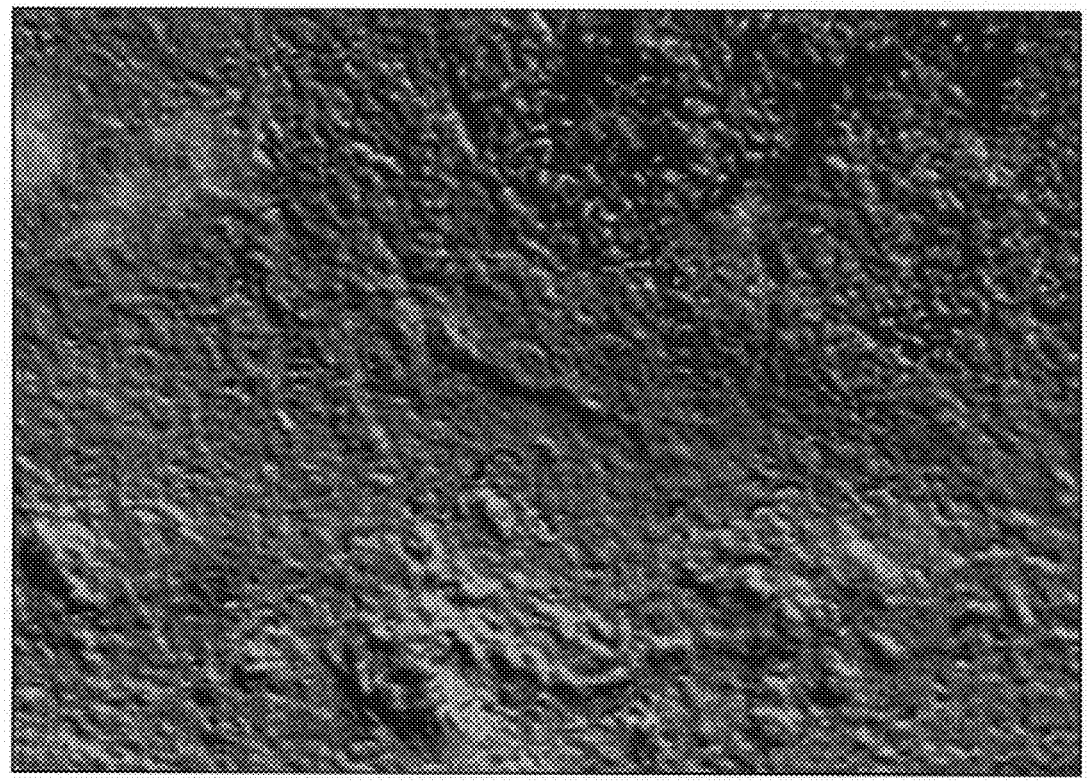
FIG. 17 is a photomicrograph depicting genetically manipulated fibroblasts (red) in pancreatic tissue slice as detected by histological analysis.

At the end of the experiment the animals were sacrificed and the pancreas of one rat was extracted for histological studying. FIG. 17 demonstrates fibroblasts labeled with CM-Dil in the pancreas at the end of the experiment.

Thus, the present study demonstrates the ability to inject genetically modified cells to rat pancreas to thereby change the plasma insulin and glucose levels in diabetic rats. Specifically, all the animals survived the operation and were vital during whole experimental period. The implanted cells survived at the rat pancreas for a week as was demonstrated by immunohistochimestry. The Nav1.5 expressing animals exhibited lower glucose levels 45 minutes following glucose load, as comparde to control animals. The basal insulin levels were the highest for the Nav1.5 animals and the lowest for the Kv1.3 animal (not shown). The overall insulin secretion over time was higher for the Nav1.5 animals in comparison to control animals.

Example 8

Biological Pacemakers and Prolonging the Refractory Period of the Cardiac Tissue Biological pacemakers can be produced by increasing excitability at a specific location or diffusely in a large area. Increasing excitability can be achieved by the following:

Transplantation of cell grafts (autologous, allogenic or xenogenic) capable of forming electrical coupling with host tissue. Examples are Mesenchymal stem cells [Valiunas V. et al. J Physiol. (2004) 555(Pt 3):617-26] or fibroblasts [Gaudesius G. et al. Circ Res. (2003) 93(5):421-8. Epub 2003 Jul. 31] or myoblasts or embryonic or embryonic derived stem cells (e.g., cardiomyocytrs, myocytes, fibroblasts, Mesenchymal cells, etc.). The cells are ex vivo genetically modified to over-express sodium channels: for example (a) SCN5A, (b) Mutant SCN5A (□KPQ, N1325S, R1644H, E1295K, D1790G, ins1795) (these mutations cause LQTS and/or Brugada syndrome, and are characterized by long activation, and/or persistent current), (c) SCN1A, (d) SCN2A, (e) SCN3A, (f) SCN4A, (g) SCN8A, (h) SCN9A, (i) SCN10A, (j) SCN11A and/or calcium channels, Examples for calcium channels are: (a) L-type, and (b) T-type, and (c) N-type calcium channels, and/or non selective HCN channel family (e.g. hHCN2, hHCN4, mHCN1, mHCN2), and/or leak ion channel (e.g. KCN-K family channel [Goldstein S. et al. Nature review neuroscience (2001): 2, (3) 175-184].

This method can be further enhanced by transplantation of cells overexpressing also connexin channel (e.g. connexin40, connexin43, connexin45). An alternative approach can be the introduction of these sodium or calcium or non-selective or leak channels directly (without a cell as a vehicle as naked DNA sequence or with viral vectors). The cells/DNA sequence can be transplanted in the atrial tissue at a predetermine pattern or diffusely (e.g. through coronary artery or surgery), the cells/DNA sequence can be transplanted to the area and/or surroundings of the AV node (e.g. by catheterization through coronary arteries (AV nodal artery), or surgery, or directly by endocardial injection catheter) or to specific area in the cardiac ventricles (e.g. by catheterization through coronary arteries, or surgery, or directly by endocardial injection catheter). These approaches can be used for the treatment of bradycardias from all causes (e.g. AV block, sick sinus syndrome), this approach can also be utilized for the treatment of atrial fibrillation combined with AV nodal ablation (ablate and pace procedure).

Prolongation of cardiac tissue refractory period can be achieved by the following procedures: Transplantation of cell grafts (autologous, allogenic or xenogenic) capable of forming electrical coupling with host tissue. Examples are Mesenchymal stem cells [Valiunas V. et al. J Physiol. (2004) 555(Pt 3):617-26] or fibroblasts [Gaudesius G. et al. Circ Res. (2003) 93(5):421-8], embryonic stem cells or derivatives thereof or myoblasts. The cells serve as a current sink, and therefore increase the amount of ionic current that is needed for generation of an action potential. This method can be further enhanced by transplantation of cells overexpressing connexin channel (e.g. connexin40, connexin43, connexin45) and/or overexpressing sodium channels [e.g. Mutant SCN5A (□KPQ or N1325S or R1644H or E1295K or D1790G or ins1795, these mutations cause LQTS and/or Brugada syndrome, and are characterized by long activation, and/or persistent current] and/or overexpressing potassium channels [e.g. voltage gated potassium channel (e.g. Kv1.1, Kv1.2, Kv1.3, mutant Kv1.3H401W)], Kir family: (e.g. Kir2.1) and/or overexpressing chloride channels (e.g. CIC family)). An alternative approach can be the introduction of these ion channels directly (without a cell as a vehicle as naked DNA sequence or with viral vectors). The cells/DNA sequence can be transplanted in the atrial tissue at a predetermine pattern or diffusely (e.g. through coronary artery or surgery), the cells/DNA sequence can be transplanted to the area and/or surroundings of the AV node (e.g. by catheterization through coronary arteries (AV nodal artery), or surgery, or directly by endocardial injection catheter) or to specific area in the cardiac ventricles (e.g. by catheterization through coronary arteries, or surgery, or directly by endocardial injection catheter). These approaches can be used for the treatment of atrial fibrillation, atrial flutter, atrial tachycardia, and ventricular tachycardia.

Materials and Experimental Procedures

Expression system and electrophysiological recordings—NIH 3T3 fibroblast cells (ATCC: CRL 1658) were stably transfected to express the voltage gated potassium channel Kv1.3 as previously described [Feld Y. et al. Circulation. (2002); 105:522-529]. Briefly, stable transfection of pRC/CMV/Kv1.3 in fibroblasts was achieved using electroporation with a single pulse of 200 V, 960 μF followed by antibiotic selection of NeoR clones with 400 μg/mL of G-418 (GIBCO, Langley, Okla., USA). Colonies were picked and tested for channel expression using whole-cell patch clamp recordings. The recordings were conducted at room temperature using Axopatch 200 (Axon Instruments). Kv1.3 expressing fibroblast were generated as previously described [Feld Y. et al. Circulation. (2002); 105:522-9].

Cell co-culturing—Primary monolayer cultures of neonatal rat (Sprague Dawley) ventricular myocytes were generated as previously described [Nuss H B, Marban E, Johns D C. Overexpression of a human potassium channel suppresses cardiac hyperexcitability in rabbit ventricular myocytes. *J Clin Invest*. 1999; 103:889-96]. Briefly, following excision, the ventricles were minced and treated with RDB (IIBR, Ness-Ziona, Israel). Following centrifugation, dispersed cells were suspended in culture medium (Ham's F10), 5% fetal calf serum, 5% horse serum, 100 U/ml penicillin, 100 mg/ml streptomycin (all from Biological industries, Beit Haemek, Israel), 1 mM $CaCl_2$ and 50 mg/100 ml bromodeoxyuridine (BrdU, Sigma). The cells were then cultured on gelatin coated (0.1%) microelectrode culture plates at a density of $1.5 \times 10^6$ cells/ml.

Once a well synchronous spontaneous activity was established in the cardiomyocyte cultures, fibroblasts (naïve, or Kv1.3 expressing fibroblasts) were seeded in a diffuse manner into the cardiomyocytic cultures. Two groups were studied: The cultures were studied daily, and the electrophysiological properties, essentially the spontaneous beating rate of the culture, was assessed at baseline and following application of the specific Kv1.3 blocker, Charybdotoxin (CTx), at increasing dosages (1, 10, 100 nM). The electrophysiological properties of the cultures were studied using a microelectrode array (MEA) mapping technique [Feld Y. et al. Circulation. (2002); 105:522-9].

Animals—Animal studies were approved by the Animal Board and Safety Committee of the Technion's Faculty of Medicine. Two animal models (rats and pigs) were used in this study. The swine model allowed electrophysiological studying using a range of cycle-lengths (CLs) between 350 and 500 ms for the basic (S1) stimulation drive, whereas the rat model allowed the use of a more rapid stimulation protocol with CL of 200 ms at the basic S1 train stimuli.

Rat model—Male Sprague-Dawley rats weighing 200-250 gr were anesthetized using A Xylasine (0.5 mg/kg) and Ketamine (0.5 mg/kg) preparation [see Example 7]. The animals were then intubated and ventilated using a Harvard small-animal mechanical respirator. The chest wall was opened using a left thoracotomy and the heart was exposed. After removal of the pericardium, a total of $6 \times 10^6$ cells (either fibroblasts without transfections in the control group or fibroblast overexpressing the KV1.3 channel in the study group) were transplanted into the anterior aspect of the left ventricular wall using a 28 g needle. In order to prevent graft rejection, all animals were treated with a daily dose of cyclosporin (10 mg/kg) and methyprednisolone (2 mg/kg). The animals underwent a detailed electrophysiological study (see below) immediately before cell grafting and 7 days post-transplantation.

Swine model—Three domestic pigs (20-30) kg were studied. Anesthesia was induced with 5-10 ml of intravenous sodium pentothal 2.5% solution and maintained with inhaled isoflurane (2%) in oxygen. Following a right thoracotomy, each heart was exposed and a total of $6 \times 10^6$ cells were transplanted at a total of 7 different locations in the anterior free wall of the right ventricle. Cells were delivered using a 25 g needle using an injection volume of 250 µl. The sites of cell transplantation were marked with a suture. To prevent graft rejection, the animals were treated with an immunosuppressive regimen (cyclosporine, 10 mg/kg/d and methylprednisolone, 3 mg/kg/d). 7 days following cell transplantation, a second thoracotomy and a detailed epicardial electrophysiological study were performed.

Cell labeling—transplanted fibroblasts were labeled prior to cell grafting with the nuclear fluorescent marker DAPI (Sigma) or with the fluorescent tracer, CFDA (Molecular probes, Eugene, Oreg., USA).

In vivo electrophysiological studies—The electrophysiological study in rats included a standard ventricular pacing protocol to determine the local myocardial effective refractory period (ERP). The ERP was evaluated by applying a train of 20 stimuli at a fixed cycle-length of 200 ms (S1), followed by a single premature stimulus (S2). The S1-S2 coupling interval was gradually shortened. The ERP was determined as the shortest S1-S2 coupling interval still capable of eliciting a ventricular response. Stimuli were generated using a computer controlled STG 1004 stimulus generator with the matching MC-Stim software (both from Multi Channel Systems, Reutlingen, Germany).

The ERP was measured at the site of cell transplantation and at remote sites, both prior to cell transplantation and seven days following cell grafting. In order to dissect the role of the overexpressed channel in altering the local myocardial electrophysiological properties, the ERP was measured also at each site following application of 9 µg/kg of Margatoxin (Alomone Labs, Jerusalem, Israel), a specific Kv 1.3 channel blocker as an intraperitoneal bolus.

The ERP in the pigs was measured in a similar manner to that in the rats but using slower basic stimulation intervals (CLs of 350, 400 and 500 ms). The ERP was measured at the site of cell transplantation as well as in remote sites and also following local intramyocardial injection of Margatoxin at the examined sites.

Immunostaining—At the end of the experiments the hearts were harvested and frozen in liquid nitrogen and cryo-sectioned (8 micron slices). Sections were first permeabilized using 1% triton and later blocked with 3% NGS and 0.1% triton for 1 hour at 37° C. Immunostaining was then performed using mouse anti-cardiac troponin I (cTnI) antibodies at a dilution of 1:3000 and rabbit anti-connexin 43 antibodies at a dilution of 1:100 (both antibodies were from Chemicon, Temicula, Ca) in blocking buffer for 24 hours at 4° C. Preparations where then incubated with Rhodamine-conjugated anti-mouse and FITC-conjugated anti-rabbit secondary antibodies at a dilution of 1:100 for 1 hour at room temperature. The preparations were then analyzed using an upright fluorescent microscope (Axioscop 2, Zeiss).

Computer simulation—A one-dimensional numeric mathematical model was used to provide mechanistic insights into the possible electrophysiological effects generated by the engineered cell grafts. This model simulates action potential propagation along a chain of five cardiomyocytes connected to an engineered fibroblast, overexpressing the Kv1.3 channel. The computer simulation was programmed using Matlab 6.5 software. The Lue and Rudy model[17] was followed [Luo C H, Rudy Y. A model of the ventricular cardiac action potential. Depolarization, repolarization, and their interaction. *Circ Res.* 1991; 68:1501-26] for the action potential simulation in each cell and the cable theory for intercellular conduction simulation.

The gap junction resistance between two myocytes was set to 10 KΩcm. The gap junction resistance between myocyte-fibroblast was set to $0.1/\sqrt{S}$ KΩcm (where S is the fibroblast surface area). Myocyte surface area was set to 1 cm$^2$ and the time step (dt) was set to 0.01 msec. The kinetic parameters of the voltage sensitive potassium channel Kv1.3 in the engineered fibroblast were taken from previous studies characterizing its biophysical properties [Marom S, Levitan I B. State-dependent inactivation of the Kv3 potassium channel. *Biophys J.* 1994; 67:579-89]. The maximum potassium current amplitude was derived from previous patch-clamp studies characterizing the transfected fibroblasts [Feld (2002) Supra] and was set to 125 nA/(mV·cm2).

Figure 22:
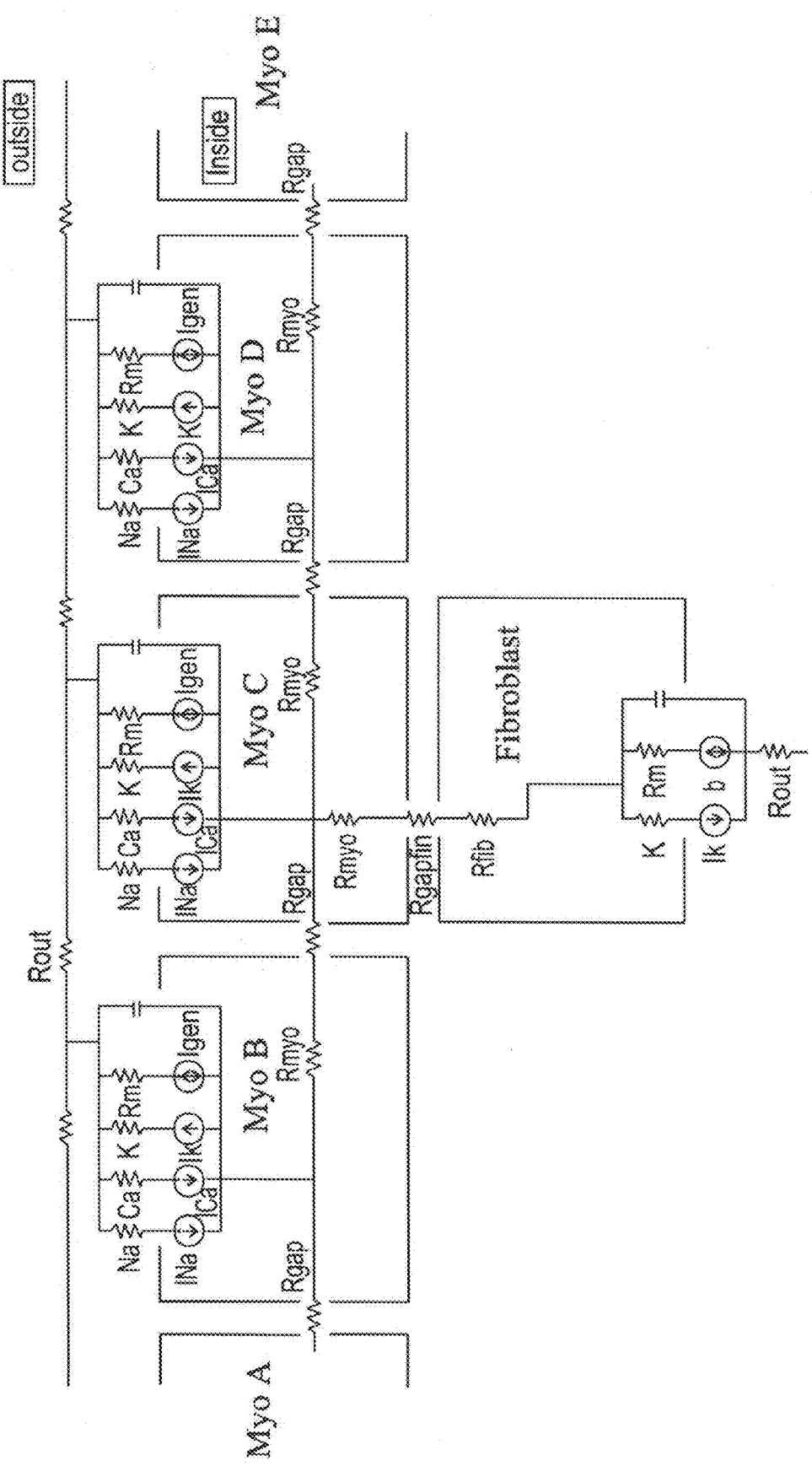
FIG. 22 is a one-dimensional passive electrical circuit model. Myo A-E are the myocytes and the fibroblast connects to myo C ($r_o$—extracellular resistance, $C_m$—membrane capacitance, $r_{myo}$, $r_{fib}$—longitudinal resistances, $R_{gapmm}$—resistance between myocytes, $R_{gapfm}$—resistance between myocyte and fibroblast), Ie the over expressed ion current.
Figure 23A:
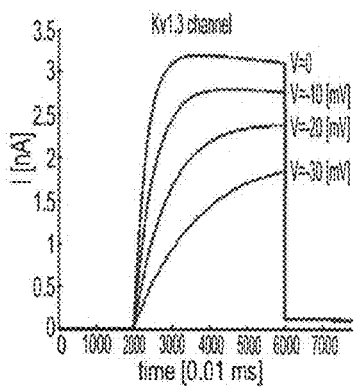
FIGS. 23a-j depict computer simulation of voltage clamp from cells expressing (FIG. 23a) Kv1.3 channels, (FIG. 23b) Kir2.1 channels, (FIG. 23c) SCN5A ΔKPQ channels and (FIG. 23d) Mut Kv1.3H401W Vs WT Kv1.3. Also shown is the refractory period in fibroblasts overexpressing (FIG. 23e) Kv1.3 channels (ERP=425±25 ms), (FIG. 23f) Kir2.1 channels (ERP=475±25 ms), (FIG. 23g) SCN5A □KPQ sodium channels (ERP=425±25 ms), (FIG. 23h), in native fibroblasts (i.e., without transfection, ERP=375±25 ms), (FIG. 23i) in the absence of fibroblasts (ERP=375±25 ms), and in fibroblasts overexpressing (FIG. 23j) Mut Kv1.3H401W channels (ERP=500±25 ms). Blue—Myo E membrane potential, Red—stimulus current.
Figure 23B:
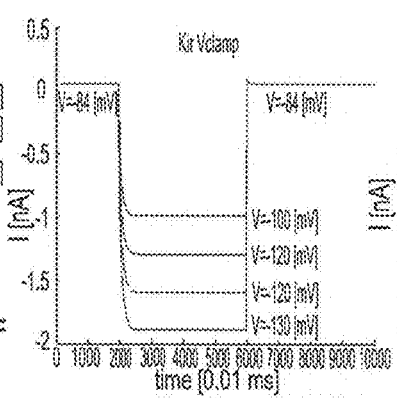
Figure 23C:
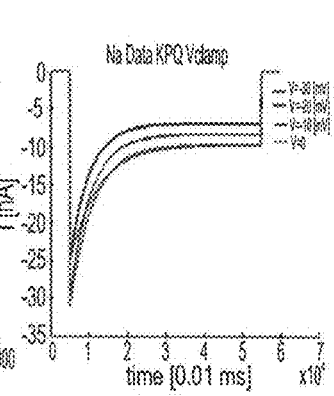
Figure 23D:
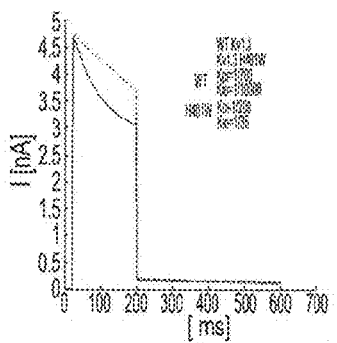
Figure 23E:
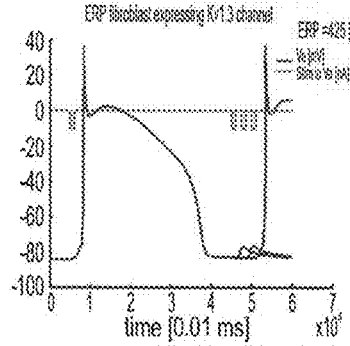
Figure 23F:
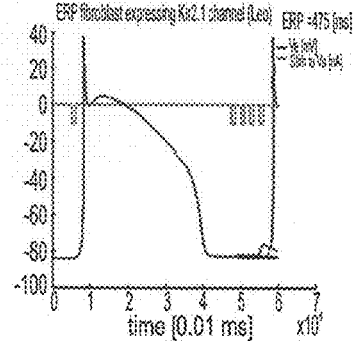
Figure 23G:
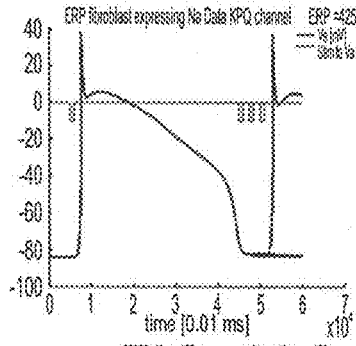
Figure 23H:
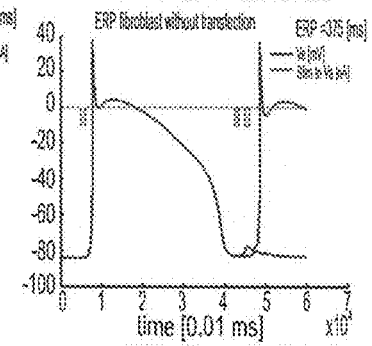
Figure 23I:
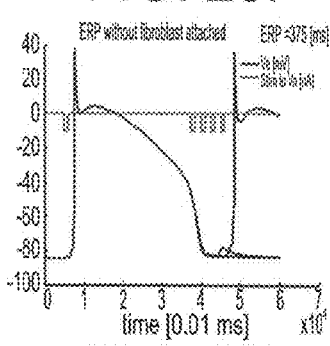
Figure 23J:
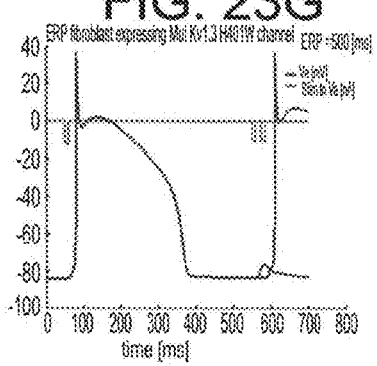

Electrophysiological measurement of the refractory period was simulated by applying two 10 nA/(mV·cm2) stimuli to myocyte A (FIG. 22). The time between two stimuli was gradually shortened. The effective refractory period (ERP) was defined as the minimum time interval between the two stimuli allowing the generation of an action potential in myocyte E (FIG. 22).

The refractory period generated by cell over expressing Kir channel, SCN5A ☐KPQ sodium channel, and mutant Kv1.3H401W was also simulated (FIG. 23).

Statistics—All results are expressed as mean±SEM. For the in-vivo experiments, data was compared using either paired or unpaired t-test. Data from the MEA experiment was compared using two ways ANOVA with repetition. Results were considered significant if P<0.05.

Results

In vitro studies—To determine the ability of the transfected fibroblasts to affect the excitable properties of cardiomyocytes, changes in the spontaneous beating rate of the hybrid cultures following cell grafting were followed. The electrophysiological properties of the transfected fibroblasts, overexpressing the voltage sensitive potassium current Kv1.3 channel, used in the current study, were previously evaluated in depth [Feld Y. et al. Circulation. (2002) 105:522-9]. These voltage-clamp studies demonstrated the presence of robust expression of the Kv1.3 channel with a high-magnitude outward potassium current of up to 4 nA recorded in the transfected fibroblasts. As expected, no significant currents were detected in non transfected fibroblasts that were used in the control co-cultures [Feld Y. et al. Circulation. (2002); 105: 522-9].

Figure 18A:
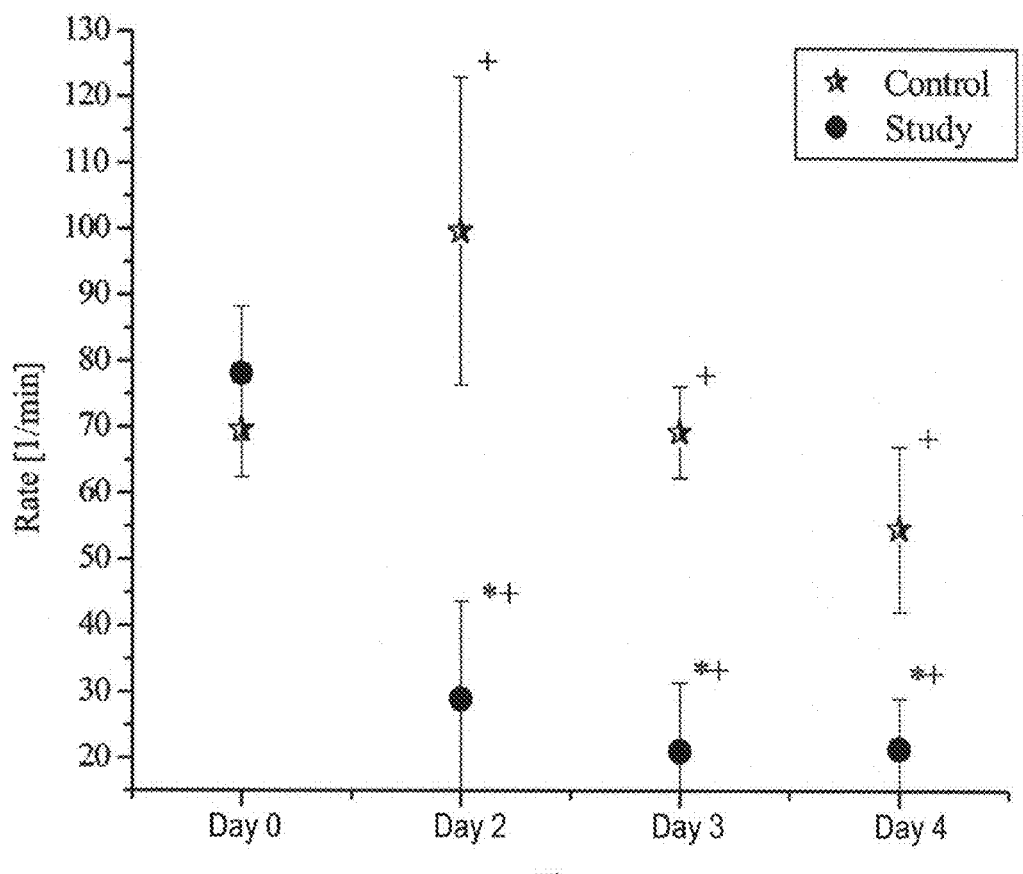
FIGS. 18a-b are graphs depicting the effect of Kv1.3 overexpressing fibroblasts on the average spontaneous beating rate of the rat heart (FIG. 18a) and reversion of this effect by the administration of an ion channel blocker (FIG. 18b).

The average spontaneous beating rate of both the control group (in which naive fibroblasts were seeded) and the study (in which the transfected fibroblasts were used) co-culture group were assessed daily (FIG. 18a). While the spontaneous beating frequency did not differ between the two groups at baseline (prior to cell grafting, FIG. 18a—day 0), a significant reduction in the spontaneous beating frequency of the study co-culture group was detected from day 2. This negative chronotropic effect, induced by the transfected fibroblasts was maintained during the entire experiment (FIG. 18a). Interestingly, in some of these co-cultures, cell grafting even resulted, in complete cessation of spontaneous beating. In contrast, grafting of naïve fibroblasts did not have a significant effect on beating frequency in the control group.

Figure 18B:
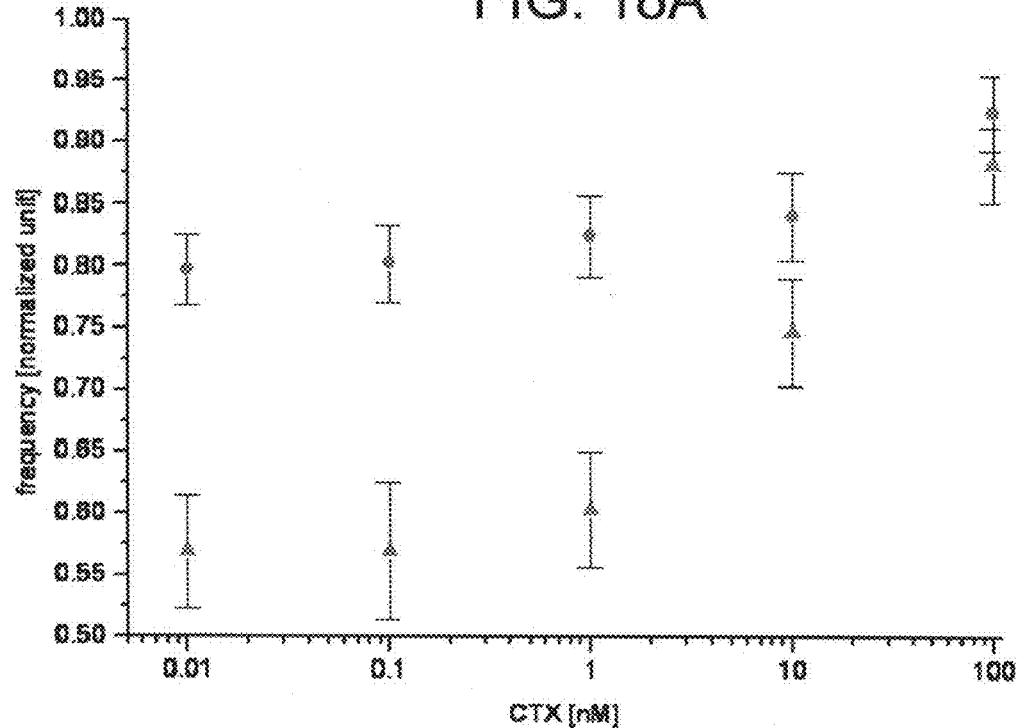

To dissect the possible contribution of the potassium current in the transfected fibroblasts to the generated electrophysiological effect in the co-cultures, the reversibility of this effect was addressed following administration of a Kv1.3 channel specific blocker, CTx. Administration of CTx had a dose-related effect in the study group (FIG. 18b) with full reversibility of the negative chronotropic effect induced by the transfected fibroblast when given at a dose of 100 nM. In contrast, CTx application did not significantly alter the beating frequency in the control group.

Figure 19A:
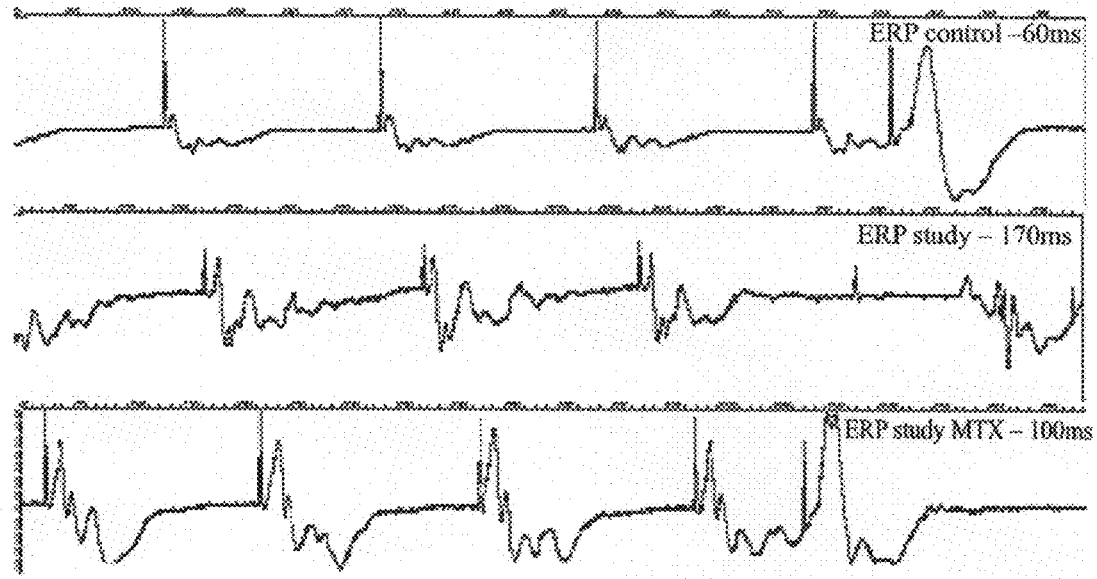
FIG. 19a is a representative ECG recording depicting changes in LV effective refractory period (ERP) of rats following grafting of fibroblasts transfected to express the voltage sensitive potassium channel Kv1.3 channel. Note the significant increase in the LV ERP at the site of cell transplantation (middle trace) when compared to the baseline recording (top). This change was reversed following application of the specific blocker of the Kv1.3 channel Margatoxin (bottom trace). Arrows indicate ERP interval.

In vivo effects of cell grafting—To evaluate the ability of the engineered cell graft to modify the local myocardial electrophysiological properties also in vivo, possible changes in the local ventricular refractory period were followed after transplantation in rats. FIG. 19a depicts the changes in the local effective refractory period (ERP) prior to—and a week following cell grafting at a site in the left ventricular myocardium in one of the animals. Note that the ventricular ERP (measured at a basic CL of 200 ms) was 60 ms prior to cell transplantation (FIG. 19a, top panel) and increased to 170 ms at the site of cell grafting (FIG. 19a, middle panel) seven days later. Interestingly, the increase in the local ERP at the site of cell grafting was partially reversed by the application of the specific Kv1.3 channel blocker, Margatoxin (MTx), with the ventricular ERP decreasing to 100 ms (FIG. 19a, bottom panel).

Figure 19B:
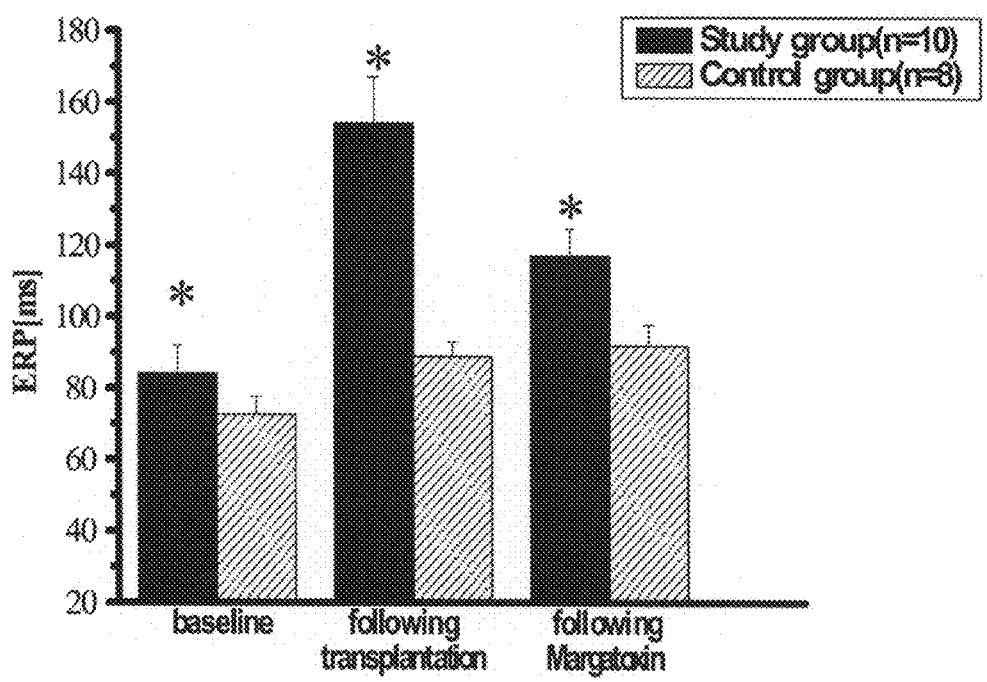
FIG. 19b is a bar graph summarizing the measured effective refractory period (ERP) in rats grafted with naive fibroblasts (black), genetically manipulated fibroblasts (stripes_ and following treatment with an ion channel blocker. In black, the control group of animals transplanted with non transfected fibroblasts. Note, ERP increased in the study group from 84±8.08 ms to 154±13.04 ms (P<0.05) 7 days after transplantation and decreased to 117±7.70 ms after the administration of Margatoxin. In the control group, no significant changes in ERP were observed.

The increase in the local ventricular ERP at the site of cell grafting was observed in all animals studied (n=10). This was manifested by an increase of the local ERP from a baseline value of 84±8 ms prior to cell grafting to a value of 154±13 ms (P<0.05) seven days later (FIG. 19b). The Kv1.3 potassium channel is highly sensitive to MTx, at concentrations that do not affect any of the cardiac channels. This allowed to examine whether the increase in the ERP was due to the presence of the transplanted fibroblasts in the native myocardium or due to the presence of the overexpressed potassium channels within the cells. Upon the administration of MTx, a significant decrease (P<0.05) was detected in the local ventricular ERP at the site of cell transplantation in all animals studied to a value of 117±8 ms (FIG. 19b).

In contrast to the above results, the local ventricular ERP at remote ventricular sites (at least 10 mms away from the site of cell transplantation) in the study group did not change seven days following the initial operation (86±7 ms). Similarly, in the control group, which consisted of animals (n=8) that were grafted with the same number of naive fibroblasts (lacking transfection) only a very mild increase in the local ERP was detected at the site of cell grafting from a baseline value of 73±5 ms to a value of 88±4 ms (FIG. 19b). This value did not change significantly following administration of Mtx (FIG. 19b).

Due to the relatively fast spontaneous beating rate of the rat heart, the effects of cell grafting on the local ventricular refractoriness could only be detected at rapid ventricular stimulation rates (CL-200 ms). To assess whether the grafted cells could increase refractoriness also at more clinically relevant, slower ventricular rates (longer CLs), a swine model was used. FIG. 20 displays the electrophysiological changes observed seven days following grafting of the transfected cells in the right ventricular free wall of a pig. Noteworthy is that the ventricular ERP at the site of cell transplantation (FIG. 20a, middle panel) significantly increased to 310 ms (at a basic CL drive of 400 ms) when compared to control myocardial sites in which the measured ERP was 210 ms (FIG. 20a, top panel). The increase in the ventricular ERP, observed at the site of cell grafting, was reversible upon the local application of MTx with the local ERP value decreasing to 220 ms.

The lower ventricular rate in the swine model allowed assessing of the electrophysiological effects of cell grafting using three different basic CL drives: 350, 400, and 500 ms. As is shown in FIG. 20b, transplantation of the transfected fibroblasts resulted in a significant increase (p<0.05) in the local ventricular ERP at all three CLs when compared to non-transplanted areas. The increase in the local ventricular ERP was reversible in all cases with the ventricular ERP decreasing to values not different from the control sites following local application of MTx (FIG. 20b).

Figure 21A:
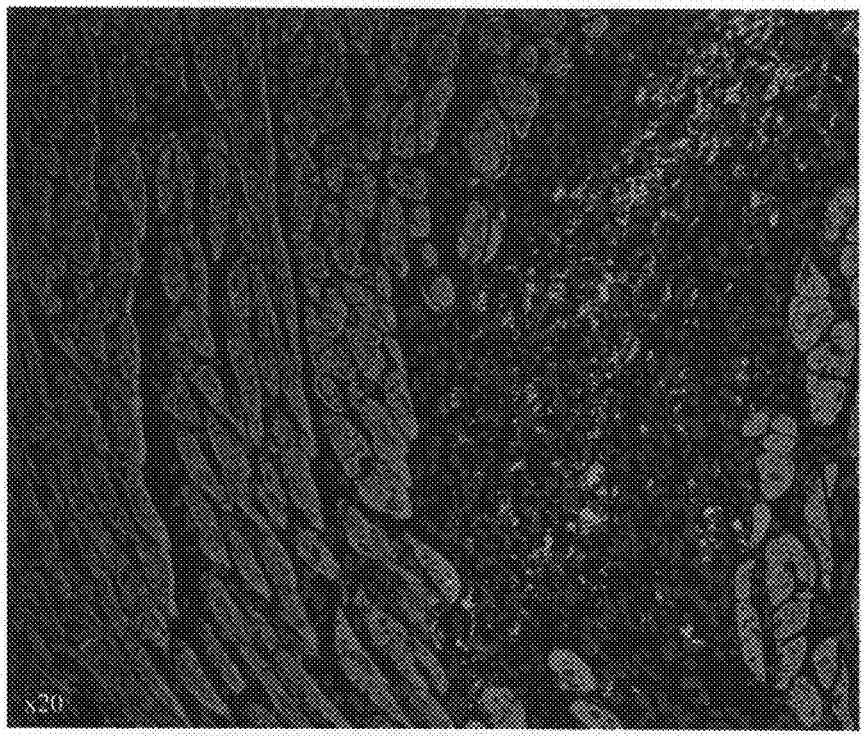
FIGS. 21a-b are photomicrographs showing the presence of grafted cells within the rat myocardium, as detected by immunostaining.
Figure 21B:
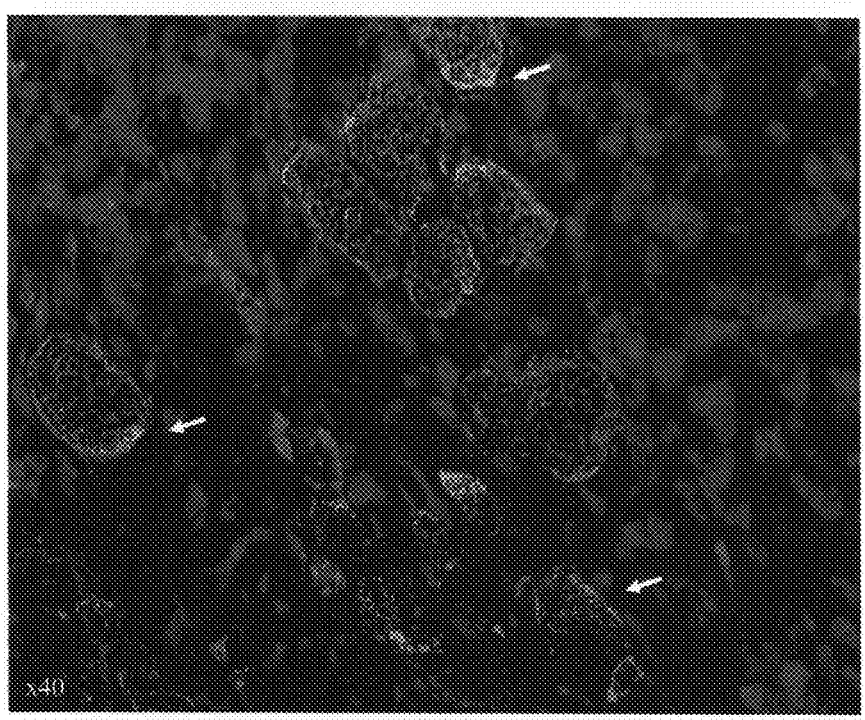

After harvesting the hearts, the presence of the grafted cells at the site of cell transplantation was validated. The grafted cells were labeled prior to transplantation either by the fluorescent tracer CFDA (FIG. 21a) or with the nuclear fluorescent marker DAPI (FIG. 21b). As can be seen in the immunostaining confocal image, the grafted fibroblasts could be easily detected (green labeled cells in FIG. 21a, and DAPI labeled cells in FIG. 21b) within the rat's myocardium along the needle's track. Interestingly, gap junctions could be recognized at the interphase between the grafted fibroblasts and host cardiomyocytes as identified by the positive punctuate staining for connexin 43 (green staining, arrows in the FIG. 21b).

Modeling results—In order to achieve further insights into the possible mechanisms by which the transfected fibroblast could modulate the excitable properties of host cardiac tissue, computer simulation was employed. This simulation utilizes simplified one-dimensional numeric mathematical model that simulates action potential propagation along a chain of five cardiomyocytes connected to an engineered fibroblast (FIG. 22e). The computer simulation was run for four different alternative strategies: (a) for a chain of cardiomyocytes without a connecting fibroblast, (b) with a connected naïve fibroblast (without any currents), (c) with a connected fibroblast overexpressing the voltage-gated potassium channels Kv1.3, and (d) the same as (c) but without the unique inactivation properties of the Kv1.3 channel.

The results of the above-mentioned four simulations are depicted in FIGS. 22a-d. The effective refractory period (ERP) was defined as the minimum time deference between two stimuli applied to myocyte A that were conducted to all five myocytes (including myocytes C which is linked to the fibroblast). In the setup of five myocytes without a connecting fibroblast, the measured ERP was 375 ms (FIG. 22a) in this case. When a fibroblast without transfection was connected to myocytes C, the ERP did not change and remained 375 ms (FIG. 21b). In contrast, when the myocyte was connected to a fibroblast overexpressing the Kv1.3 channel, the same coupling interval (375 ms) resulted in the inability to induce action potential in myocytes C and consequentially in failure in conduction to myocytes D (FIG. 22c). Only longer CLs enabled impulse conduction through myocytes C. The changes in the ERP induced by the connecting fibroblats dependent on several factors. FIG. 22D, for example, shows that the ERP increased significantly with relation to the fibroblast surface area (FIG. 21d). Hence, by increasing the surface area of the connecting fibroblasts a larger sink is generated and results in a significant prolongation of the myocytes refractory period.

When the inactivation property of the Kv1.3 channel was removed, the ERP was shorter than the refractory period measured without a fibroblast connected. The last result suggest that the reason that fibroblast transfected with Kv1.3 channel lengthened the refractory period is that during phase 4 of the action potential Kv1.3 channels are in the state of inactivation and are moving to the close state through the open state. The inactivation time constants for the Kv 1.3 channel are very long—inactivation to open—Kio $1/10$ $Sec^{-1}$, and open to inactivation—Koi $1/0.7$ $Sec^{-1}$. The result is the generation of a relatively long tail current following repolarization [Marom (1994) Supra]. The tail current serves as a current sink to myocyte C, limiting the possibility for action potential generation long after repolarization occurs.

As mentioned hereinabove, traditional pharmacotherapy for the different cardiac tachyarrhythmias is limited by relatively low efficacy and significant side effects due to global cardiac action and systemic effects. The above-described shows a new approach for the modification of the myocardial electrophysiological properties by using genetically engineered cell grafts, transfected ex vivo to express specific ionic currents. Using fibroblasts engineered to express the voltage gated potassium current Kv1.3, the validity of this concept was demonstrated by showing the ability of the cells to reduce local excitability and prolong the local refractory period in ex vivo, in vivo, and computer simulation studies.

The ability of the transfected fibroblasts to modulate the local ventricular electrophysiological substrate as shown in the in vivo studies indicates the ability of the engrafted cells to survive following cell transplantation, their ability to integrate with host tissue, and their ability to modulate local excitability by the generation of electrotonic currents with neighboring cardiomyocytes. In order for the transfected channel to exhibit its effect on the surrounding native myocardium, the fibroblasts carrying the channel must be electrically coupled to the neighboring myocytes. The possibility of such an electrical connectivity between cardiomyocytes and fibroblasts was previously demonstrated in the work of Rook et al [Rook M B, Jongsma H J, de Jonge B. Single channel currents of homo- and heterologous gap junctions between cardiac fibroblasts and myocytes. *Pflugers Arch*. 1989; 414: 95-8] who demonstrated morphological connectivity in cardiomyocytes—fibroblast pairs in the appearance of connexin 43 gap junction protein, by Fast at al [Fast V G, Darrow B J, Saffitz J E, Kleber A G. Anisotropic activation spread in heart cell monolayers assessed by high-resolution optical mapping. Role of tissue discontinuities. *Circ Res*. 1996; 79:115-27] who reported on electrical interactions in cultured cardiomyocytes harboring fibroblasts within them, and by a recent report by the present inventors showing the ability of transfected fibroblast to create local conduction blocks in co-culture experiments. More recently, Gaudesius et al. [Gaudesius G, Miragoli M, Thomas S P, Rohr S. Coupling of cardiac electrical activity over extended distances by fibroblasts of cardiac origin. *Circ Res*. 2003; 93:421-8] have managed to show the ability of fibroblasts to propagate electrical signals over extended distances of up to 300 microns in co-cultures.

In order for the long-term in vivo effects observed herein to occur, the transplanted cells must survive the procedure for at least seven days and generate electrical connections with host cells that result in a large enough electrotonic currents to generate a measurable effect. Interestingly, albeit several in vitro demonstrations of electrotonic currents appearing between fibroblasts and cardiomyocytes, the present inventors have previously shown [Feld Y, Melamed-Frank M, Kehat I, Tal D, Marom S, Gepstein L. Electrophysiological modulation of cardiomyocytic tissue by transfected fibroblasts expressing potassium channels: a novel strategy to manipulate excitability. *Circulation*. 2002; 105:522-9] that non transfected fibroblasts do not induce significant changes in activation patterns of cultured cardiomyocytes. The results presented herein demonstrate that the electrophysiological effect created by the implantation of the cells can be directly related to the activity of the transfected channels, as reflected from the lack of an effect in the control group, in which animals were treated with non transfected cells, and furthermore, by the reversibility of the effect seen in the animals receiving channel expressing fibroblasts upon the administration of the specific Kv1.3 blocker Margatoxin.

The mutated potassium channel used in this work, Kv1.3, was comprehensively studied and described by Marom et al [Marom S, Levitan I B. State-dependent inactivation of the Kv3 potassium channel. *Biophys J*. 1994; 67:579-89; Marom S. Slow changes in the availability of voltage-gated ion channels: effects on the dynamics of excitable membranes. *J Membr Biol*. 1998; 161:105-13]. Several properties made it suitable for the purpose of imposing changes on the action potential morphology of neighboring cardiomyocytes. First, the robust potassium current and the readiness of its achievement allow a significant outward restraining current. Second, the slow kinetics for transition from open to closed states allows a possible effect in late stages of the action potential. And last, the fact that the channel is not expressed in the native myocardium and its sensitivity to the specific blocker Margatoxin provides the possibility to exclusively control the behavior of the channel when expressed by the fibroblasts and integrated into the myocardium.

Several important conclusion can be drawn from the results presented herein [Scheinman M M. NASPE Survey on Catheter Ablation. *Pacing Clin Electrophysiol*. 1995; 18:1474-8]: Transplantation of fibroblasts genetically reprogrammed to express a voltage gated potassium channel altered the local effective refractory period (ERP) in a localized manner [Kusumoto F M, Goldschlager N. Cardiac pacing. *N Engl J Med*. 1996; 334:89-97]. Transplantation of non transfected fibroblasts did not result in alteration of the ERP [Moss A J, Zareba W, Hall W J, Klein H, Wilber D J, Cannom D S, Daubert J P, Higgins S L, Brown M W, Andrews M L. Prophylactic implantation of a defibrillator in patients with myocardial infarction and reduced ejection fraction. *N Engl J Med*. 2002; 346:877-83]. The activity of the introduced channel could be reversed in vivo by a systemic administration of a specific blocker, allowing a significant reduction in the effect [Echt D S, Liebson P R, Mitchell L B, Peters R W, Obias-Manno D, Barker A H, Arensberg D, Baker A, Friedman L, Greene H L, et al. Mortality and morbidity in patients receiving encamide, flecamide, or placebo. The Cardiac Arrhythmia Suppression Trial. *N Engl J Med*. 1991; 324:781-8]. Fibroblasts survived in the heart at least 7 days after transplantation.

FIG. 21 provides an example for a section from a rat heart 7 days after the transplantation of fibroblasts. In this section, blue DAPI labeled nuclei of fibroblasts are aligned aside to the native heart cells, seen in red. Gap junction channels are depicted in green. The border zone between the graft and the cardiomyocytes is characterized by the appearance of a vast uniform appearance of gap junctions. A subset of animals was kept alive for a period of 28 days. When the hearts were excised and histological evaluation was effected, the fibroblasts could be readily visualized at the site of transplantation, with no apparent reduction in number. For an in-depth evaluation of the electrophysiological alteration elicited in the present study, a computer simulation was designed, allowing the prediction of the effect. Using this model, componential analysis of the electrical effect that resulted in the simulation was conducted. When the simulation was programmed to disregard the inactivation properties of the channel, no significant increase in the ERP could be detected. When the inactivation component was added, the significant, cell surface related increase in the ERP was revealed. This surprising finding helped to address the riddle of the mechanism underlying the observed electrophysiological effect of an increase in the ERP. A possible explanation may be provided by the inactivation properties of the KV1.3 channels. When a myocyte is activated and depolarized, a voltage difference is created between it and the neighboring transplanted fibroblast. This voltage difference results in an electrotonic current, flowing from the myocyte to the fibroblast via gap junction channels. The resulting rise in the fibroblast's membrane potential may lead to the opening of the voltage gated potassium channels and the generation of an outward potassium current from the fibroblasts as a result. This current, sustained throughout the action potential period, influences directly on the myocyte's action potential morphology. These changes include: (1) phase 0 of the action potential decreases, as was previously observed [Feld (2002) Supra] to create conduction velocity delays in vitro, (2) the amplitude of the action potential is decreased, and (3) the action potential duration is shortened.

The ability to increase the refractory period is imparted by the inactivation property of the KV1.3 potassium channel. Shortly after the activation and the opening of the channel, the channel shifts to its inactive state. From this state the channel can not return to a closed state, but rather has to go through the open state in order to close. It is during the time of transition from an inactivated to close states, through the open state, that the important current results. This tail current is present during the late phases of the action potential and continues through the diastolic phase of the action potential. As long as this tail current occurs, it serves as a restraining current resisting an electrical activation. The fibroblast if so, serves as a current sink during this time, leading to the prolongation of the effective refractory period.

This novel exciting treatment modality is based on the utilization of cell grafts that can be genetically manipulated ex vivo to display specific electrophysiological characteristics and then be grafted to the in vivo heart. This approach is featured by a number of theoretical advantages over direct gene therapy. These advantages may be related to a better efficiency and control of the transfection process ex vivo. Additionally, several ion channels and other electrically related components may be combined together in one cell, allowing a variety of electrophysiological effects that could be specifically designed in a manner that would generate electrophysiological behaviors that are absent in the native context. Another advantage is the ability to screen the phenotypic properties of the cells prior to transplantation, and the possible achievement of long-term effect since cardiac cell grafts were demonstrated to survive for prolonged periods following transplantation [Muller-Ehmsen J, Peterson K L, Kedes L, Whittaker P, Dow J S, Long T I, Laird P W, Kloner R A. Rebuilding a damaged heart: long-term survival of transplanted neonatal rat cardiomyocytes after myocardial infarction and effect on cardiac function. *Circulation*. 2002; 105: 1720-6].

Thus, the present approach can be applied as a tool for terminating arrhythmogenic conduction circuits. Generation of different ion channel compositions within an engineered cell, serving as a transplantable electrical modulating agent, may offer an innovative, pathology oriented tool for modifying the electrophysiological properties of the cardiac tissue for the treatment of cardiac arrhythmia.

Example 9

Modulation of Neuronal Discharge by the Present Invention

Background

Neurological disorders are a major cause of morbidity and mortality. There are more than one million Americans that suffer from Parkinson's disease [N Engl J Med 1998 Oct. 8; 339(15):1044-53]. According to the National Society for Epilepsy—Epilepsy appears in 1 in 200 people.

Neurological disorders are associated with increase or decrease of neuronal discharge at specific loci and/or distributed loci in the central nervous system (CNS) or peripheral nervous system (PNS).

Modulation of the neural activity in specific areas may result in improvement of neurological disorders. Examples are focal ablation of epileptic foci, and deep brain stimulation for the treatment of Parkinson's disease (N Engl J Med 2001; 345:956-63).

One available evidence indicates that only connexin32, connexin36, connexin43 and connexin47 are expressed in neurons [Nat Rev Neurosci. 2001 June; 2(6):425-33]. Using freeze-fracture and immunogold labeling, it has been shown that only connexin36 is present at gap junctions between neurons, whereas connexin32 and connexin43 are present at glial gap junctions [Proc Natl Acad Sci USA. 2000 Jun. 20; 97(13):7573-8]. Connexin47 is a neuron-specific connexin with a wide distribution in the CNS [J Neurosci. 2001 Feb. 15; 21(4):1117-26]. Connexin36 is expressed specifically in parvalbumin-expressing GABA interneurons [Brain Res. 2000 May 19; 865(1):121-38].

Modulation of neuronal discharge can be achieved by two major strategies, first, increasing or decreasing efficacy of electrical and/or chemical synaptic coupling between neurons; second, increasing or decreasing intrinsic neuronal excitability properties (e.g. increase/decrease bursting rate, bursting duration, silent duration, and bursting amplitude). Both strategies may be realized by transplanting cells capable of forming gap junction. Examples are microglia or oligodendrocytes or astroglia or Mesenchymal stem cells [J Physiol. 2004 Mar. 16; 555(Pt 3):617-26] or fibroblasts [Circ Res. 2003 Sep. 5; 93(5):421-8. Epub 2003 Jul. 31]. Such cells, by virtue of their intrinsic electrical properties (passive, e.g. capacity, and/or active elements, e.g. ionic channels), coupled electrically to the neuronal cells, will exert their said modulatory effects.

Modulation of neuronal discharge may also be achieved by transplantation of cell grafts overexpressing connexin channels (e.g. connexin32, connexin36, connexin43, connexin47) and/or overexpressing voltage-gated and/or ligand-gated ion channels (e.g. sodium channels, calcium channels, Acetyl-Cholin receptor channels, leak channels, potassium channels). Examples for sodium channels: (a) SCN5A, (b) Mutant SCN5A (ΔKPQ, N1325S, R1644H, E1295K, D1790G, ins1795) (these mutations cause LQTS and/or Brugada syndrome, and are characterized by long activation, and/or persistent current), (c) SCN1A, (d) SCN2A, (e) SCN3A, (f) SCN4A, (g) SCN8A, (h) SCN9A, (i) SCN10A, (j) SCN11A. Examples for calcium channels are: (a) L-type, (b) T-type, and (c) N-type calcium channels. Examples for non-selective depolarizing ion channels (HCN channel family: e.g. hHCN2, hHCN4, mHCN1, mHCN2). Examples for ACh receptor channels are Kir3.1, Kir3.2, Kir3.3 and Kir3.4). Examples for LEAK channels are of the KCN-K family channel). Examples for potassium channels are voltage gated family e.g. Kv1.1, Kv1.2, Kv1.3 mutant Kv1.3H401W or inward rectifier family e.g. Kir2.1.

Another alternative is overexpression of depolarizing (e.g. sodium channels, calcium channels, non-selective ion channels) or hyperpolarizing (e.g. potassium or chloride ion channels) ion channels by neurons or microglia or oligodendrocytes or astroglia (with or without the use of grafted cells).

The inhibitory network is of a particular interest. These neurons form an electrically coupled sub-network that controls the activity of surrounding excitable neurons. Most importantly the coupling between these inhibitory neurons is via connexin36. Cells expressing or overexpressing connexin36 may serve as an attractive vehicle to modulate the inhibitory networks function at specific areas in the CNS. These cells may increase inhibitory interneuron coupling, and therefore increase the inhibitory system function at a specific location. Increasing the inhibitory networks function will result in a decrease of the overall function at the specific area. This effect on the inhibitory networks can be further enhanced by using cells that overexpress depolarizing ion channels. This approach can serve as a novel treatment modality for depressing epileptic foci and/or pain release. Furthermore, modulating the activity of the subthalamic nucleous and/or the internal globus pallidum and/or the zona increta and/or the nigra reticulata can serve for the treatment of Parkinson's disease [Lang E A. Et al. N Engl J Med. 1998 Oct. 15; 339(16):1130-43. Review]. It is also possible to decrease the inhibitory network function by using cells expressing and/or overexpressing connexin36 and hyperpolarizing ion channels (e.g. potassium channels (Potassium channels: Kv family, Kir family, HERG, Delayed rectifier, and chloride channels: CIC family: CIC1, CIC2, CICN3, CIC4, CIC6). Decreasing the inhibitory system will result in increase excitability of specific areas in the CNS. This approach may be utilized for the treatment of Alzheimer's disease, and other neurodegenerative disorders.

Another alternative approach is the use of cells expressing and/or overexpressing connexin47 in order to increase pyramidal or purkinje cell coupling. Furthermore, pyramidal or purkinje cells coupling may be enhanced by cells expressing or overexpressing connexin47 and depolarizing ion channels. Increasing pyramidal or purkinje cells coupling and/or excitability may be used for regaining functionality in brain areas after lesion due to CVA or other brain damages. Moreover, pyramidal or purkinje cell excitability can be decreased by utilizing cells expressing or overexpressing connexin47 and hyperpolarizing ion channels. This strategy can be used for the treatment of epilepsy or phantom pain.

Overexpression of ion channels or connexin by neurons or microglia or oligodendrocytes or astroglia can be effected by in-vivo gene therapy involving direct stereotaxis guided injection of naked DNA or virus vector carrying the DNA sequence. Alternatively, injection of the naked DNA or virus vector carrying the DNA sequence to an artery feeding the specific area in the CNS. Systemic administration of DNA may be effected by intravenous injection using a promoter specific to neuron or microglia or oligodendrocytes or astroglia.

Ex vivo gene transfer may involve the use of autologous, allogenic, or xenogenic cells. The cells must be capable of forming electrical coupling with host cells in a specific area in the CNS either by the expression of an endogenous protein or by overexpressing a protein capable of creating electrical coupling.

The cells can be transplanted in the CNS following expansion and/or genetic manipulation by one or more of the following procedure: direct stereotaxis guided injection of the cells [Kakishita K et al. Experimental Neurology 165, 27-34 (2000)]; or injection of the cells to an artery feeding the specific area in the CNS.

Materials and Experimental Procedures

Animals—Rat model of Parkinson's disease were produced as previously described [$Exnr.$ 2000. 165:27-34]. Briefly, rats were anesthetized with a combination of Ketamine 120 mg/kg and Xylazine 17 mg/kg. Unilateral lesions of the ascending mesostriatal DA pathway were performed. Briefly, Under anesthesia 6-hydroxydopamine (Sigma; 3 mg/ml in 0.2 mg/ml ascorbate/saline) was stereotaxically injected at two sites: (First) 2 ml at 4.0 mm posterior to the bregma, 0.8 mm to the right, and 8.0 mm below the dural surface with the tooth-bar set at 3.4 mm above the interaural line; and (Second) 2.5 ml at 4.4 mm posterior to the bregma, 1.2 mm to the right, and 8.0 mm below the dura with the tooth-bar set at 2.3 mm below the interaural line. Amphetamine-Induced Circling Behavior was assessed before cellular transplantation.

Cellular transplantation to the subthalamic nucleus (STN)- $1\text{-}10\times10^6$ genetically engineered fibroblasts expressing Kv1.3 (Feld et al. $Circulation$. 2002 January; 105: 522-529) were suspended in 50 µl saline. STN coordinates were based on the Paxinos and Watson rat brain atlas. The following coordinates were used for the STN (with respect to bregma and dura levels): antero-posterior (AP) 23.8 mm, lateral (L) 2.2 mm, and vertical (V) 7.8 mm, with the tooth-bar at 23.3 mm. The cells (50 µl) were injected over 1 min. The cannula was left in place for 2 min and slowly retracted. For the control group fibroblasts without transfection were used. Following transplantation amphetamine or apomorphine-Induced Circling Behavior were assessed for evaluation of the cellular graft effect [Kakishita K et al. Experimental Neurology 165, 27-34 (2000)].

Results

Figure 24:
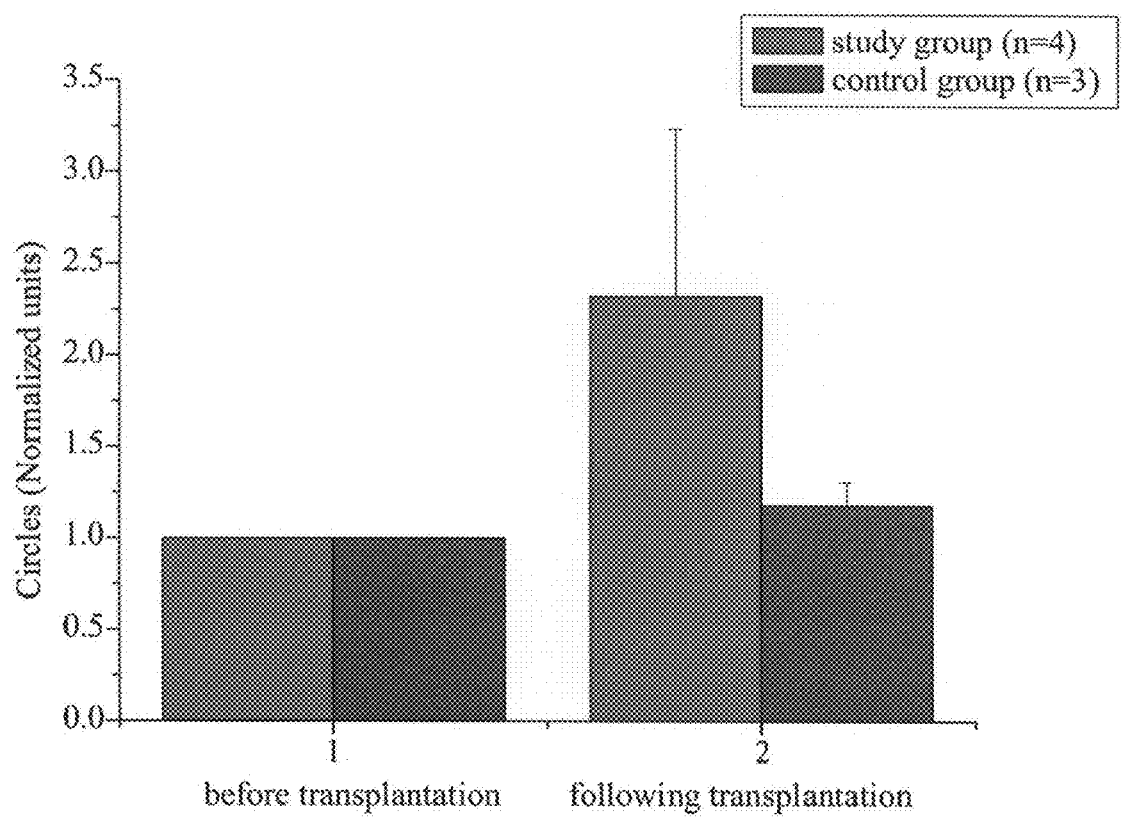
FIG. 24 is a bar graph depicting the circling behavior of Parkinson's disease model rats grafted with naïve fibroblasts (control group—green, n=3) or with Kv1.3 expressing fibroblasts (study group—red, n=4).

As is shown in FIG. 24, injection of fibroblasts overexpressing Kv1.3 potassium channels to the STN of rats (n=4) caused an increase in the circulating behavior of 130±90% while fibroblasts without transfection caused an increase of 18±12%.

These results indicate that the transfected fibroblasts may have inhibited the inhibitory system of the STN, and therefore, increased the overall activity of the STN, thus aggravating the circulatory behavior of the Parkinsonian rats.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences disclosed therein and/or identified by a GeneBank accession number mentioned in this specification are herein incorporated in their entirety by reference into the specification, to the same extent as if each individual publication, patent, patent application or sequence was specifically and individually indicated to be incorporated herein by reference. In addition, citation or identification of any reference in this application shall not be construed as an admission that such reference is available as prior art to the present invention.

REFERENCES

Additional References are Cited in the Text

1. Bayly P. V, Bruce H. Ken Knight, Jack M. Rogers, Russel E. Hillsley, Raymond E. Ideker, William M. Smith. Estimation of conduction velocity vector fields from epicardial mapping data. IEEE transactions on biomedical engineering. 1988. 45:563-571.
2. Fast V G, Kleber A G. Microscopic conduction in cultured strands of neonatal rat heart cells measured with voltage-sensitive dyes. Circ Res. 1993. 73: 914-925.
3. Gussoni, E., Pavlath, G. K., Lanctot, A. M., Sharma, K. R., Miller, R. G., Steinman, L. and Blau, H. M. Normal dystrophin transcripts detected in duchenne muscular dystrophy patients after myoblast transplantation. Nature. 1992. 356: 435-438.
4. Marom s, Goldstein S A, Kupper J, Levitan I B. Mechanism and modulation of inactivation of the Kv3 potassium channel. *Receptor and Channels*. 1993. 1:81-88.
5. Rook M B, Van Ginneken A C G, De Jonge B, Aoumari A E, Gros D, and Jongsma H J. Differences in gap junction channels between cardiac myocytes, fibroblasts, and heterologous pairs. Am J Physiol. 1992. 263: C959-C977.
6. Rubin Y, Kessler-Icekson G, Navon G. The effect of furosemide on calcium ion concentration in myocardial cells. Cell Calcium. 1995 August; 18(2):135-9.
7. Spach M S, Dolber P C. Relating extracellular potentials and their derivatives to anisotropic propagation at a microscopic level in human cardiac muscle. Evidence for electrical uncoupling of side-to-side fiber connections with increasing age. Circ Res. 1986 March; 58(3):356-71.
8. Tompson, L. Fetal transplants show promise. Science. 1992. 257: 868-870.
9. Waldo A L, Camm A J, deRuyter H, Friedman P L, MacNeil D J, Pauls J F, Pitt B, Pratt C M, Schwartz P J, Veltri E P. Effect of d-sotalol on mortality in patients with left ventricular dysfunction after recent and remote myocardial infarction. The SWORD Investigators. Survival With Oral d-Sotalol. *Lancet*. 1996; 348:7-12.
10. Hoppe U C, Johns D C, Marban E, O'Rourke B. Manipulation of cellular excitability by cell fusion: effects of rapid introduction of transient outward K+ current on the guinea pig action potential. *Circ Res*. 1999; 84:964-72.
11. Johns D C, Nuss H B, Chiamvimonvat N, Ramza B M, Marban E, Lawrence J H. Adenovirus-mediated expression of a voltage-gated potassium channel in vitro (rat cardiac myocytes) and in vivo (rat liver). A novel strategy for modifying excitability. *J Clin Invest*. 1995; 96:1152-8.
12. Nuss H B, Johns D C, Kaab S, Tomaselli G F, Kass D, Lawrence J H, Marban E. Reversal of potassium channel deficiency in cells from failing hearts by adenoviral gene transfer: a prototype for gene therapy for disorders of cardiac excitability and contractility. *Gene Ther*. 1996; 3:900-12.
13. Nuss H B, Marban E, Johns D C. Overexpression of a human potassium channel suppresses cardiac hyperexcitability in rabbit ventricular myocytes. *J Clin Invest*. 1999; 103:889-96.
14. Johns D C, Marban E, Nuss H B. Virus-mediated modification of cellular excitability. *Ann NY Acad Sci*. 1999; 868:418-22.
15. Mazhari R, Nuss H B, Armoundas M, Winslow R L, Marban E. Ectopic expression of KCNE3 accelerates cardiac repolarization and abbreviates the QT interval. *J Clin Invest*. 2002; 109:1083-90.
16. Donahue J K, Heldman A W, Fraser H, McDonald A D, Miller J M, Rade J J, Eschenhagen T, Marban E. Focal modification of electrical conduction in the heart by viral gene transfer. *Nat Med*. 2000; 6:1395-8.
17. Edelberg J M, Aird W C, Rosenberg R D. Enhancement of murine cardiac chronotropy by the molecular transfer of the human beta2 adrenergic receptor cDNA. *J Clin Invest*. 1998; 101:337-43.
18. Miake J, Marban E, Nuss H B. Biological pacemaker created by gene transfer. *Nature*. 2002; 419:132-3.
19. Qu J, Plotnikov A N, Danilo P, Jr., Shlapakova I, Cohen I S, Robinson R B, Rosen M R. Expression and function of a biological pacemaker in canine heart. *Circulation*. 2003; 107:1106-9.
20. Feld Y, Melamed-Frank M, Kehat I, Tal D, Marom S, Gepstein L. Electrophysiological modulation of cardiomyocytic tissue by transfected fibroblasts expressing potassium channels: a novel strategy to manipulate excitability. *Circulation*. 2002; 105:522-9.
21. Luo C H, Rudy Y. A model of the ventricular cardiac action potential. Depolarization, repolarization, and their interaction. *Circ Res*. 1991; 68:1501-26.

What is claimed is:

1. A method of treating a disease treatable by modulating neural excitability in a subject, the method comprising administering to the subject, at a site capable of generating an epileptic stimulus, a therapeutically effective amount of non-genetically modified fibroblasts capable of electrical coupling with a neural tissue of the subject, thereby treating the disease treatable by modulating neural excitability in the subject.

2. The method of claim 1, wherein modulating neural excitability is decreasing neural excitability.

3. The method of claim 1, wherein the disease is Parkinson's disease and/or epilepsy.

* * * * *

SEQUENCE LISTING

<160> NUMBER OF SEQ ID NOS: 4

<210> SEQ ID NO 1
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 1
atggcaaact tcctattacc t                                              21

```
<210> SEQ ID NO 2
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 2
ggcagaagcc tcgagccaga at                                             22

<210> SEQ ID NO 3
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 3
tcgatatgtt ctatgagatc tg                                             22

<210> SEQ ID NO 4
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 4
ctcacacgat ggactcacg                                                 19
```